US008247437B2

(12) United States Patent
Swinnen et al.

(10) Patent No.: US 8,247,437 B2
(45) Date of Patent: Aug. 21, 2012

(54) N-HYDROXYAMIDE DERIVATIVES AND USE THEREOF

(75) Inventors: Dominique Swinnen, Beaumont (FR);
Agnes Bombrun, Chambesy (CH);
Jerome Gonzalez, Annemasse (FR);
Stefano Crosignani, St. Genis-Pouilly (FR); Patrick Gerber, Etoy (CH);
Catherine Jorand-Lebrun,
Contamine-Sarzin (FR)

(73) Assignee: Merck Serono SA, Coinsins (CH)

( * ) Notice: Subject to any disclaimer, the term of this patent is extended or adjusted under 35 U.S.C. 154(b) by 0 days.

(21) Appl. No.: 13/155,411

(22) Filed: Jun. 8, 2011

(65) Prior Publication Data

US 2011/0263628 A1   Oct. 27, 2011

Related U.S. Application Data

(62) Division of application No. 11/572,761, filed as application No. PCT/EP2005/053616 on Jul. 25, 2005, now Pat. No. 8,008,302.

(60) Provisional application No. 60/591,111, filed on Jul. 26, 2004, provisional application No. 60/648,924, filed on Feb. 1, 2005.

(30) Foreign Application Priority Data

Jul. 26, 2004   (EP) .................................... 04103574
Jan. 31, 2005   (EP) .................................... 05100641

(51) Int. Cl.
*C07D 211/70*   (2006.01)
*C07D 405/06*   (2006.01)
*A61K 31/4418*  (2006.01)

(52) U.S. Cl. ...................... 514/354; 546/283.7; 546/328; 546/167; 546/257; 546/268.7; 546/269.4; 546/280.4; 546/248.1; 546/290; 546/310; 544/333; 544/405

(58) Field of Classification Search ........................ None
See application file for complete search history.

(56) References Cited

U.S. PATENT DOCUMENTS 7,786,121 B2    8/2010   Pain et al.
2002/0115863 A1 8/2002   Patel et al.

FOREIGN PATENT DOCUMENTS

| WO | WO 94/02447 | 2/1994 |
| WO | 95/33731 | 12/1995 |
| WO | WO 98/33788 | 8/1998 |
| WO | WO 01/83461 | 11/2001 |
| WO | 03/084941 | 10/2003 |

OTHER PUBLICATIONS

Birkedal-Hansen et al. Critical Reviews in Oral Biology and Medicine, vol. 4(2), p. 197-250 (1993).*
Vincenti et al. Arthritis & Rheumatism vol. 17, p. 1115-1124 (1994).*
Matrx Metalloproteinase, from Wikipedia, the free encyclopedia (8 pages), retrieved from the Internet on Dec. 17, 2009 at http://en.wikipedia.org/wiki/Matrix_metalloproteinase.*
Muroski et al. Curr.Pharm.Biotechnol. 9(1),p. 34-46 (2008).*
Belvisi, M.G. et al., "The role of matrix metalloproteinases (MMPs) in the patho-physiology of chronic obstructive pulmonary disease (COPD): a therapeutic role for inhibitors of MMPs?" Inflamm. Res., vol. 52, pp. 95-100, 2003.
Bulbena, O. et al., "Cytoprotective Activity in the Gastric Mucosa of Rats Exposed to Carbon Tetrachloride-Induced Liver Injury", Inflammation, vol. 21, No. 5, pp. 475-488, 1997.
Clark, Ian M. et al., "Metalloproteinases: their role in arthritis and potential as therapeutic targets", Expert Opin. Ther. Targets, vol. 7, No. 1, pp. 19-34, 2003.
Doherty, Terence M. et al., "Therapeutic developments in matrix metalloproteinase inhibition", Expert Opin. Ther. Patents, vol. 12, No. 5, pp. 665-707, 2002.
Fingleton, Barbara, "Matrix metalloproteinase inhibitors for cancer therapy: the current situation and future prospects", Expert Opin. Ther. Targets, vol. 7, No. 3, pp. 385-397, 2003.
Galis, Zorina S. et al., "Matrix Metalloproteinases in Vascular Remodeling and Atherogenesis, The Good, the Bad, and the ugly", Circulation Research, vol. 90, pp. 251-262, 2002.
Henrotin, Y et al., "The inhibition of metalloproteinases to treat osteoarthritis: reality and new perspectives", Expert Opin. Ther. Patents, vol. 12, No. 1, pp. 29-43, 2002.
Hooper, Nigel M. et al., "Membrane protein secretases", Biochem J., vol. 321, pp. 265-279, 1997.
Horstmann, Solveig et al., "Profiles of Matrix Metalloproteinases, Their inhibitors, and Laminin in Stroke Patients Influlence of Different Therapies", Stroke, vol. 34, pp. 2165-2172, 2003.
Tervahartiala, Ingman T. et al., "Matrix metalloproteinases and their inhibitors in gingival crevicular fluid and saliva of periodontitis patients", J. Clin. Periodontol, vol. 23, pp. 1127-1132, 1996.
Knight, C. Graham et al., "A novel coumarin-labelled peptide or sensitive continuous assays of the matrix metalloproteinases", Febs Letters, vol. 296, No. 3, pp. 263-266, Jan. 1992.
Krishna, Ganesh et al., "New therapies for chronic obstructive pulmonary disease", Expert Opin. Investig. Drugs, vol. 13, No. 3, pp. 255-267, 2004.
Leppert, David et al., "Matrix metalloproteinases: multifunctional effectors of inflammation in multiple sclerosis and bacterial meningitis", Brain Research Reviews, vol. 36, pp. 249-257, 2001.
Mahboobi, Siavosh et al., "214. Synthesis of Esters of 3-(2-Aminoethyl)-1H-indole-2-acetic Acid and 3-(2-Aminoethyl)-1H-indole-2-malonic Acid (=2-[3-(2-Aminoethyl)-1H-indol-2-yl]propanedioic Acid)", Helvetica Chi mica Acta, vol. 71, pp. 2034-2041, 1988.
Makrakis, E. et al., "Matrix metalloproteinase-9 and tissue inhibitor of metalloproteinsase-1 in plasma/serum and urine of women during term and threatened preterm labor: a clinical approach", The Journal of Maternal-Fetal and Neonatal Medicine, vol. 14, pp. 170-176, 2003.

(Continued)

*Primary Examiner* — Emily Bernhardt
(74) *Attorney, Agent, or Firm* — Oblon, Spivak, McClelland, Maier & Neustadt, L.L.P.

(57) ABSTRACT

The present invention is related to N-hydroxyamide derivatives of Formula (I) and use thereof in particular for the treatment and/or prophylaxis of autoimmune disorders, inflammatory diseases, cardiovascular diseases, neurodegenerative diseases, cancer, respiratory diseases and fibrosis, including multiple sclerosis, arthritis, emphysema, chronic obstructive pulmonary disease, liver and pulmonary fibrosis.

20 Claims, No Drawings

OTHER PUBLICATIONS

Malamas, Michael S. et al., Novel Benzofuran and Benzothiophene Biphenyls as Inhibitors of Protein Tyrosine Phosphatase 1 B with Antihyperglycemic Properties, J. Med. Chem., vol. 43, No. 7, pp. 1293-1310, 2000.

Opdenakker, Ghislain et al., "Functional roles and therapeutic targeting a gelatinase B and chemokines in multiple sclerosis", The Lancet Neurology, vol. 2, pp. 747-756, Dec. 2003.

Peterson, J. Thomas, "Matrix Metalloproteinase Inhibitor Development and the Remodeling of Drug Discovery", Heart Failure Reviews, vol. 9, pp. 63-79, 2004.

Seebach, Dieter, et al., "Diastereoselective α-Alkylation of β-Hydroxycarboxylic Esters Through Alkoxide Enolates: Diethyl (2S, 3R)-(+)-3-Allyl-2-Hydroxysuccinate from Diethyl (S)-(−)Malate", Organic Syntheses Collective vol. III, pp. 153-159, 1990.

Skiles, Jerry W. et al., "The Design, Structure, and Therapeutic Application of Matrix Metalloproteinase Inhibitors", Current Medicinal Chemistry, vol. 8, No. 4, pp. 425-474, 2001.

Skotnichi, Jerauld S. et al., "Design strategies for the identification of MMP-13 and TACE inhibitors", Current Opinion in Drug Discovery & Development, vol. 6, No. 5, pp. 742-759, 2003.

Visse, Robert et al., "Matrix Meatlloproteinases and Tissue Inhibitors of Metalloproteinases Structure, Function, and Biochemistry", Circulation Research, vol. 92, pp. 827-839, 2003.

Vos, Catharine M.P. et al., "Matrix metalloproteinase-12 is expressed in phagocytotic macrophages in active multiple sclerosis lesions", Journal of Neuroimmunology, vol. 138, pp. 106-114, 2003.

Wada, Carol K. et al., "Phenoxyphenyl Sulfone N-Formylhydrdoxylamines (Retrohydroxamates) as Potent, Selective, Orally Bioavailable Matrix Metalloproteinase Inhbitors", J. Med. Chem., vol. 45, No. 1, pp. 219-323, 2002.

* cited by examiner

N-HYDROXYAMIDE DERIVATIVES AND USE THEREOF

CROSS-REFERENCE TO RELATED APPLICATIONS

This application is a divisional of U.S. application Ser. No. 11/572,761 filed Jan. 26, 2007, now U.S. Pat. No. 8,008,302, which is a 371 of PCT/EP05/053616 filed Jul. 25, 2005 and claims the benefit of U.S. 60/591,111 filed Jul. 26, 2004, U.S. 60/648,924 filed Feb. 1, 2005, EP 04103574.2 filed Jul. 26, 2004 and EP 05100641.9 filed Jan. 31, 2005.

FIELD OF THE INVENTION

The present invention is related to N-hydroxyamide derivatives of Formula (I), pharmaceutical composition thereof, methods of preparation thereof and to their use for the treatment and/or prophylaxis of autoimmune disorders and/or inflammatory diseases, cardiovascular diseases, neurodegenerative diseases, cancer, respiratory diseases and fibrosis. Specifically, the present invention is related to N-hydroxyamide derivatives for the modulation, notably the inhibition of the activity or function of matrix metalloproteinases, especially gelatinases and metalloelastase.

BACKGROUND OF THE INVENTION

Metalloproteinases are a superfamily of proteinases (enzymes) named for their dependence on a metal ion (zinc) in the active site.

The matrix metalloproteinases (MMPs) form a metalloproteinase sub-family having as one of major biological function to catalyse the breakdown of connective tissue or extracellular matrix through their ability to hydrolyse various components of the tissue or matrix, such as collagens, gelatins, proteoglycans, fibronectins and elastin.

The matrix metalloproteinase family is further divided according to their function and substrates (Visse al., 2003, *Circ. Res.*, 92: 827-839) and comprises collagenases (MMP-1, MMP-8, MMP-13 and MMP-18), gelatinases (MMP-2 and MMP-9), stromelysins (MMP-3, MMP-10 and MMP-11), membrane-type MMPs (MT-MMP-1 to MT-MMP-6 and MMP-14, MMP-15, MMP-16, MMP-17, MMP-24 and MMP-25), matrilysins (MMP-7 and MMP-26) and other unclassified MMPs such as metalloelastase (MMP-12), enamelysin (MMP-20), epilysin (MMP-28), MMP-19, MMP-22 and MMP-23.

Apart from their role in degrading connective tissue, MMPs are involved in the biosynthesis of TNF-alpha and in the post-translational proteolysis processing, or shedding of biologically important membrane proteins (Hooper et al., 1997, *Biochem J.*, 321: 265-279). MMPs for example contribute to the local growth and spread of malignant lesions and therefore have been a target for anti-tumor drug development (Fingleton et al., 2003, *Expert Opin. Ther. Targets*, 7(3):385-397). Disorders such as inflammatory disorders like arthritis (Clark et al., 2003, *Expert. Opin. Ther Targets*, 7(1):19-34), respiratory disorders such as emphysema, atherosclerosis (Galis et al., 2002, *Circ. Res.*, 90:251-262), neurological disorders such as degenerative nervous system diseases, multiple sclerosis (Leppert et al., 2001, *Brain Res. Rev.*, 36:249-257), periodontitis (Ingman et al., 1996, *J. Clin. Periodontal.*, 23:127-1132), pre-term labor (Makratis et al., 2003, *J. Matern Fetal & Neonatal Medicine*, 14(3): 170-6) and wound healing have been demonstrated to be associated with MMPs expression and/or activity.

A wide variety of matrix metalloproteinase inhibitors (MMPIs) has been developed (Skiles et al., 2001, *Current Medicinal Chemistry*, 8, 425-474; Peterson, 2004, *Heart Failure Reviews*, 9, 63-79; Henrotin et al., 2002, *Expert Opin. Ther. Patents*, 12(1):29-43). However, many MMPIs exhibit a muscoskeletal syndrome (tendonitis, fibroplasias, mylasia, arthralasia) as a dose-limiting side effect. It has been proposed that inhibition of MMP-1 or MMP-14 may be responsible for these effects.

Therefore, there is an increasing need to develop matrix metalloproteinase inhibitors with a well-defined specificity profile.

Specific inhibitors, especially towards MMP-1, have been reported, including MMP-13 inhibitors (Stotnicki et al., 2003, *Current Opinion in Drug Discovery and Development*, 6(5): 742-759), MMP-12 inhibitors (WO 01/83461), MMP-2 and MMP-9 inhibitors (Wada et al., 2002, *J. Biol. Chem.* 45: 219-232).

The high relevance of the metalloproteinase pathway in some widely spread diseases stresses the need to develop inhibitors, including selective inhibitors of MMPs, especially of gelatinases such as MMP-2 and/or MMP-9 and/or MMP-12.

SUMMARY OF THE INVENTION

It is an object of the invention to provide substances which are suitable for the treatment and/or prevention of disorders related to autoimmune disorders and/or inflammatory diseases, cardiovascular diseases, neurodegenerative diseases, stroke, cancer, respiratory diseases, pre-term labor, endometriosis and fibrosis.

It is further an object of the present invention to provide substances which are suitable for the treatment and/or prevention of multiple sclerosis, arthritis, emphysema, chronic obstructive pulmonary disease and fibrosis.

It is notably an object of the present invention to provide chemical compounds which are able to modulate, especially inhibit the activity or function of matrix metalloproteinases, especially gelatinases and elastase in mammals, especially in humans.

It is furthermore an object of the present invention to provide a new category of pharmaceutical formulations for the treatment of and/or diseases mediated selected from autoimmune disorders, inflammatory diseases, cardiovascular diseases, neurodegenerative diseases, stroke, cancer, respiratory diseases pre-term labor, endometriosis and fibrosis.

It is furthermore an object of the present invention to provide processes for making chemical compounds according to the invention.

It is finally an object of the present invention to provide a method for the treatment and/or prevention of disorders selected from autoimmune disorders, inflammatory diseases, cardiovascular diseases, neurodegenerative diseases, stroke, cancer, respiratory diseases, pre-term labor, endometriosis and fibrosis.

In a first aspect, the invention provides N-hydroxyamide derivatives of Formula (I):

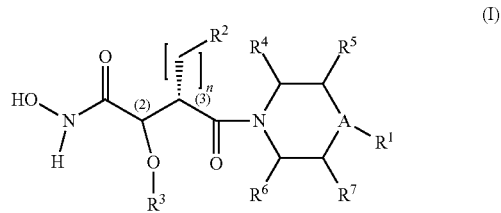

(I)

wherein A, $R^1$, $R^2$, $R^3$, $R^4$, $R^5$, $R^6$, $R^7$ and n are defined in the detailed description.

In a second aspect, the invention provides a compound according to Formula (I) for use as a medicament.

In a third aspect, the invention provides a use of a compound according to Formula (I) for the preparation of a pharmaceutical composition for the treatment of a disorder selected to from autoimmune disorders, inflammatory diseases, cardiovascular diseases, neurodegenerative diseases, stroke, cancer, respiratory diseases, pre-term labor, endometriosis and fibrosis.

In a fourth aspect, the invention provides a pharmaceutical composition comprising at least one a compound according to Formula (I) and a pharmaceutically acceptable carrier, diluent or excipient thereof.

In a fifth aspect, the invention provides a method of treatment comprising the administration of a compound according to Formula (I) in a patient in need thereof.

In a sixth aspect, the invention provides methods of synthesis of a compound according to Formula (I).

In a seventh aspect, the invention provides compounds according to Formula (IV):

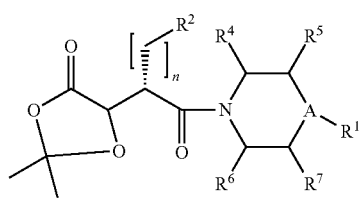

(IV)

wherein A, $R^1$, $R^2$, $R^4$, $R^5$, $R^6$, $R^7$ and n are defined in the detailed description.

In an eight aspect, the invention provides compounds according to Formula (V):

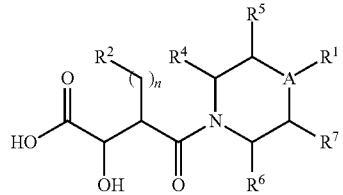

(V)

wherein A, $R^1$, $R^2$, $R^4$, $R^5$, $R^6$, $R^7$ and n are defined in the detailed description.

In a ninth aspect, the invention provides compounds according to Formula (III):

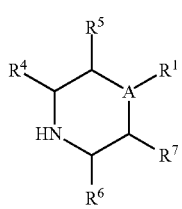

(III)

wherein A, $R^1$, $R^2$, $R^4$, $R^5$, $R^6$ and $R^7$ are defined in the detailed description.

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

The term "MMPs" refers to "matrix metalloproteinases". For recent reviews of MMPs, see Visse et al., 2003 above; Fingleton et al., 2003, above; Clark et al., 2003, above and Doherty et al., 2002, *Expert Opinion Therapeutic Patents* 12(5):665-707.

Illustrative but not limiting examples of such MMPs are:

Collagenases: usually associated with diseases linked to breakdown of collagen-based tissue e.g. rheumatoid arthritis and osteoarthritis:

MMP-1 (also known as collagenase 1, or fibroblast collagenase), substrates collagen I, collagen II, collagen III, gelatin, proteoglycans. Over-expression of this enzyme is believed to be associated with emphysema, with hyperkeratosis and atherosclerosis, overexpressed alone in papillary carcinoma.

MMP-8 (also known as collagenase 2, or neutrophil collagenase), substrates collagen I, collagen H, collagen HI, collagen V, collagen VII, collagen ix, gelatin over-expression of which can lead to non-healing chronic ulcers.

MMP-13 (also known as collagenase 3), substrates collagen I, collagen II, collagen III, collagen IV, collagen IX, collagen X, collagen XIV, fibronectin, gelatin, recently identified as being over-expressed alone in breast carcinoma and involved in rheumatoid arthritis.

Stromelysins:

MMP-3 (also known as stromelysin 1), substrates collagen III, collagen IV, collagen V, collagen IX, collagen X, larninin, nidogen, over-expression believed to be involved in atherosclerosis, aneurysm and restenosis.

Gelatinases—inhibition believed to exert a favorable effect on cancer, in particular invasion and metastasis.

MMP-2 (also known as gelatinase A, 72 kDa gelatinase, basement membrane collagenase, or proteoglycanase), substrates Collagen I, Collagen II, Collagen IV, Collagen V, Collagen VII, Collagen X, Collagen XI, collagen XIV, elastin, fibronectin, gelatin, nidogen, believed to be associated with tumor progression through specificity for type IV Collagen (high expression observed in solid tumors and believed to be associated with their ability to grow, invade, develop new blood vessels and metastasize) and to be involved in acute lung inflammation and in respiratory distress syndrome (Krishna et al., 2004, *Expert Opin. Invest. Drugs*, 13(3): 255-267).

MMP-9 (also known as gelatinase B, or 92 kDa gelatinase), substrates Collagen I, Collagen III, Collagen N, Collagen V, Collagen VII, collagen X, Collagen XIV, elastin, fibronectin, gelatin, nidogen. The above enzyme is believed to be associated with tumor progression through specificity for type IV Collagen, to be released by eosinophils in response to exogenous factors such as air pollutants, allergens and viruses, to be involved in the inflammatory response in multiple sclerosis (Opdenakker et al., 2003, *The Lancet Neurology*, 2, 747-756) and asthma and to be involved in acute lung inflammation, respiratory distress syndrome, chronic obstructive pulmonary disorder (COPD) and/or asthma (Krishna et al., 2004, above). MMP-9 is also thought to be involved in stroke (Horstmann et al., 2003, Stroke, 34(9): 2165-70).

Unclassified MMPs:

MMP-12 (also known as metalloelastase, human macrophage elastase, or HME), substrates fibronectin, laminin, believed to play a role in tumour growth inhibition and regulation of inflammation such as multiple sclerosis (Vos et al., 2003, *Journal of Neuroimmunology*, 138, 106-114) and to play a pathological role in emphysema, COPD (Belvisi et al., 2003, *Inflamm. Res.* 52: 95-100) and in atherosclerosis, aneurysm and restenosis.

The expression "MMP-associated disorder" refers to a disorder which is treatable according to the invention and that encompasses all disorders in which the expression and/or activity of at least one MMP needs to be decreased irrespective of the cause of such disorders. Such disorders include, for example, those caused by inappropriate extracellular matrix (ECM) degradation.

Illustrative but not limiting examples of such MMP-associated disorders are:

Cancer such as breast cancer and solid tumors; inflammatory disorders such as for example inflammatory bowel diseases and neuroinflammation such as multiple sclerosis; lung diseases such as chronic obstructive pulmonary disorder (COPD), emphysema, asthma, acute lung injury, and acute respiratory distress syndrome; dental diseases such as periodontal disease and gingivitis; joint and bone diseases such as osteoarthritis and rheumatoid arthritis; liver diseases such as liver fibrosis, cirrhosis and chronic liver disease; fibrotic diseases such as pulmonary fibrosis, pancreatitis, lupus, glomerulosclerosis, systemic sclerosis skin fibrosis, post-radiation fibrosis and cystic fibrosis; vascular pathologies such as aortic aneurysm, atherosclerosis, hypertension, cardiomyopathy and myocardial infarction; restenosis; opthalmological disorders such as diabetic retinopathy, dry eye syndrome, macula degeneration and corneal ulceration and degenerative diseases of the central nervous system such as amyotrophic lateral sclerosis.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroallyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including 3-phenylpropanoyl, benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl n-2-propenyl(allyl, —$CH_2CH$=$CH_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentyl propyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having an carboxy substituent, including 2-carboxyethyl and the like.

"Acyl" refers to the group —C(O)R where R includes "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including propionic acid ethyl ester and the like.

"Alkoxy" refers to the group —O—R where R includes "$C_1$-$C_6$-alkyl" or "aryl" or "hetero-aryl" or "aryl $C_1$-$C_6$-alkyl" or "heteroaryl $C_1$-$C_6$-alkyl". Preferred alkoxy groups include for to example, methoxy, ethoxy, phenoxy and the like.

"Alkoxy $C_1$-$C_6$-alkyl" refers to alkoxy groups having a $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-$C_6$-alkyl groups having an aminocarbonyl substituent, including 2-(dimethylaminocarbonyl)ethyl, N-ethyl acetamide, N,N-Diethyl-acetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cyclo allyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkyl", "cycloalkyl $C_1$-$C_6$-alkyl", "heterocycloalkyl $C_1$-$C_6$-alkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Amino $C_1$-$C_6$-alkyl" refers to $C_1$-$C_5$-alkyl groups having an amino substituent, including 2-(1-pyrrolidinyl)ethyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyl $C_1$-$C_6$-alkyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfonyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_5$-alkyl groups having a sulfanyl substituent, including 2-(ethylsulfanyl)ethyl and the like.

"Sulfonylamino" refers to a group —NRSO$_2$—R' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloallyl", "aryl", "heteroaryl", "aryl C$_1$-C$_6$-alkyl" or "heteroaryl C$_1$-C$_6$-alkyl", "aryl C$_2$-C$_6$-alkenyl", "heteroaryl C$_2$-C$_6$-alkenyl", "aryl C$_2$-C$_6$-alkynyl", "heteroaryl C$_2$-C$_6$-alkynyl", "cycloalkyl C$_1$-C$_6$-alkyl", "heterocycloalkyl C$_1$-C$_6$-alkyl".

"Sulfonylamino C$_1$-C$_6$-alkyl" refers to C$_1$-C$_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", to "heterocycloallyl", "aryl", "heteroaryl", "aryl C$_1$-C$_6$-alkyl" or "heteroaryl C$_1$-C$_6$-alkyl", "aryl C$_2$-C$_6$-alkenyl", "heteroaryl C$_2$-C$_6$-alkenyl", "aryl C$_2$-C$_6$-alkynyl", "heteroaryl C$_2$-C$_6$-alkynyl", "cycloalkyl C$_1$-C$_6$-alkyl", "heterocycloalkyl C$_1$-C$_6$-alkyl".

"Aminosulfonyl C$_1$-C$_6$-alkyl" refers to C$_1$-C$_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "C$_1$-C$_6$-alkyl", "C$_2$-C$_6$-alkenyl", "C$_2$-C$_6$-alkynyl", "cycloalkyl", "heterocycloalkyl", "aryl C$_1$-C$_6$-alkyl", "heteroaryl C$_1$-C$_6$-alkyl", "cycloalkyl C$_1$-C$_6$-alkyl", "heterocycloalkyl C$_1$-C$_6$-alkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

"Pharmaceutically active derivative" refers to any compound that upon administration to is the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. Such masking group may be a cyclic acetonide of Formula (I') wherein Y is a methyl or a hydrogen, and Y' is methyl, C$_2$-C$_4$ alkyl, phenyl, benzyl, optionally substituted with one to three substituents selected from C$_1$-C$_4$ alkyl, C$_1$-C$_4$ alkoxy, hydroxy, amino, methylamino, dimethylamino, chloro and fluoro; A, R$^1$, R$^2$, R$^4$, R$^5$, R$^6$, R$^7$ and n are defined in the detailed description.

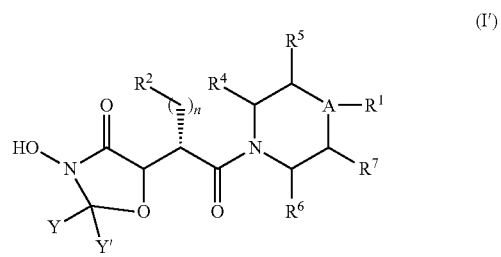

(I')

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as Rebif® (Serono), Avonex® (Biogen) or Betaferon® (Schering).

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably, IFN-beta is intended to mean recombinant Interferon beta-1a.

IFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass salts, functional derivatives, variants, analogs and active fragments thereof.

Rebif® (recombinant interferon-β) is the latest development in interferon therapy for multiple sclerosis (MS) and represents a significant advance in treatment. Rebif® is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI.

The dosing of IFN-β in the treatment of relapsing-remitting MS according to the invention depends on the type of IFN-β used.

In accordance with the present invention, where IFN is recombinant IFN-β1b produced in *E. coli*, commercially available under the trademark Betaseron®, it may preferably be administered sub-cutaneously every second day at a dosage of about of 250 to 300 µg or 8 MIU to 9.6 MIU per person.

In accordance with the present invention, where IFN is recombinant IFN-β1a, produced in Chinese Hamster Ovary cells (CHO cells), commercially available under the trademark Avonex®, it may preferably be administered intra-muscularly once a week at a dosage of about of 30 µg to 33 µg or 6 MIU to 6.6 MIU per person.

In accordance with the present invention, when IFN is recombinant IFN-β1a, produced in is Chinese Hamster Ovary cells (CHO cells), commercially available under the trademark Rebif®, it may preferably be administered sub-cutaneously three times a week (TIW) at a dosage of 22 to 44 µg or 6 MIU to 12 MIU per person.

Compounds according to the present invention also comprise pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

It has now been found that compounds of the present invention are modulators of the matrix metalloproteinases, especially gelatinases and elastase, including MMP-2 and/or MMP-9 and/or MMP-12. When the matrix metalloproteinase enzyme is inhibited by the compounds of the present invention, the inhibited MMP(s) is (are) unable to exert its enzymatic, biological and/or pharmacological effects. The compounds of the present invention are therefore useful in the treatment and prevention of autoimmune disorders and/or inflammatory diseases, cardiovascular diseases, pre-term labor, endometriosis, neurodegenerative diseases, stroke, cancer, respiratory diseases and fibrosis.

In one embodiment, the invention provides derivatives of Formula (I)

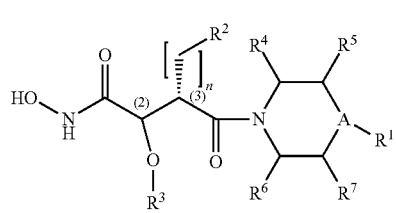

wherein:
A is selected from —C(B)— and N;
B is H or B forms a bond with either $R^5$ or $R^7$;
$R^1$ is selected from H; optionally substituted $C_1$-$C_6$ alkyl; optionally substituted $C_2$-$C_6$ alkenyl; optionally substituted $C_2$-$C_6$ alkynyl; optionally substituted $C_3$-$C_8$-cycloalkyl, including cyclohexyl; optionally substituted heterocycloalkyl; optionally substituted aryl, including optionally substituted phenyl such as phenyl, halophenyl such as fluorophenyl (e.g. 2-fluorophenyl, 4-fluorophenyl, 3-chlorophenyl), chlorophenyl (e.g. 2-chlorophenyl, 4-chlorophenyl), chloro-2-fluorophenyl and 2-fluoro-5-methoxyphenyl, cycloalkyl phenyl (e.g. 4-cyclohexylphenyl), alkyl phenyl (e.g. 4-propylphenyl, 4-tert-butylphenyl, 4-methyl phenyl), alkoxy phenyl such as methoxy phenyl (e.g. 4-methoxyphenyl, 3,4-dimethoxyphenyl, 3-methoxyphenyl, 3-fluoro-4-methoxy phenyl, 3-fluoro-4-(trifluoromethoxy)phenyl), butoxy phenyl (e.g. 4-tert-butoxyphenyl), propoxy phenyl (e.g. 4-isopropoxyphenyl, 3-fluoro-4-isopropoxy phenyl) and ethoxy phenyl (e.g. 4-ethoxyphenyl, 4-propoxy phenyl, 2,2,2-trifluoroethoxyphenyl), cyanophenyl (e.g. 2-cyanophenyl), trifluoromethyl phenyl (e.g. 4-trifluoromethyl phenyl), trifluoromethoxy phenyl (4-trifluoromethoxy)phenyl), sulfonyl phenyl (e.g. 4-(methylsulfonyl)phenyl, 4-(trifluoromethyl sulfonyl)), amino phenyl (e.g. 4-(dimethylamino)phenyl), biphenyl (e.g. 4-biphenyl, methoxy biphenyl, 4-fluorobiphenyl-4-yl, 4-methoxy biphenyl-4-yl, 4-bromobiphenyl-4-yl), oxazolyl phenyl (e.g. 1,3-oxazol-5-yl)phenyl and benzofuranyl phenyl (e.g. 1-benzofuran-3-yl)phenyl; optionally substituted heteroaryl, including optionally substituted pyridinyl, such as pyridinyl, methylpyridinyl (e.g. 4-methylpyridin-2-yl, 6-methylpyridin-2-yl), halo pyridinyl such as chloro pyridinyl (e.g. 6-chloropyridin-2-yl, 5-chloropyridin-2-yl, 3,5-dichloropyridin-4-yl) and bromo pyridinyl (5-bromopyridin-2-yl), trifluoromethyl pyridinyl (e.g. 3-(trifluoromethyl)pyridin-2-yl, 4-(trifluoromethyl)pyridin-2-yl, 5-(trifluoromethyl)pyridin-2-yl), cyano pyridinyl (e.g. 5-cyanopyridin-2-yl), phenyl pyridinyl (e.g. 5-phenyl pyridin-2-yl) and optionally substituted fused pyridinyl (e.g. 4-[6-methyl-2-(trifluoromethyl)quinolin-4-yl], 4-quinolin-3-yl, 4-quinolin-5-yl); including optionally substituted pyrazinyl (e.g. 4-pyrazin-2-yl); including optionally substituted thiadiazolyl such as such as 3-phenyl thiadiazolyl (e.g. 3-phenyl-1,2,4-thiadiazolyl-5-yl); including optionally substituted pyrimidinyl (e.g. 4-pyrimidinyl-2-yl, 5-fluoropyrimidin-2-yl); including optionally substituted oxadiazolyl such as 5-phenyl-1,2,4-oxadiazol-3-yl, 4-pyridin-4-yl-1,2,4-oxadiazol-3-yl, 5-(2-thienyl)-1,2,4-oxadiazol-3-yl and 5-(4-fluorophenyl)-1,3,4-oxadiazol-2-yl; including optionally substituted benzofuranyl (e.g. 1-benzofuran-5-yl); including optionally substituted thienyl (e.g. 5-chloro-2-thienyl) and including optionally substituted benzodioxolyl (e.g. 1,3-benzodioxol-5-yl, 2,2-difluoro-1,3-benzodioxol-5-yl); optionally substituted $C_3$-$C_8$-cycloalkyl $C_1$-$C_6$ alkyl; optionally substituted heterocycloalkyl $C_1$-$C_6$ alkyl, including 2-morpholin-4-ylethyl; optionally substituted heteroaryl $C_1$-$C_6$ alkyl, including 2-thienyl ethyl; optionally substituted amino, including optionally substituted phenyl amino (e.g. phenyl amino, 3-methoxyphenyl amino, 3-(dimethylamino)phenyl amino, 4-ethoxyphenyl amino), heteroaryl amino (e.g. 4-trifluoromethyl)pyrimidin-2-yl, 3-aminopyridin-2-yl) and optionally substituted alkoxy, including 4-(pyridin-2-yloxy), 4-(trifluoromethyl)phenoxy and 2-chlorophenoxy;

$R^2$ is selected from H; optionally substituted $C_1$-$C_6$ alkyl, including isopropyl; optionally substituted $C_2$-$C_6$ alkenyl; optionally substituted $C_2$-$C_6$ alkynyl; optionally substituted $C_3$-$C_8$-cycloalkyl, including cyclopentyl; optionally substituted heterocycloalkyl; optionally substituted alkoxy such as phenyl-methylene-oxy; optionally substituted aryl, including optionally substituted phenyl such as phenyl, ethoxy phenyl or trifluoromethoxy phenyl and optionally substituted heteroaryl;

$R^3$ is selected from H, optionally substituted $C_1$-$C_6$ alkyl, optionally substituted $C_2$-$C_6$ alkenyl and optionally substituted $C_2$-$C_6$ alkynyl;

$R^4$, $R^5$, $R^6$ and $R^7$ are independently selected from H; optionally substituted $C_1$-$C_6$ alkyl, including methyl; optionally substituted $C_2$-$C_6$ alkenyl; optionally substituted $C_2$-$C_6$ alkynyl; or $R^4$ and $R^7$ can form together a —$CH_2$— linkage for example to form with the piperazine ring a 2,5-diazabicyclo[2.2.1]hept-2-yl ring;

n is an integer selected from 1, 2, 3, 4, 5 and 6;

Carbons (2) and (3) are two chiral centers, wherein chiral center (2) has a configuration selected from "S" and "R" and wherein chiral center (3) has a "S" configuration.

The "S" configuration of chiral center (3) is such that the carbon bearing $R^2$ is assumed to have the lowest priority among the carbons in the Cahn-Ingold-Prelog chirality rule (see is Eliel et al., 1994, in "*Stereochemistry of Organic compounds*", Wiley Interscience).

Further chiral centers may be present in compounds according to Formula (I) and the invention intends to encompass as well optically active forms as enantiomers, diastereomers and its racemate forms, as well as pharmaceutically acceptable salts thereof of compounds according to Formula (I), the configuration of chiral center (3) being "S".

In a preferred embodiment, the invention Formula (I) having the following Formula Ia:

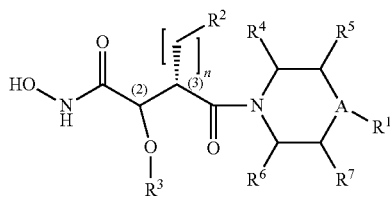

wherein A is selected from —CH and N; $R^1$, $R^2$, $R^3$, $R^4$, $R^5$, $R^6$, $R^7$ and n are defined in the detailed description.

In another preferred embodiment, the invention Formula (I) having the following Formula Ib:

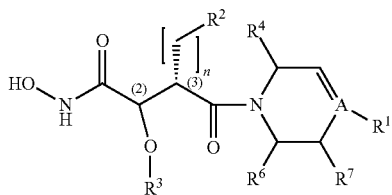

wherein A is a carbon atom and $R^1$, $R^2$, $R^3$, $R^4$, $R^6$, $R^7$ and n are defined in the detailed description.

In another preferred embodiment, the invention provides derivatives of Formula (I) wherein $R^1$ is selected from optionally substituted aryl and optionally substituted heteroaryl.

In another preferred embodiment, the invention provides derivatives of Formula (I) wherein $R^2$ is selected from H, optionally substituted $C_1$-$C_6$ alkyl, optionally substituted $C_2$-$C_6$ alkenyl and optionally substituted $C_2$-$C_6$ alkynyl.

In another preferred embodiment, the invention provides derivatives of Formula (I) wherein $R^2$ is selected from optionally substituted $C_3$-$C_8$-cycloalkyl, including cyclopentyl and optionally substituted heterocycloallyl.

In another preferred embodiment, the invention provides derivatives of Formula (I) wherein $R^2$ is optionally substituted alkoxy, such as phenyl-methylen-oxy.

In another preferred embodiment, the invention provides derivatives of Formula (I) wherein $R^2$ is aryl such as optionally substituted phenyl.

In another preferred embodiment, the invention provides derivatives of Formula (I) wherein $R^3$ is H.

In another preferred embodiment, the invention provides derivatives of Formula (I) wherein $R^4$, $R^5$ and $R^7$ are H.

In another preferred embodiment, the invention provides derivatives of Formula (I) wherein $R^6$ is selected from H and optionally substituted $C_1$-$C_6$ alkyl, including methyl.

In a further embodiment, the invention provides derivatives of Formula (I) wherein $R^6$ is H.

In a further embodiment, the invention provides derivatives of Formula (I) wherein $R^6$ is methyl.

In another preferred embodiment, the invention provides derivatives of Formula (I) wherein $R^4$ and $R^7$ can form together a —$CH_2$— linkage for example to form with the piperazine ring a 2,5-diazabicyclo[2.2.1]hept-2-yl ring.

In another preferred embodiment, the invention provides derivatives of Formula (I) wherein the configuration of the chiral carbons is (2S), (3S).

In another preferred embodiment, the invention provides derivatives of Formula (I) wherein the configuration of the chiral carbons is (2R), (3S).

In another preferred embodiment, the invention provides derivatives of Formula (I) wherein A is N.

In another preferred embodiment, the invention provides derivatives of Formula (I) wherein A is —CH.

In another preferred embodiment, the invention provides derivatives of Formula (I) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl, 4-chloro-2-fluorophenyl, 2-fluoro-5-methoxyphenyl, alkyl phenyl, methoxy phenyl, butoxy phenyl, propoxy phenyl, ethoxy phenyl, sulfonyl phenyl, amino phenyl, oxazolyl phenyl and benzofuran phenyl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; including optionally substituted benzofuranyl; including optionally substituted benzodioxolyl;

$R^2$ is selected from H; optionally substituted $C_1$-$C_6$ alkyl, including isopropyl; optionally substituted $C_2$-$C_6$ alkenyl, optionally substituted $C_2$-$C_6$ alkynyl and optionally substituted alkoxy including phenyl-methylene-oxy;

$R^3$, $R^4$, $R^5$ and $R^7$ are H; $R^6$ is selected from H and methyl; A is N; and n is an integer is selected from 1, 2, 3, 4, 5 and 6, preferably selected from 1, 2 and 3.

In another preferred embodiment, the invention provides derivatives of Formula (I) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl and 4-chloro-2-fluorophenyl, 2-fluoro-5-methoxyphenyl, alkyl phenyl, methoxy phenyl, butoxy phenyl, propoxy phenyl, ethoxy phenyl, sulfonyl phenyl, amino phenyl, oxazolyl phenyl and benzofuran phenyl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; including substituted benzofuranyl; including optionally substituted benzodioxolyl;

$R^2$ is selected from H; optionally substituted $C_1$-$C_6$ alkyl, including isopropyl; optionally substituted $C_2$-$C_6$ alkenyl, optionally substituted $C_2$-$C_6$ alkynyl and optionally substituted alkoxy including phenyl-methylene-oxy;

$R^3$, $R^4$, $R^5$ and $R^7$ are H; $R^6$ is selected from H and methyl; A is —CH; and n is an integer selected from 1, 2, 3, 4, 5 and 6, preferably selected from 1, 2 and 3.

In another preferred embodiment, the invention provides derivatives of Formula (II) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl and 4-chloro-2-fluorophenyl, 2-fluoro-5-methoxyphenyl, alkyl phenyl, methoxy phenyl, butoxy phenyl, propoxy phenyl, ethoxy phenyl, sulfonyl phenyl, amino phenyl, oxazolyl phenyl and benzofuran phenyl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; substituted benzofuranyl; including optionally substituted benzodioxolyl;

$R^2$ is selected from H; optionally substituted $C_1$-$C_6$ alkyl, including isopropyl; optionally substituted $C_2$-$C_6$ alkenyl, optionally substituted $C_2$-$C_6$ alkynyl and optionally substituted alkoxy including phenyl-methylene-oxy;

$R^3$ and $R^5$ are H; $R^6$ is selected from H and methyl; $R^4$ and $R^7$ can form together a —$CH_2$— linkage; A is N; and n is an integer selected from 1, 2, 3, 4, 5 and 6, preferably selected from 1, 2 and 3.

In another preferred embodiment, the invention provides derivatives of Formula (I) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl and 4-chloro-2-fluorophenyl, 2-fluoro-5-methoxyphenyl, alkyl phenyl, methoxy phenyl, butoxy phenyl, propoxy phenyl, ethoxy phenyl, sulfonyl phenyl, amino phenyl, oxazolyl phenyl and benzofuran phenyl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; including optionally substituted benzofuranyl; including optionally substituted to benzodioxolyl;

$R^2$ is optionally substituted aryl, including optionally substituted phenyl, such as ethoxy phenyl;

$R^3$, $R^4$, $R^5$ and $R^7$ are H; $R^6$ is selected from H and methyl; A is N; and n is an integer selected from 1, 2, 3, 4, 5 and 6, preferably selected from 1, 2 and 3.

In a further preferred embodiment, the invention provides derivatives of Formula (I) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl and 4-chloro-2-fluorophenyl, 2-fluoro-5-methoxyphenyl, alkyl phenyl, methoxy phenyl, butoxy phenyl, propoxy phenyl, ethoxy phenyl, sulfonyl phenyl, amino phenyl, oxazolyl phenyl and benzofuran phenyl (e.g. 1-benzofuran-3-yl)phenyl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; including optionally substituted benzofuranyl; including optionally substituted benzodioxolyl;

$R^2$ is optionally substituted phenyl, such as ethoxy phenyl;

$R^3$, $R^4$, $R^5$ and $R^7$ are H; $R^6$ is selected from H and methyl; A is N; and n is 3.

In another preferred embodiment, the invention provides derivatives of Formula (Ib) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl and 4-chloro-2-fluorophenyl, 2-fluoro-5-methoxyphenyl; alkyl phenyl, methoxy phenyl, butoxy phenyl, propoxy phenyl, ethoxy phenyl, sulfonyl phenyl, amino phenyl, oxazolyl phenyl and benzofuran phenyl (e.g. 1-benzofuran-3-yl)phenyl; optionally substituted heteroaryl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; including optionally substituted benzofuranyl; including optionally substituted benzodioxolyl;

$R^2$ is selected from H; optionally substituted $C_1$-$C_6$ alkyl, including isopropyl; optionally substituted $C_2$-$C_6$ alkenyl, optionally substituted $C_2$-$C_6$ alkynyl, optionally substituted awl, optionally substituted heteroaryl and optionally substituted alkoxy including phenyl-methylene-oxy;

$R^3$, $R^4$ and $R^6$ are H;

n is an integer selected from 1, 2, 3, 4, 5 and 6, preferably selected from 1, 2 and 3.

Compounds of the present invention include in particular those selected from the following group:

(2S,3S)-N,2-dihydroxy-5-methyl-3-{[4-(2-pyridinyl)-1-piperazinyl]carbonyl}hexanamide;

(2S,3S)-N,2-dihydroxy-5-methyl-3-{[4-(3-phenyl-1,2,4-thiadiazol-5-yl)-1-piperazinyl]carbonyl}hexanamide;

(2S,3S)-N,2-dihydroxy-5-methyl-3-({(2R)-2-methyl-4-[4-(trifluoromethyl)pyridin-2-yl]piperazin-1-yl}carbonyl) hexanamide;

(2S,3S)-N,2-dihydroxy-5-methyl-3-{[(2R)-2-methyl-4-(2-pyridinyl)piperazinyl]carbonyl}hexanamide;

(2S,3S)-N,2-dihydroxy-5-methyl-3-{[(2S)-2-methyl-4-pyridin-2-ylpiperazin-1-yl]carbonyl}hexanamide;

(2S,3S)-6-(4-ethoxyphenyl)-N,2-dihydroxy-3-{[(2R)-2-methyl-4-pyridin-2-ylpiperazin-1-yl]carbonyl}hexanamide;

(2S,3S)-6-(4-ethoxyphenyl)-N,2-dihydroxy-3-{[(2S)-2-methyl-4-(2-pyridinyl)piperazinyl]carbonyl}hexanamide;

(2S,3S)-6-(4-ethoxyphenyl)-N,2-dihydroxy-3-{[(2R)-2-methyl-4-pyrimidin-2-ylpiperazin-1-yl]carbonyl}hexanamide;

(2S,3S)-6-(4-ethoxyphenyl)-3-{[(2R)-4-(2-fluorophenyl)-2-methylpiperazin-1-yl]carbonyl}-N,2-dihydroxyhexanamide;

(2S,3S)-N,2-dihydroxy-5-methyl-3-{[(2R)-2-methyl-4-pyrimidin-2-ylpiperazin-1-yl]carbonyl}hexanamide;

(2S,3S)-N,2-dihydroxy-5-methyl-3-{[(2S)-2-methyl-4-(4-methylpyridin-2-yl)piperazin-1-yl]carbonyl}hexanamide;

(2S,3S)-3-{[(2R)-4-(2-fluoro-5-methoxyphenyl)-2-methylpiperazin-1-yl]carbonyl}-N,2-dihydroxy-5-methylhexanamide;

(2S,3S)-3-{[(2R)-4-(2-fluorophenyl)-2-methylpiperazin-1-yl]carbonyl}-N,2-dihydroxy-5-methylhexanamide;

(2R,3S)-N,2-dihydroxy-3-{[4-(4-methoxyphenyl)piperazin-1-yl]carbonyl}-5-methyl hexanamide;

(2S,3S)-3-{[(2R)-4-(4-chloro-2-fluorophenyl)-2-methylpiperazin-1-yl]carbonyl}-N,2-dihydroxy-5-methylhexanamide;

(2S,3S)-3-{[(2R)-4-(5-chloropyridin-2-yl)-2-methylpiperazin-1-yl]carbonyl}-N,2-dihydroxy-5-methylhexanamide;

(2R,3S)-3-{[4-(4-fluorophenyl)piperazin-1-yl]carbonyl}-N,2-dihydroxy-5-methyl hexanamide;

(2R,3S)-3-{[(1S,4S)-5-(4-fluorophenyl)-2,5-diazabicyclo[2.2.1]kept-2-yl]carbonyl}-N,2-dihydroxy-5-methylhexanamide;

(2R,3S)-N,2-dihydroxy-5-methyl-3-[(4-pyridin-2-ylpiperazin-1-yl)carbonyl]hexanamide;

(2R,3S)-N,2-dihydroxy-5-methyl-3-({4-[4-(trifluoromethyl)phenyl]piperazin-1-yl}carbonyl)hexanamide;

(2R,3S)-3-{[4-(2-fluorophenyl)piperazin-1-yl]carbonyl}-N,2-dihydroxy-5-methyl hexanamide;

(2R,3S)-N,2-dihydroxy-5-methyl-3-[(4-pyrimidin-2-ylpiperazin-1-yl)carbonyl]hexanamide;

(2S,3S)-N,2-dihydroxy-5-methyl-3-({(2R)-2-methyl-4-[4-(trifluoromethoxy)phenyl]piperazin-1-yl}carbonyl)hexanamide;

(2S,3S)-3-{(2R)-4-biphenyl-[4-yl-2-methylpiperazin-1-yl]carbonyl}-N,2-dihydroxy-5-methylhexanamide;

(2S,3S)-3-{[(2S)-4-(2-fluorophenyl)-2-methylpiperazin-1-yl]carbonyl}-N,2-dihydroxy-5-methylhexanamide;

(2S,3S)-3-{[(2R)-4-(3-chlorophenyl)-2-methylpiperazin-1-yl]carbonyl}-N,2-dihydroxy-5-methylhexanamide;

(2R,3S)-N,2-dihydroxy-5-methyl-3-{[4(5-phenyl-1,2,4-oxadiazol-3-yl)piperazin-1-yl]carbonyl}hexanamide;

(2S,3S)-N,2-dihydroxy-5-methyl-3-{[(2R)-2-methyl-4-(5-phenylpyridin-2-yl)piperazin-1-yl]carbonyl}hexanamide;

3-[(4-biphenyl-4-ylpiperazin-1-yl)carbonyl]-3,4-dideoxy-1-(hydroxyamino)-5-O-(phenylmethyl)-L-threo-pentose;

(2R,3S)-3-({4-[5-(4-fluorophenyl)-1,3,4-oxadiazol-2-yl]piperidin-1-yl}carbonyl)-N,2-dihydroxy-5-methylhexanamide;

(2R,3S)-3-{[4-(4-fluorophenyl)-3,6-dihydropyridin-1(2H)-yl]carbonyl}-N,2-dihydroxy-5-methylhexanamide;

(2R,3S)-N,2-dihydroxy-5-methyl-3-[(4-phenyl-3,6-dihydropyridin-1(2H)-yl)carbonyl]hexanamide;

(2R,3S)-N,2-dihydroxy-5-methyl-3-{[4-(5-pyridin-4-yl-1,2,4-oxadiazol-3-yl)piperazin-1-yl]carbonyl}hexanamide;

(2R,3S)-3-{[4-(4-chlorophenyl)-3,6-dihydropyridin-1(2H)-yl]carbonyl}-N,2-dihydroxy-5-methylhexanamide;

(2S,3S)-3-{[4-(2-fluorophenyl)piperazin-1-yl]carbonyl}-N,2-dihydroxy-5-methyl hexanamide;

(2R,3S)-N,2-dihydroxy-5-methyl-3-({4-[5-(2-thienyl)-1,2,4-oxadiazol-3-yl]piperazin-1-yl}carbonyl)hexanamide;

(2R,3S)-3-{[(2R)-4-(5-chloropyridin-2-yl)-2-methylpiperazin-1-yl]carbonyl}-N,2-dihydroxy-5-methylhexanamide;

(2R,3S)-3-{[4-(5-chloropyridin-2-yl)piperazin-1-yl]carbonyl}-N,2-dihydroxy-5-methyl hexanamide;

(2R,3S)-3-{[4-(5-bromopyridin-2-yl)piperazin-1-yl]carbonyl}-N,2-dihydroxy-5-methyl hexanamide;

(2S,3S)-3-{[(2R)-4-(4-chlorophenyl)-2-methylpiperazin-1-yl]carbonyl}-N,2-dihydroxy-5-methylhexanamide;

(2S,3S)-N,2-dihydroxy-5-methyl-3-({(2R)-2-methyl-4-[5-(trifluoromethyl)pyridin-2-yl]piperazin-1-yl}carbonyl)hexanamide;

(2R,3S)-3-benzyl-N,2-dihydroxy-4-oxo-4-{4-[4-(trifluoromethoxy)phenyl]piperazin-1-yl}butanamide;

(2S,3S)-3-benzyl-N,2-dihydroxy-4-{(2R)-2-methyl-4-[4-(trifluoromethoxy)phenyl]piperazin-1-yl}-4-oxobutanamide;

(2R,3S)-N,2-dihydroxy-3-methyl-4-oxo-4-{4-[4-(trifluoromethoxy)phenyl]piperazin-1-yl}butanamide;

(2S)-N,2-dihydroxy-3-methyl-4-{(2R)-2-methyl-4-[4-(trifluoromethoxy)phenyl]piperazin-1-yl}-4-oxobutanamide;

(2S,3S)-3-{[(2R)-4-(4'-fluorobiphenyl-4-yl)-2-methylpiperazin-1-yl]carbonyl}-N,2-dihydroxy-5-methylhexanamide;

(2S,3S)-3-{[(2R)-4-(4-ethoxyphenyl)-2-methylpiperazin-1-yl]carbonyl}-N,2-dihydroxy-5-methylhexanamide;

(2S,3S)-3-{[(2R)-4-(3,4-dimethoxyphenyl)-2-methylpiperazin-1-yl]carbonyl}-N,2-dihydroxy-5-methylhexanamide;

(2S,3S)-N,2-dihydroxy-5-methyl-3-({(2R)-2-methyl-4-[4-(methylsulfonyl)phenyl]piperazin-1-yl}carbonyl)hexanamide;

(2S,3S)-N,2-dihydroxy-3-{[(2R)-4-(6-methoxy-2-naphthyl)-2-methylpiperazin-1-yl]carbonyl}-5-methylhexanamide;

(2S,3S)-3-({(2R)-4-[4-(1-benzofuran-3-yl)phenyl]-2-methylpiperazin-1-yl}carbonyl)-N,2-dihydroxy-5-methylhexanamide;

(2S,3S)-N,2-dihydroxy-5-methyl-3-{[(2R)-2-methyl-4-(4-propoxyphenyl)piperazin-1-yl]carbonyl}hexanamide;

(2S,3S)-N,2-dihydroxy-5-methyl-3-({(2R)-2-methyl-4-[4-(trifluoromethyl)phenyl]piperazin-1-yl}carbonyl)hexanamide;

(2S,3S)-3-{[(2R)-4-(4-tert-butylphenyl)-2-methylpiperazin-1-yl]carbonyl}-N,2-dihydroxy-5-methylhexanamide;

(2S,3S)-3-{[(2R)-4-(5-fluoropyrimidin-2-yl)-2-methylpiperazin-1-yl]carbonyl}-N,2-dihydroxy-5-methylhexanamide;

(2S,3S)-N,2-dihydroxy-5-methyl-3-{[(2R)-2-methyl-4-(4-propylphenyl)piperazin-1-yl]carbonyl}hexanamide;

(2S,3S)-3-(cyclopentylmethyl)-N,2-dihydroxy-4-{(2R)-2-methyl-4-[4-(trifluoromethoxy)phenyl]piperazin-1-yl}-4-oxobutanamide;

(2S,3S)-3-{[(2R)-4-(2,3-dihydro-1-benzofuran-5-yl)-2-methylpiperazin-1-yl]carbonyl}-N,2-dihydroxy-5-methylhexanamide;

(2S,3S)-3-[(2R)-4-(1,3-benzodioxol-5-yl)-2-methylpiperazin-1-yl]carbonyl)-N,2-dihydroxy-5-methylhexanamide;

(2S,3S)-N,2-dihydroxy-3-{[(2R)-4-(4-methoxyphenyl)-2-methylpiperazin-1-yl]carbonyl}-5-methylhexanamide;

(2S,3S)-N,2-dihydroxy-5-methyl-3-[((2R)-2-methyl-4-{4-[(trifluoromethyl)sulfonyl]phenyl}piperazin-1-yl)carbonyl]hexanamide;

(2S,3S)-N,2-dihydroxy-3-{[(2R)-4-(4'-methoxybiphenyl-4-yl)-2-methylpiperazin-1-yl]carbonyl}-5-methylhexanamide;

(2S,3S)-3-{[(2R)-4-(4-cyclohexylphenyl)-2-methylpiperazin-1-yl]carbonyl}-N,2-dihydroxy-5-methylhexanamide;
(2S,3S)-3-{[(2R)-4-(1-benzofuran-5-yl)-2-methylpiperazin-1-yl]carbonyl}-N,2-dihydroxy-5-methylhexanamide;
(2S,3S)-3-{[(2R)-4-(2,2-difluoro-1,3-benzodioxol-5-yl)-2-methylpiperazin-1-yl]carbonyl}-N,2-dihydroxy-5-methylhexanamide;
(2S,3S)-3-{[(2R)-4-(3-fluoro-4-methoxyphenyl)-2-methylpiperazin-1-yl]carbonyl}-N,2-dihydroxy-5-methylhexanamide;
(2S,3S)-3-{[(2R)-4-(3-fluoro-4-isopropoxyphenyl)-2-methylpiperazin-1-yl]carbonyl}-N,2-dihydroxy-5-methylhexanamide;
(2S,3S)-3-({(2R)-4-[3-fluoro-4-(trifluoromethoxy)phenyl]-2-methyl piperazin-1-yl}carbonyl)-N,2-dihydroxy-5-methylhexanamide;
(2S,3S)-N,2-dihydroxy-5-methyl-3-{[(2R)-2-methyl-4-quinolin-3-yl-piperazin-1-yl]carbonyl}hexanamide;
(2S,3S)-N,2-dihydroxy-5-methyl-3-{[(2R)-2-methyl-4-(4-methyl phenyl)piperazin-1-yl]carbonyl}hexanamide;
(2S,3S)-3-{[(2R)-4-(5-chloro-2-thienyl)-2-methylpiperazin-1-yl]carbonyl}-N,2-dihydroxy-5-methylhexanamide;
(2S,3S)-N,2-dihydroxy-3-{[(2R)-4-(3-methoxyphenyl)-2-methyl piperazin-1-yl]carbonyl}-5-methylhexanamide;
(2S,3S)-3-{[(2R)-4-(4'-bromobiphenyl-4-yl)-2-methylpiperazin-1-yl]carbonyl}-N,2-dihydroxy-5-methylhexanamide;
(2S,3S)-N,2-dihydroxy-5-methyl-3-({(2R)-2-methyl-4-[4-(2,2,2-trifluoro ethoxy)phenyl]piperazin-1-yl}carbonyl) hexanamide;
(2S,3S)-3-{[(2R)-4-(4-tert-butoxyphenyl)-2-methylpiperazin-1-yl]carbonyl}-N,2-dihydroxy-5-methylhexanamide;
(2S,3S)-N,2-dihydroxy-3-{[(2R)-4-(4-isopropoxyphenyl)-2-methyl piperazin-1-yl]carbonyl}-5-methylhexanamide;
(2S,3S)-N,2-dihydroxy-5-methyl-3-{[(2R)-2-methyl-4-quinolin-6-yl piperazin-1-yl]carbonyl}hexanamide;
(2S,3S)-3-({(2R)-4-[3,5-bis(trifluoromethyl)phenyl]-2-methylpiperazin-1-yl}carbonyl)-N,2-dihydroxy-5-methylhexanamide;
(2S,3S)-N,2-dihydroxy-5-methyl-3-({(2R)-2-methyl-4-[4-(1,3-oxazol-5-yl)phenyl]piperazin-1-yl}carbonyl)hexanamide;
(2S,3S)-3-({(2R)-4-[4-(dimethylamino)phenyl]-2-methylpiperazin-1-yl}carbonyl)-N,2-dihydroxy-5-methylhexanamide.

In another embodiment of the invention, are provided N-hydroxyamide derivatives according to Formula (I) for use as a medicament.

In another embodiment of the invention, is provided a pharmaceutical composition comprising at least one N-hydroxyamide derivative according to the invention and a pharmaceutically acceptable carrier, diluent or excipient thereof.

In another embodiment of the invention, is provided a use of N-hydroxyamide derivatives according to Formula (I) for the preparation of a medicament for the prophylaxis and/or treatment of a disorder selected from autoimmune disorders, inflammatory diseases, stroke, cardiovascular diseases, neurodegenerative diseases, cancer, respiratory diseases and fibrosis, including multiple sclerosis, inflammatory bowel disease, arthritis, asthma, emphysema, pre-term labor, endometriosis, chronic obstructive pulmonary disease, liver and pulmonary, pancreatic fibrosis, skin fibrosis and liver fibrosis.

In an further embodiment of the invention, is provided a use of N-hydroxyamide derivatives according to Formula (I) for the preparation of a medicament for the prophylaxis and/or treatment of a disorder selected from inflammatory bowel disease, multiple sclerosis and rheumatoid arthritis.

In another further embodiment of the invention, is provided a use of N-hydroxyamide derivatives according to Formula (I) for the preparation of a medicament for the prophylaxis and/or treatment of a disorder selected from asthma, emphysema and chronic obstructive pulmonary disease.

In another further embodiment of the invention, is provided a use of N-hydroxyamide derivatives according to Formula (I) for the preparation of a medicament for the prophylaxis and/or treatment of a disorder selected from pulmonary, pancreatic, skin and liver fibrosis.

In another further embodiment of the invention, is provided a use of N-hydroxyamide to derivatives according to Formula (I) for the preparation of a medicament for the prophylaxis and/or treatment of a disorder wherein the disorder is a cancer.

In another embodiment of the invention, is provided a use of N-hydroxyamide derivatives according to Formula (I) for the modulation, in particular for the inhibition, of the matrix metalloproteinase activity. Particularly, is provided a use according to the invention wherein said matrix metalloproteinase is selected from MMP-2, MMP-9 and MMP-12. Preferably, compounds according to the invention are selective inhibitors of metalloproteineases selected from MMP-2, MMP-9 and/or MMP-12 over MMP-1.

In another embodiment, the invention provides a method of treatment and/or prophylaxis of a disease comprising the administration of a compound according to Formula (I), in a patient in need thereof and wherein the disease is selected from autoimmune disorders, inflammatory diseases, cardiovascular diseases, neurodegenerative diseases, stroke, cancer, respiratory diseases and fibrosis, including multiple sclerosis, arthritis, asthma, emphysema, pre-term labor, endometriosis, chronic obstructive pulmonary disease (COPD), liver, skin and pulmonary fibrosis.

In another embodiment, the invention provides a process for the preparation of a N-hydroxyamide derivative according to the invention, comprising the step of reacting a compound of Formula (IV) with a derivative $H_2N$—O—$R^8$:

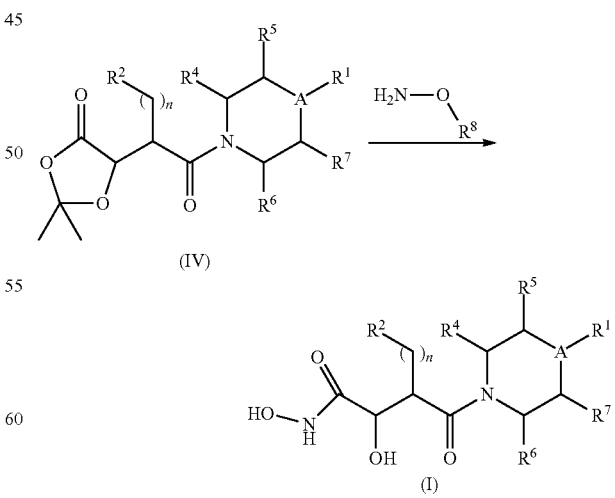

wherein A, $R^1$, $R^2$, $R^4$, $R^5$, $R^6$, $R^7$ and n are defined above and $R^8$ is selected from H and a protective group such as t-butyl, benzyl, trialkylsilyl, tetrahydropyranyl.

In another embodiment, the invention provides a process for the preparation of a N-hydroxyamide derivative according to the invention, comprising the step of reacting a to compound of Formula (V) with a hydroxylamine or with a protected hydroxylamine H₂NO—

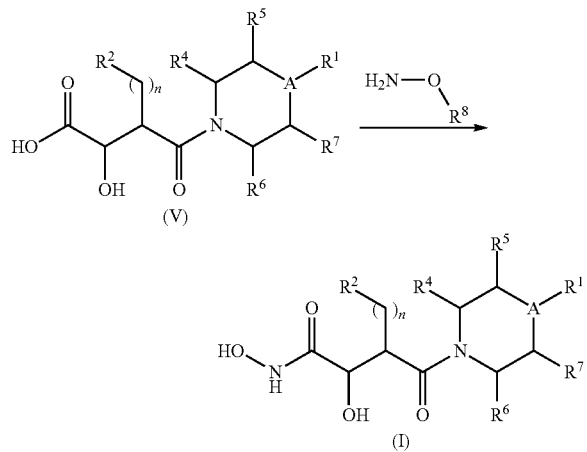

wherein A, R¹, R², R⁴, R⁵, R⁶, R⁷ and n are defined above and R⁸ is selected from H and a protective group such as t-butyl, benzyl, trialkylsilyl, tetrahydropyranyl.

In a further embodiment, the invention provides a process for the preparation of a N-hydroxyamide derivative according to the invention, optionally further comprising a deprotection step (R⁸ removal, when R⁸ is not H).

In another embodiment, the invention provides a process for the preparation of a N-hydroxyamide derivative according to the invention, comprising the step of coupling a dioxolane-protected di-carboxylic acid of Formula (II) with an amine of Formula (III) to form the intermediate of Formula (IV) in presence of a coupling such as DIC, EDC, TBTU, DCC, HATU, PyBOP®, Isobutyl chloroformate or 1-methyl-2-chloropyridinium iodide

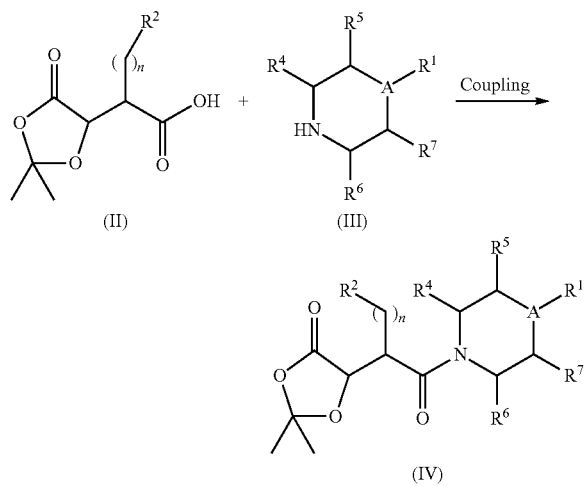

wherein A, R¹, R², R⁴, R⁵, R⁶, R⁷ and n are as defined above and wherein the compounds according to Formula (III) are selected from the group below:
(3R)-1-(2-fluorophenyl)-3-methylpiperazine;
(3S)-1-(2-Fluorophenyl)-3-methylpiperazine;
(3R)-3-methyl-1-[4-(trifluoromethyl)pyridin-2-yl]piperazine;
5-fluoro-2-[(3R)-3-methylpiperazin-1-yl]pyrimidine;
(3R)-3-methyl-1-[5-(trifluoromethyl)pyridin-2-yl]piperazine;
(3R)-3-methyl-1-(4-propylphenyl)piperazine;
(3R)-1-(6-methoxy-2-naphthyl)-3-methylpiperazine;
(3R)-1-[4-(1-benzofuran-3-yl)phenyl]-3-methylpiperazine;
(3R)-3-methyl-1-(4-propoxyphenyl)piperazine;
(3R)-1-(4'-fluorobiphenyl-4-yl)-3-methylpiperazine;
(3R)-3-methyl-1-[4-(trifluoromethoxy)phenyl]piperazine;
(3R)-1-(3,4-dimethoxyphenyl)-3-methylpiperazine;
(3R)-3-methyl-1-[4-(methylsulfonyl)phenyl]piperazine;
(3R)-1-(2,3-dihydro-1-benzofuran-5-yl)-3-methylpiperazine;
(3R)-1-(1,3-benzodioxol-5-yl)-3-methylpiperazine;
(3R)-3-methyl-1-{4-[(trifluoromethyl)sulfonyl]phenyl}piperazine;
(3R)-1-(4-tert-butylphenyl)-3-methylpiperazine;
(3R)-1-(4-ethoxyphenyl)-3-methylpiperazine;
(3S)-3-methyl-1-(4-methylpyridin-2-yl)piperazine;
(3R)-1-(2-fluoro-5-methoxyphenyl)-3-methylpiperazine;
(3R)-1-(4-chloro-2-fluorophenyl)-3-methylpiperazine;
(3R)-1-(5-chloro pyridin-2-yl)-3-methylpiperazine;
(3R)-1-biphenyl-4-yl-3-methyl-piperazine;
(3R)-3-methyl-1-(5-phenyl-pyridin-2-yl)piperazine;
(3R)-1-(4'-methoxybiphenyl-4-yl)-3-methylpiperazine;
(3R)-1-(4-cyclohexylphenyl)-3-methylpiperazine;
(3R)-1-(1-benzofuran-5-yl)-3-methylpiperazine;
(3R)-1-(2,2-difluoro-1,3-benzodioxol-5-yl)-3-methylpiperazine;
(3R)-1-(3-fluoro-4-methoxyphenyl)-3-methylpiperazine;
(3R)-1-(3-fluoro-4-isopropoxyphenyl)-3-methylpiperazine;
(3R)-1-[3-fluoro-4-(trifluoromethoxy)phenyl]-3-methylpiperazine;
3-[(3R)-3-methylpiperazin-1-yl]quinoline.

In another embodiment, the invention provides a compound according to Formula (IV):

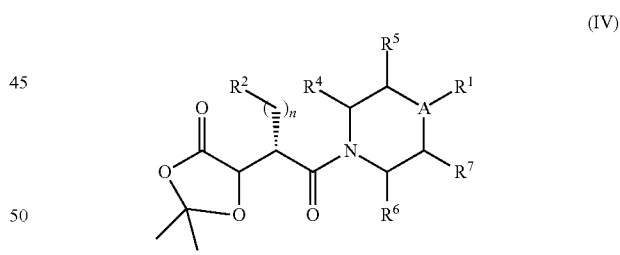

wherein A, R¹, R², R⁴, R⁵, R⁶, R⁷ and n are as defined above.

In a further embodiment, the invention provides a compound according to Formula (IV) selected from the group:
(5S)-2,2-dimethyl-5-((1S)-3-methyl-1-{[4-(2-pyridinyl)-1-piperazinyl]carbonyl}butyl)-1,3-dioxolan-4-one;
(5S)-2,2-dimethyl-5-((1S)-3-methyl-1-{[4-(3-phenyl-1,2,4-thiadiazol-5-yl)-1-piperazinyl]carbonyl}butyl)-1,3-dioxolan-4-one;
(5S)-2,2-dimethyl-5-[(1S)-3-methyl-1({(2R)-2-methyl-4-[4-(trifluoro methyl)pyridin-2-yl]piperazin-1-yl}carbonyl)butyl]-1,3-dioxolan-4-one;
(5S)-2,2-dimethyl-5-((1S)-3-methyl-1-{[(2R)-2-methyl-4-(2-pyridinyl)piperazinyl]carbonyl}butyl)-1,3-dioxolan-4-one;

(5S)-2,2-dimethyl-5-((1S)-3-methyl-1-{[(2S)-2-methyl-4-pyridin-2-ylpiperazin-1-yl]carbonyl}butyl)-1,3-dioxolan-4-one;

(5S)-5-((1S)-4-(4-ethoxyphenyl)-1-{[(2R)-2-methyl-4-(2-pyridinyl)piperazinyl]carbonyl}butyl)-2,2-dimethyl-1,3-dioxolan-4-one;

(5S)-5-((1S)-4-(4-ethoxyphenyl)-1-{[(2S)-2-methyl-4-(2-pyridinyl)piperazinyl]carbonyl}butyl)-2,2-dimethyl-1,3-dioxolan-4-one;

(5S)-5-((1S)-4-(4-ethoxyphenyl)-1-{[(2R)-2-methyl-4-(2-pyrimidinyl)piperazinyl]carbonyl}butyl)-2,2-dimethyl-1,3-dioxolan-4-one;

(5S)-5-((1S)-4-(4-ethoxyphenyl)-1-{[(2R)-4-(2-fluorophenyl)-2-methyl piperazinyl]carbonyl}butyl)-2,2-dimethyl-1,3-dioxolan-4-one;

(5S)-2,2-dimethyl-5-((1S)-3-methyl-1-{[(2R)-2-methyl-4-pyrimidin-2-ylpiperazin-1-yl]carbonyl}butyl)-1,3-dioxolan-4-one;

(5S)-2,2-dimethyl-5-((1S)-3-methyl-1-{[(2S)-2-methyl-4-(4-methylpyridin-2-yl)piperazin-1-yl]carbonyl}butyl)-1,3-dioxolan-4-one;

(5S)-5-[(1S)-1-({(2R)-4-[2-fluoro-5-(methyloxy)phenyl]-2-methylpiperazin-1-yl}carbonyl)-3-methylbutyl]-2,2-dimethyl-1,3-dioxolan-4-one;

(5S)-5-((1S)-1-{[(2R)-4-(2-fluorophenyl)-2-methylpiperazin-1-yl]carbonyl}-3-methylbutyl)-2,2-dimethyl-1,3-dioxolan-4-one;

(5R)-5-((1S)-1-{[4-(4-methoxyphenyl)piperazin-1-yl]carbonyl}-3-methylbutyl)-2,2-dimethyl-1,3-dioxolan-4-one;

(5S)-5-((1S)-1-{[(2R)-4-(4-chloro-2-fluorophenyl)-2-methylpiperazin-1-yl]carbonyl}-3-methylbutyl)-2,2-dimethyl-1,3-dioxolan-4-one;

(5S)-5-((1S)-1-{[(2R)-4-(5-chloropyridin-2-yl)-2-methylpiperazin-1-yl]carbonyl}-3-methyl butyl)-2,2-dimethyl-1,3-dioxolan-4-one;

(5R)-5-((1S)-1-{[4-(4-fluorophenyl)piperazin-1-yl]carbonyl}-3-methylbutyl)-2,2-dimethyl-1,3-dioxolan-4-one;

(5R)-5-((1S)-1-{[(1S,4S)-5-(4-fluorophenyl)-2,5-diazabicyclo[2.2.1]hept-2-yl]carbonyl}-3-methylbutyl)-2,2-dimethyl-1,3-dioxolan-4-one;

(5R)-2,2-dimethyl-5-{(1S)-3-methyl-1-[(4-pyridin-2-ylpiperazin-1-yl)carbonyl]butyl}-1,3-dioxolan-4-one;

(5R)-2,2-dimethyl-5-[(1S)-3-methyl-1-({4-[4-(trifluoromethyl)phenyl]piperazin-1-yl}carbonyl)butyl]-1,3-dioxolan-4-one;

(5R)-5-((1S)-1-{[4-(2-fluorophenyl)piperazin-1-yl]carbonyl}-3-methylbutyl)-2,2-dimethyl-1,3-dioxolan-4-one;

(5R)-2,2-dimethyl-5-{(1S)-3-methyl-1-[(4-pyrimidin-2-ylpiperazin-1-yl)carbonyl]butyl}-1,3-dioxolan-4-one;

(5S)-2,2-dimethyl-5-{(1S)-3-methyl-1-[((2R)-2-methyl-4-{4-[(trifluoromethyl)oxy]phenyl}piperazin-1-yl)carbonyl]butyl}-1,3-dioxolan-4-one;

(5S)-5-((1S)-1-{[(2R)-4-biphenyl-4-yl-2-methylpiperazin-1-yl]carbonyl}-3-methylbutyl)-2,2-dimethyl-1,3-dioxolan-4-one;

(5S)-5-((1S)-1-{[(2S)-4-(2-fluorophenyl)-2-methylpiperazin-1-yl]carbonyl}-3-methyl butyl)-2,2-dimethyl-1,3-dioxolan-4-one;

(5S)-5-((1S)-1-{[(2R)-4-(3-chlorophenyl)-2-methylpiperazin-1-yl]carbonyl}-3-methyl butyl)-2,2-dimethyl-1,3-dioxolan-4-one;

(5R)-2,2-dimethyl-5-((1S)-3-methyl-1-{[4-(5-phenyl-1,2,4-oxadiazol-3-yl)-1-piperazinyl]carbonyl}butyl)-1,3-dioxolan-4-one;

(5S)-2,2-dimethyl-5-((1S)-3-methyl-1-{[(2R)-2-methyl-4-(5-phenylpyridin-2-yl)piperazin-1-yl]carbonyl}butyl)-1,3-dioxolan-4-one;

3-[(4-biphenyl-4-ylpiperazin-1-yl)carbonyl]-3,4-dideoxy-1,2-O-(1-methylethylidene)-5-O-(phenylmethyl)-L-threo-pentonic acid;

(5R)-5-[(1S)-1-({4-[5-(4-fluorophenyl)-1,3,4-oxadiazol-2-yl]piperidin-1-yl}carbonyl)-3-methylbutyl]-2,2-dimethyl-1,3-dioxolan-4-one;

(5R)-5-((1S)-1-{[4-(4-fluorophenyl)-3,6-dihydropyridin-1(2H)-yl]carbonyl}-3-methyl butyl)-2,2-dimethyl-1,3-dioxolan-4-one;

(5R)-2,2-dimethyl-5-{(1S)-3-methyl-1-[(4-phenyl-3,6-dihydropyridin-1(2H)-yl)carbonyl]butyl}-1,3-dioxolan-4-one;

(5R)-2,2-dimethyl-5-((1S)-3-methyl-1-{[4-(5-pyridin-4-yl-1,2,4-oxadiazol-3-yl)piperazin-1-yl]carbonyl}butyl)-1,3-dioxolan-4-one;

(5R)-5-((1S)-1-{[4-(4-chlorophenyl)-3,6-dihydropyridin-1(2H)-yl]carbonyl}-3-methyl butyl)-2,2-dimethyl-1,3-dioxolan-4-one;

(5S)-5-((1S)-1-{[4-(2-fluorophenyl)-1-piperazinyl]carbonyl}-3-methylbutyl)-2,2-dimethyl-1,3-dioxolan-4-one;

(5R)-2,2-dimethyl-5-[(1S)-3-methyl-1-({4-[5-(2-thienyl)-1,2,4-oxadiazol-3-yl]piperazin-1-yl}carbonyl)butyl]-1,3-dioxolan-4-one;

(5R)-5-(1-{[(2R)-4-(5-chloropyridin-2-yl)-2-methylpiperazin-1-yl]carbonyl}-3-methyl butyl)-2,2-dimethyl-1,3-dioxolan-4-one;

(5R)-5-((1S)-1-{[4-(5-chloropyridin-2-yl)piperazin-1-yl]carbonyl}-3-methylbutyl)-2,2-dimethyl-1,3-dioxolan-4-one;

(5R)-5-((1S)-1-{[4-(5-bromopyridin-2-yl)piperazin-1-yl]carbonyl}-3-methylbutyl)-2,2-dimethyl-1,3-dioxolan-4-one;

(5S)-5-((1R)-1-{[(2R)-4-(4-chlorophenyl)-2-methylpiperazin-1-yl]carbonyl}-3-methyl butyl)-2,2-dimethyl-1,3-dioxolan-4-one;

(5S)-2,2-dimethyl-5-[(1R)-3-methyl-1-({(2R)-2-methyl-4-[5-(trifluoromethyl)pyridin-2-yl]piperazin-1-yl}carbonyl)butyl]-1,3-dioxolan-4-one;

(5R)-5-((1S)-1-benzyl-2-oxo-2-{4-[4-(trifluoromethoxy)phenyl]piperazin-1-yl}ethyl)-2,2-dimethyl-1,3-dioxolan-4-one;

(5S)-5-((1S)-1-benzyl-2-{(2R)-2-methyl-4-[4-(trifluoromethoxy)phenyl]piperazin-1-yl}-2-oxoethyl)-2,2-dimethyl-1,3-dioxolan-4-one;

(5R)-2,2-dimethyl-5-((1S)-1-methyl-2-oxo-2-{4-[4-(trifluoromethoxy)phenyl]piperazin-1-yl}ethyl)-1,3-dioxolan-4-one;

(5S)-2,2-dimethyl-5-(1-methyl-2-{(2R)-2-methyl-4-[4-(trifluoromethoxy)phenyl]piperazin-1-yl}-2-oxoethyl)-1,3-dioxolan-4-one;

(5S)-5-((1S)-1-{[(2R)-4-(4'-fluorobiphenyl-4-yl)-2-methylpiperazin-1-yl]carbonyl}-3-methylbutyl)-2,2-dimethyl-1,3-dioxolan-4-one;

(5S)-5-((1R)-1-{[(2R)-4-(4-ethoxyphenyl)-2-methylpiperazin-1-yl]carbonyl}-3-methyl butyl)-2,2-dimethyl-1,3-dioxolan-4-one;

(5S)-5-((1S)-1-{[(2R)-4-(3,4-dimethoxyphenyl)-2-methylpiperazin-1-yl]carbonyl}-3-methylbutyl)-2,2-dimethyl-1,3-dioxolan-4-one;

(5S)-2,2-dimethyl-5-[3-methyl-1-({(2R)-2-methyl-4-[4-(methylsulfonyl)phenyl]piperazin-1-yl}carbonyl)butyl]-1,3-dioxolan-4-one;

(5S)-5-((1S)-1-{[(2R)-4-(6-methoxy-2-naphthyl)-2-methylpiperazin-1-yl]carbonyl}-3-methylbutyl)-2,2-dimethyl-1,3-dioxolan-4-one;

(5S)-5-[(1S)-1-({(2R)-4-[4-(1-benzofuran-3-yl)phenyl]-2-methylpiperazin-1-yl}carbonyl)-3-methylbutyl]-2,2-dimethyl-1,3-dioxolan-4-one;

(5S)-2,2-dimethyl-5-((1S)-3-methyl-1-{[(2R)-2-methyl-4-(4-propoxyphenyl)piperazin-1-yl]carbonyl}butyl)-1,3-dioxolan-4-one;

(5S)-2,2-dimethyl-5-[(1S)-3-methyl-1-({(2R)-2-methyl-4-[4-(trifluoromethyl)phenyl]piperazin-1-yl}carbonyl)butyl]-1,3-dioxolan-4-one;

(5S)-5-((1S)-1-{[(2R)-4-(4-tert-butylphenyl)-2-methylpiperazin-1-yl]carbonyl}-3-methyl butyl)-2,2-dimethyl-1,3-dioxolan-4-one;

(5S)-5-((1S)-1-{[(2R)-4-(5-fluoropyrimidin-2-yl)-2-methylpiperazin-1-yl]carbonyl}-3-methylbutyl)-2,2-dimethyl-1,3-dioxolan-4-one;

(5S)-2,2-dimethyl-5-((1S)-3-methyl-1-{[(2R)-2-methyl-4-(4-propylphenyl)piperazin-1-yl]carbonyl}butyl)-1,3-dioxolan-4-one;

(5S)-5-((1S)-1-(cyclopentylmethyl)-2-{(2R)-2-methyl-4-[4-(trifluoromethoxy)phenyl]piperazin-1-yl}-2-oxoethyl)-2,2-dimethyl-1,3-dioxolan-4-one;

(5S)-5-((1S)-1-{[(2R)-4-(2,3-dihydro-1-benzofuran-5-yl)-2-methylpiperazin-1-yl]carbonyl}-3-methylbutyl)-2,2-dimethyl-1,3-dioxolan-4-one;

(5S)-5-((1S)-1-{[(2R)-4-(1,3-benzodioxol-5-yl)-2-methylpiperazin-1-yl]carbonyl}-3-methylbutyl)-2,2-dimethyl-1,3-dioxolan-4-one;

(5S)-5-((1S)-1-{[(2R)-4-(4-methoxyphenyl)-2-methylpiperazin-1-yl]carbonyl}-3-methylbutyl)-2,2-dimethyl-1,3-dioxolan-4-one;

(5S)-2,2-dimethyl-5-{(1S)-3-methyl-1-[((2R)-2-methyl-4-{4-[(trifluoromethyl)sulfonyl]phenyl}piperazin-1-yl)carbonyl]butyl}-1,3-dioxolan-4-one;

(5S)-5-((1S)-1-{[(2R)-4-(4'-methoxybiphenyl-4-yl)-2-methylpiperazin-1-yl]carbonyl}-3-methylbutyl)-2,2-dimethyl-1,3-dioxolan-4-one;

(5S)-5-(1-{[(2R)-4-(4-cyclohexylphenyl)-2-methylpiperazin-1-yl]carbonyl}-3-methylbutyl)-2,2-dimethyl-1,3-dioxolan-4-one;

(5S)-5-((1S)-1-{[(2R)-4-(1-benzofuran-5-yl)-2-methylpiperazin-1-yl]carbonyl}-3-methyl butyl)-2,2-dimethyl-1,3-dioxolan-4-one;

(5S)-5-((1S)-1-{[(2R)-4-(2,2-difluoro-1,3-benzodioxol-5-yl)-2-methylpiperazin-1-yl]carbonyl}-3-methylbutyl)-2,2-dimethyl-1,3-dioxolan-4-one;

(5S)-5-(1-{[(2R)-4-(3-fluoro-4-methoxyphenyl)-2-methylpiperazin-1-yl]carbonyl}-3-methylbutyl)-2,2-dimethyl-1,3-dioxolan-4-one;

(5S)-5-((1S)-1-{[(2R)-4-(3-fluoro-4-isopropoxyphenyl)-2-methylpiperazin-1-yl]carbonyl}-3-methylbutyl)-2,2-dimethyl-1,3-dioxolan-4-one;

(5S)-5-[(1S)-1-({(2R)-4-[3-fluoro-4-(trifluoromethoxy)phenyl]-2-methylpiperazin-1-yl}carbonyl)-3-methylbutyl]-2,2-dimethyl-1,3-dioxolan-4-one;

(5S)-2,2-dimethyl-5-((1S)-3-methyl-1-{[(2R)-2-methyl-4-quinolin-3-ylpiperazin-1-yl]carbonyl}butyl)-1,3-dioxolan-4-one;

(5S)-2,2-dimethyl-5-((1S)-3-methyl-1-{[(2R)-2-methyl-4-(4-methylphenyl)piperazin-1-yl]carbonyl}butyl)-1,3-dioxolan-4-one;

(5S)-5-((1S)-1-{[(2R)-4-(5-chloro-2-thienyl)-2-methylpiperazin-1-yl]carbonyl}-3-methyl butyl)-2,2-dimethyl-1,3-dioxolan-4-one;

(5S)-5-((1S)-1-{[(2R)-4-(3-methoxyphenyl)-2-methylpiperazin-1-yl]carbonyl}-3-methylbutyl)-2,2-dimethyl-1,3-dioxolan-4-one.

In another embodiment, the invention provides a compound according to Formula (V):

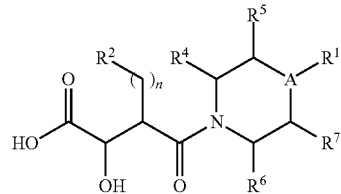

wherein A, $R^1$, $R^2$, $R^4$, $R^5$, $R^6$, $R^7$ and n are as defined above.

In a further embodiment, the invention provides a compound according to Formula (V) selected from the group:

(2S,3S)-2-hydroxy-5-methyl-3-[(4-pyridin-2-ylpiperazin-1-yl)carbonyl]hexanoic acid;

(2S,3S)-2-hydroxy-5-methyl-3-{[4-(3-phenyl-1,2,4-thiadiazol-5-yl)piperazin-1-yl]carbonyl}hexanoic acid;

(2S,3S)-2-hydroxy-5-methyl-3-({(2R)-2-methyl-4-[4-(trifluoromethyl)pyridin-2-yl]piperazin-1-yl}carbonyl)hexanoic acid;

(2S,3S)-2-hydroxy-5-methyl-3-{[(2R)-2-methyl-4-pyridin-2-ylpiperazin-1-yl]carbonyl}hexanoic acid;

(2S,3S)-2-hydroxy-5-methyl-3-{[(2S)-2-methyl-4-pyridin-2-ylpiperazin-1-yl]carbonyl}hexanoic acid;

(2S,3S)-2-hydroxy-5-methyl-3-{[(2R)-2-methyl-4-pyrimidin-2-ylpiperazin-1-yl]carbonyl}hexanoic acid;

(2S,3S)-2-hydroxy-5-methyl-3-{[(2S)-2-methyl-4-(4-methylpyridin-2-yl)piperazin-1-yl]carbonyl}hexanoic acid;

(2S,3S)-3-{[(2R)-4-(2-fluoro-5-methoxyphenyl)-2-methylpiperazin-1-yl]carbonyl}-2-hydroxy-5-methylhexanoic acid;

(2S,3S)-3-{[(2R)-4-(2-fluorophenyl)-2-methylpiperazin-1-yl]carbonyl}-2-hydroxy-5-methylhexanoic acid;

(2R,3S)-2-hydroxy-3-{[4-(4-methoxyphenyl)piperazin-1-yl]carbonyl}-5-methylhexanoic acid;

(2S,3S)-3-{[(2R)-4-(4-chloro-2-fluorophenyl)-2-methylpiperazin-1-yl]carbonyl}-2-hydroxy-5-methylhexanoic acid;

(2S,3S)-3-{[(2R)-4-(5-chloropyridin-2-yl)-2-methylpiperazin-1-yl]carbonyl}-2-hydroxy-5-methylhexanoic acid;

(2R,3S)-3-{[4-(4-fluorophenyl)piperazin-1-yl]carbonyl}-2-hydroxy-5-methylhexanoic acid;

(2R,3S)-2-hydroxy-5-methyl-3-[(4-pyridin-2-ylpiperazin-1-yl)carbonyl]hexanoic acid;

(2R,3S)-2-hydroxy-5-methyl-3-({4-[4-(trifluoromethyl)phenyl]piperazin-1-yl}carbonyl)hexanoic acid;

(2R,3S)-3-{[4-(2-fluorophenyl)piperazin-1-yl]carbonyl}-2-hydroxy-5-methylhexanoic acid;

(2R,3S)-2-hydroxy-5-methyl-3-[(4-pyrimidin-2-ylpiperazin-1-yl)carbonyl]hexanoic acid;

(2S,3S)-2-hydroxy-5-methyl-3-({(2R)-2-methyl-4-[4-(trifluoromethoxy)phenyl]piperazin-1-yl}carbonyl)hexanoic acid;

(2S,3S)-3-[(2R)-4-biphenyl-4-yl-2-methylpiperazin-1-yl]carbonyl)-2-hydroxy-5-methyl hexanoic acid;

(2S,3S)-3-{[(2S)-4-(2-fluorophenyl)-2-methylpiperazin-1-yl]carbonyl}-2-hydroxy-5-methylhexanoic acid;

(2S,3S)-3-{[(2R)-4(3-chlorophenyl)-2-methylpiperazin-1-yl]carbonyl}-2-hydroxy-5-methylhexanoic acid;

(2R,3S)-2-hydroxy-5-methyl-3-{[4-(5-phenyl-1,2,4-oxadiazol-3-yl)piperazin-1-yl]carbonyl}hexanoic acid;

(2S,3S)-2-hydroxy-5-methyl-3-{[(2R)-2-methyl-4-(5-phenylpyridin-2-yl)piperazin-1-yl]carbonyl}hexanoic acid;

5-O-benzyl-3-[(4-biphenyl-4-ylpiperazin-1-yl)carbonyl]-3,4-dideoxy-L-threo-pentonic acid;

(2R,3S)-3-({4-[5-(4-fluorophenyl)-1,3,4-oxadiazol-2-yl]piperidin-1-yl}carbonyl)-2-hydroxy-5-methylhexanoic acid;

(2R,3S)-3-{[4-(4-fluorophenyl)-3,6-dihydropyridin-1(2H)-yl]carbonyl}-2-hydroxy-5-methylhexanoic acid;

(2R,3S)-2-hydroxy-5-methyl-3-[(4-phenyl-3,6-dihydropyridin-1(2H)-yl)carbonyl]hexanoic acid;

(2R,3S)-2-hydroxy-5-methyl-3-{[4-(5-pyridin-4-yl-1,2,4-oxadiazol-3-yl)piperazin-1-yl]carbonyl}hexanoic acid;

(2R,3S)-3-{[4-(4-chlorophenyl)-3,6-dihydropyridin-1(2H)-yl]carbonyl}-2-hydroxy-5-methylhexanoic acid;

(2S,3S)-3-{[4-(2-fluorophenyl)piperazin-1-yl]carbonyl}-2-hydroxy-5-methylhexanoic acid;

(2R,3S)-2-hydroxy-5-methyl-3-({4-[5-(2-thienyl)-1,2,4-oxadiazol-3-yl]piperazin-1-yl}carbonyl)hexanoic acid;

(2R,3S)-3-{[(2R)-4-(5-chloropyridin-2-yl)-2-methylpiperazin-1-yl]carbonyl}-2-hydroxy-5-methylhexanoic acid;

(2R,3S)-3-{[4-(5-chloropyridin-2-yl)piperazin-1-yl]carbonyl}-2-hydroxy-5-methyl hexanoic acid;

(2R,3S)-3-{[4-(5-bromopyridin-2-yl)piperazin-1-yl]carbonyl}-2-hydroxy-5-methyl hexanoic acid;

(2S,3S)-3-{[(2R)-4-(4-chlorophenyl)-2-methylpiperazin-1-yl]carbonyl}-2-hydroxy-5-methyl hexanoic acid;

(2S,3S)-2-hydroxy-5-methyl-3-({(2R)-2-methyl-4-[5-(trifluoromethyl)pyridin-2-yl]piperazin-1-yl}carbonyl)hexanoic acid;

(2R,3S)-3-benzyl-2-hydroxy-4-oxo-4-{4-[4-(trifluoromethoxy)phenyl]piperazin-1-yl}butanoic acid;

(2S,3S)-3-benzyl-2-hydroxy-4-{(2R)-2-methyl-4-[4-(trifluoromethoxy)phenyl]piperazin-1-yl}-4-oxobutanoic acid;

(2R,3S)-2-hydroxy-3-methyl-4-oxo-4-{4-[4-(trifluoromethoxy)phenyl]piperazin-1-yl}butanoic acid;

(2S)-2-hydroxy-3-methyl-4-{(2R)-2-methyl-4-[4-(trifluoromethoxy)phenyl]piperazin-1-yl}-4-oxobutanoic acid;

(2S,3S)-3-{[(2R)-4-(4'-fluorobiphenyl-4-yl)-2-methylpiperazin-1-yl]carbonyl}-2-hydroxy-5-methylhexanoic acid;

(2S,3S)-3-{[(2R)-4-(4-ethoxyphenyl)-2-methylpiperazin-1-yl]carbonyl}-2-hydroxy-5-methylhexanoic acid;

(2S,3S)-3-{[(2R)-4-(3,4-dimethoxyphenyl)-2-methylpiperazin-1-yl]carbonyl}-2-hydroxy-5-methylhexanoic acid;

(2S,3S)-2-hydroxy-5-methyl-3-({(2R)-2-methyl-4-[4-(methylsulfonyl)phenyl]piperazin-1-yl}carbonyl)hexanoic acid;

(2S,3S)-2-hydroxy-3-{[(2R)-4-(6-methoxy-2-naphthyl)-2-methylpiperazin-1-yl]carbonyl}-5-methylhexanoic acid;

(2S,3S)-3-({(2R)-4-[4-(1-benzofuran-3-yl)phenyl]-2-methylpiperazin-1-yl}carbonyl)-2-hydroxy-5-methylhexanoic acid;

(2S,3S)-2-hydroxy-5-methyl-3-{[(2R)-2-methyl-4-(4-propoxyphenyl)piperazin-1-yl]carbonyl}hexanoic acid;

(2S,3S)-2-hydroxy-5-methyl-3-({(2R)-2-methyl-4-[4-(trifluoromethyl)phenyl]piperazin-1-yl}carbonyl)hexanoic acid;

(2S,3S)-3-{[(2R)-4-(4-tert-butylphenyl)-2-methylpiperazin-1-yl]carbonyl}-2-hydroxy-5-methylhexanoic acid;

(2S,3S)-3-{[(2R)-4-(5-fluoropyrimidin-2-yl)-2-methylpiperazin-1-yl]carbonyl}-2-hydroxy-5-methylhexanoic acid;

(2S,3S)-2-hydroxy-5-methyl-3-{[(2R)-2-methyl-4-(4-propylphenyl)piperazin-1-yl]carbonyl}hexanoic acid;

(2S,3S)-3-(cyclopentylmethyl)-2-hydroxy-4-{(2R)-2-methyl-4-[4-(trifluoromethoxy)phenyl]piperazin-1-yl}-4-oxobutanoic acid;

(2S,3S)-3-{[(2R)-4-(2,3-dihydro-1-benzofuran-5-yl)-2-methylpiperazin-1-yl]carbonyl}-2-hydroxy-5-methylhexanoic acid;

(2S,3S)-3-{[(2R)-4-(1,3-benzodioxol-5-yl)-2-methylpiperazin-1-yl]carbonyl}-2-hydroxy-5-methylhexanoic acid;

(2S,3S)-2-hydroxy-3-{[(2R)-4-(4-methoxyphenyl)-2-methylpiperazin-1-yl]carbonyl}-5-methylhexanoic acid;

(2S,3S)-2-hydroxy-5-methyl-3-[((2R)-2-methyl-4-{4-[(trifluoromethyl)sulfonyl]phenyl}piperazin-1-yl)carbonyl]hexanoic acid;

(2S,3S)-2-hydroxy-3-{[(2R)-4-(4'-methoxybiphenyl-4-yl)-2-methylpiperazin-1-yl]carbonyl}-5-methylhexanoic acid;

(2S,3S)-3-{[(2R)-4-(4-cyclohexylphenyl)-2-methylpiperazin-1-yl]carbonyl}-2-hydroxy-5-methylhexanoic acid;

(2S,3S)-3-{[(2R)-4-(1-benzofuran-5-yl)-2-methylpiperazin-1-yl]carbonyl}-2-hydroxy-5-methylhexanoic acid;

(2S,3S)-3-{[(2R)-4-(2,2-difluoro-1,3-benzodioxol-5-yl)-2-methylpiperazin-1-yl]carbonyl}-2-hydroxy-5-methylhexanoic acid;

(2S,3S)-3-{[(2R)-4-(3-fluoro-4-methoxyphenyl)-2-methylpiperazin-1-yl]carbonyl}-2-hydroxy-5-methylhexanoic acid;

(2S,3S)-3-{[(2R)-4-(3-fluoro-4-isopropoxyphenyl)-2-methylpiperazin-1-yl]carbonyl}-2-hydroxy-5-methylhexanoic acid;

(2S,3S)-3-({(2R)-4-[3-fluoro-4-(trifluoromethoxy)phenyl]-2-methylpiperazin-1-yl}carbonyl)-2-hydroxy-5-methyl hexanoic acid;

(2S,3S)-2-hydroxy-5-methyl-3-{[(2R)-2-methyl-4-quinolin-3-ylpiperazin-1-yl]carbonyl}hexanoic acid;

(2S,3S)-2-hydroxy-5-methyl-3-{[(2R)-2-methyl-4-(4-methylphenyl)piperazin-1-yl]carbonyl}hexanoic acid;

(2S,3S)-3-{[(2R)-4-(5-chloro-2-thienyl)-2-methylpiperazin-1-yl]carbonyl}-2-hydroxy-5-methylhexanoic acid;

(2S,3S)-2-hydroxy-3-{[(2R)-4-(3-methoxyphenyl)-2-methylpiperazin-1-yl]carbonyl}-5-methylhexanoic acid.

In another embodiment, the invention provides a compound according to Formula (III):

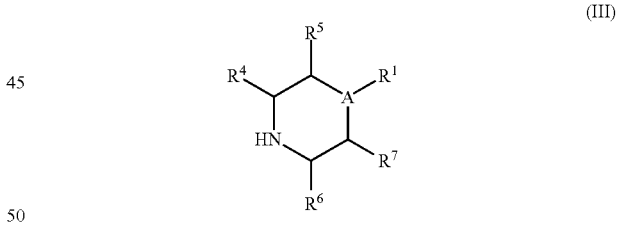

wherein $R^2$, $R^4$, $R^5$, $R^6$, $R^7$ are as defined above and A is N and $R^1$ is an optionally substituted aryl or optionally substituted heteroaryl and wherein the compound according to Formula (III) selected from the group:

(3R)-1-(2-fluorophenyl)-3-methylpiperazine;
(3S)-1-(2-Fluorophenyl)-3-methylpiperazine;
(3R)-3-methyl-1-[4-(trifluoromethyl)pyridin-2-yl]piperazine;
5-fluoro-2-[(3R)-3-methylpiperazin-1-yl]pyrimidine;
(3R)-3-methyl-[5-(trifluoromethyl)pyridin-2-yl]piperazine;
(3R)-3-methyl-1-(4-propylphenyl)piperazine;
(3R)-1-(6-methoxy-2-naphthyl)-3-methylpiperazine;
(3R)-1-[4-(1-benzofuran-3-yl)phenyl]-3-methylpiperazine;
(3R)-3-methyl-1-(4-propoxyphenyl)piperazine;
(3R)-1-(4'-fluorobiphenyl-4-yl)-3-methylpiperazine;
(3R)-3-methyl-1-[4-(trifluoromethoxy)phenyl]piperazine;

(3R)-1-(3,4-dimethoxyphenyl)-3-methylpiperazine;
(3R)-3-methyl-1-[4-(methylsulfonyl)phenyl]piperazine;
(3R)-1-(2,3-dihydro-1-benzofuran-5-yl)-3-methylpiperazine;
(3R)-1-(1,3-benzodioxol-5-yl)-3-methylpiperazine;
(3R)-3-methyl-1-{4-[(trifluoromethyl)sulfonyl]phenyl}piperazine;
(3R)-1-(4-tert-butylphenyl)-3-methylpiperazine;
(3R)-1-(4-ethoxyphenyl)-3-methylpiperazine;
(3S)-3-methyl-1-(4-methylpyridin-2-yl)piperazine;
(3R)-1-(2-fluoro-5-methoxyphenyl)-3-methylpiperazine;
(3R)-1-(4-chloro-2-fluorophenyl)-3-methylpiperazine;
(3R)-1-(5-chloro pyridin-2-yl)-3-methylpiperazine;
(3R)-1-biphenyl-4-yl-3-methyl-piperazine;
(3R)-3-methyl-1-(5-phenyl-pyridin-2-yl)piperazine;
(3R)-1-(4'-methoxybiphenyl-4-yl)-3-methylpiperazine;
(3R)-1-(4-cyclohexylphenyl)-3-methylpiperazine;
(3R)-1-(1-benzofuran-5-yl)-3-methylpiperazine;
(3R)-1-(2,2-difluoro-1,3-benzodioxol-5-yl)-3-methylpiperazine;
(3R)-1-(3-fluoro-4-methoxyphenyl)-3-methylpiperazine;
3R)-1-(3-fluoro-4-isopropoxyphenyl)-3-methylpiperazine;
(3R)-1-[3-fluoro-4-(trifluoromethoxy)phenyl]-3-methylpiperazine;
3-[(3R)-3-methylpiperazin-1-yl]quinoline.

The compounds of invention have been named according the standards used in the program "ACD/Name" from Advanced Chemistry Development Inc., ACD/Labs (7.00 Release).

The compounds of Formula (I) are useful for the treatment and/or prophylaxis of autoimmune disorders, inflammatory diseases, cardiovascular diseases, neurodegenerative diseases, stroke, cancer, respiratory diseases, pre-term labor, endometriosis and fibrosis, including multiple sclerosis, arthritis, emphysema, chronic obstructive pulmonary disease, liver and pulmonary fibrosis.

In another embodiment, the compounds of the invention can be used in the treatment of autoimmune diseases, especially demyelinating diseases such as multiple sclerosis, alone or in combination with a co-agent useful in the treatment of autoimmune diseases, wherein the co-agent is for example selected from the following compounds:

(a) Interferons, e.g. pegylated or non-pegylated interferons, e.g. administered by sub-cutaneous, intramuscular or oral routes, preferably interferon beta;

(b) Glatiramer, e.g. in the acetate form;

(c) Immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH;

(d) Adenosine deaminase inhibitors, e.g. Cladribine;

(e) Inhibitors of VCAM-1 expression or antagonists of its ligand, e.g. antagonists of the α4/β1 integrin VLA-4 and/or alpha-4-beta-7 integrins, e.g. natalizumab (ANTEGRENO).

Another aspect of the invention is to provide compounds of Formula (VI):

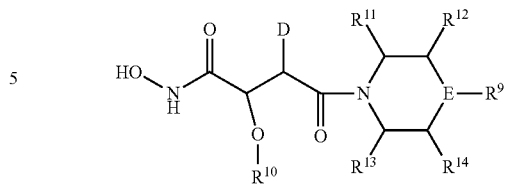

wherein:
E is selected from —CH and N;
D is the group:

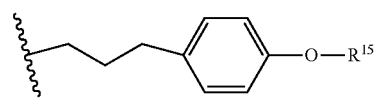

$R^9$ is selected from H; optionally substituted aryl, including optionally substituted phenyl such as phenyl, cyano phenyl (e.g. 5-cyanophenyl, 2-cyanophenyl), chlorophenyl (e.g. 4-chlorophenyl, 2-chlorophenyl, 3,5-dichloropyridin), 4-chloro-2-fluorophenyl, methoxy phenyl (e.g. 2-methoxy phenyl) and fluorophenyl (e.g. 2-fluorophenyl, 4-fluorophenyl); optionally substituted heteroaryl, including optionally substituted piperazinyl, optionally substituted pyrazinyl (e.g. 4-pyrazin-2-yl), optionally substituted pyridinyl, such as pyridinyl (e.g. 4-pyridin-2-yl), chloropyridinyl (e.g. 6-chloropyridin-2-yl, 5-chloropyridin-2-yl, dichloropyridinyl), cyanopyridinyl (e.g. 5-cyanopyridin-2-yl), methylpyridinyl (e.g. 6-methylpyridine-2-yl) and trifluoromethylpyridinyl (e.g. 5-(trifluoromethyl)pyridinyl, 3-(trifluoromethyl)pyridin), optionally substituted fused pyridinyl such as 6-methyl-2-(trifluoromethyl)quinolinyl; optionally substituted $C_3$-$C_8$-cycloalkyl $C_1$-$C_6$ alkyl; optionally substituted heteroaryl $C_1$-$C_6$ alkyl including thienyl ethyl (e.g. 2-(2-thienyl)ethyl); optionally substituted $C_3$-$C_8$-cycloalkyl, including cyclohexyl; optionally substituted heterocycloalkyl $C_1$-$C_6$ alkyl, including morpholino ethyl (e.g. 2-morpholin-4-ylethyl); optionally substituted $C_1$-$C_6$ alkyl, including propyl and hydroxyethyl; optionally substituted amino, including amino substituted by optionally substituted aryl and optionally substituted heteroaryl, e.g. amino substituted by the following substitutents: phenyl, methoxy phenyl (e.g. 3-methoxy phenyl), trifluoromethyl pyrimidyl (e.g. 3-(trifluoromethyl)pyrimidin-2-yl, 5-(trifluoromethyl)pyrimidin-2-yl), dimethyl amino phenyl (e.g. 3-(dimethyl amino)phenyl), amino pyridinyl (e.g. 3-aminopyridin-2-yl), chloro phenyl, hydroxyl phenyl (e.g. 4-hydroxyphenyl); and optionally substituted alkoxy, including trifluoro methyl phenoxy (e.g. 4-(trifluoromethyl)phenoxy), pyridinyl oxy (e.g. 4-(pyridin-2-yloxy)) and chloro phenoxy (e.g. 2-chlorophenoxy);

$R^{10}$ is selected from H, optionally substituted $C_1$-$C_6$ alkyl, optionally substituted $C_2$-$C_6$ alkenyl and optionally substituted $C_2$-$C_6$ alkynyl;

$R^{11}$, $R^{12}$, $R^{13}$ and $R^{14}$ are independently selected from H; optionally substituted $C_1$-$C_6$ alkyl, including methyl; optionally substituted $C_2$-$C_6$ alkenyl; optionally substituted $C_2$-$C_6$ alkynyl; or $R^{11}$ and $R^{14}$ can form together a —$CH_2$— linkage.

$R^{15}$ is optionally substituted $C_1$-$C_6$ alkyl, including trifluoromethyl, methyl and ethyl; as well as its optically active forms as enantiomers, diastereomers and its racemate forms, as well as pharmaceutically acceptable salts thereof.

In one embodiment of the invention, are provided compounds of Formula (VI) wherein E is —CH.

In another embodiment, are provided compounds of Formula (VI) wherein E is N.

In another embodiment, are provided compounds of Formula (VI) wherein $R^9$ is optionally substituted amino.

In a further embodiment, are provided compounds of Formula (VI) wherein $R^9$ is selected from amino substituted with optionally substituted aryl and amino substituted with optionally substituted heteroaryl.

In another embodiment, are provided compounds of Formula (VI) wherein $R^9$ is optionally substituted alkoxy.

In another embodiment, are provided compounds of Formula (VI) wherein $R^9$ is optionally substituted heterocycloalkyl $C_1$-$C_6$ alkyl.

In another embodiment, are provided compounds of Formula (VI) wherein $R^9$ is optionally substituted heteroaryl $C_1$-$C_6$ alkyl.

In a further embodiment, are provided compounds of Formula (VI) wherein $R^9$ is optionally substituted thienyl ethyl.

In another embodiment, are provided compounds of Formula (VI) wherein $R^9$ is selected from optionally substituted aryl and optionally substituted heteroaryl.

In a further embodiment, are provided compounds of Formula (VI) wherein $R^9$ is optionally substituted phenyl selected from optionally substituted cyano phenyl (e.g. 5-cyanophenyl, 2-cyanophenyl), optionally substituted chlorophenyl (e.g. 4-chlorophenyl, 2-chlorophenyl, 3,5-dichloropyridin), 4-chloro-2-fluorophenyl, 2-methoxy phenyl and 4-fluorophenyl.

In another further embodiment, are provided compounds of Formula (VI) wherein $R^9$ is optionally substituted pyrazinyl.

In another further embodiment, are provided compounds of Formula (VI) wherein $R^9$ is substituted pyridyl.

In another further embodiment, are provided compounds of Formula (VI) wherein $R^9$ is optionally substituted quinolinyl.

In another embodiment, are provided compounds of Formula (VI) wherein $R^{10}$ is H.

In another embodiment, are provided compounds of Formula (VI) wherein $R^{11}$, $R^{12}$, $R^{13}$ and $R^{14}$ are H.

In another embodiment, are provided compounds of Formula (VI) wherein $R^{12}$ and $R^{13}$ are H; and $R^{11}$ and $R^{14}$ form together a —$CH_2$— linkage.

In another embodiment, are provided compounds of Formula (VI) wherein E is selected from —CH and N; $R^9$ is optionally substituted aryl, optionally substituted heteroaryl, optionally substituted $C_3$-$C_8$-cycloalkyl $C_1$-$C_6$ alkyl, optionally substituted $C_3$-$C_8$-cycloalkyl, optionally substituted heterocycloalkyl $C_1$-$C_6$ alkyl, optionally substituted $C_1$-$C_6$ alkyl, optionally substituted amino and optionally substituted alkoxy; $R^{10}$, $R^{12}$ and $R^{13}$ are H; $R^{11}$ and $R^{14}$ form together a —$CH_2$— linkage; $R^{15}$ is optionally substituted $C_1$-$C_6$ alkyl.

In a further embodiment, are provided compounds of Formula (VI) wherein E is selected from —CH and N; $R^9$ is selected from optionally substituted cyano phenyl, optionally substituted chlorophenyl, optionally substituted 2-methoxy phenyl, optionally substituted 4-fluorophenyl, optionally substituted pyrazinyl and substituted pyridinyl; $R^{10}$, $R^{11}$, $R^{12}$, $R^{13}$ and $R^{14}$ are H; $R^{15}$ is optionally substituted $C_1$-$C_6$ alkyl.

In another further embodiment, are provided compounds of Formula (VI) wherein E is selected from —CH and N; $R^9$ is optionally substituted $C_3$-$C_8$-cycloalkyl; $R^{10}$, $R^{11}$, $R^{12}$, $R^{13}$ and $R^{14}$ are H; $R^{15}$ is optionally substituted $C_1$-$C_6$ alkyl.

In another further embodiment, are provided compounds of Formula (VI) wherein E is selected from —CH and N; $R^9$ is optionally substituted $C_1$-$C_6$-alkyl; $R^{10}$, $R^{11}$, $R^{12}$, $R^{13}$ and $R^{14}$ are H; $R^{15}$ is optionally substituted $C_1$-$C_6$ alkyl.

In another further embodiment, are provided compounds of Formula (VI) wherein E is selected from —CH and N; $R^9$ is optionally substituted $C_3$-$C_8$-cycloalkyl $C_1$-$C_6$ alkyl and optionally substituted heterocycloalkyl $C_1$-$C_6$ alkyl; $R^{10}$, $R^{11}$, $R^{12}$, $R^{13}$ and $R^{14}$ are H; $R^{15}$ is optionally substituted $C_1$-$C_6$ alkyl.

In another further embodiment, are provided compounds of Formula (VI) wherein E is selected from —CH and N; $R^9$ is selected from optionally substituted phenyl, optionally substituted pyrazinyl and optionally substituted pyridyl; $R^{10}$, $R^{12}$ and $R^{13}$ are H; $R^{11}$ and $R^{14}$ form together a —$CH_2$— linkage; $R^{15}$ is optionally substituted $C_1$-$C_6$ alkyl.

In another further embodiment, are provided compounds of Formula (VI) wherein E is selected from —CH and N; $R^9$ is selected from amino substituted with optionally substituted aryl and amino substituted with optionally substituted heteroaryl; $R^{10}$, $R^{11}$, $R^{12}$, $R^{13}$ and $R^{14}$ are H; $R^{15}$ is optionally substituted $C_1$-$C_6$ alkyl.

In another embodiment, are provided compounds of Formula (VI) wherein E is selected from —CH and N; $R^9$ is optionally substituted alkoxy; $R^{10}$, $R^{11}$, $R^{12}$, $R^{13}$ and $R^{14}$ are H; $R^{15}$ is optionally substituted $C_1$-$C_6$ alkyl.

Compounds of Formula (VI) of the present invention include in particular those selected from the following group:

(2S,3R)-6-(4-ethoxyphenyl)-3-{[4-(4-fluorophenyl)piperazin-1-yl]carbonyl}-N,2-dihydroxyhexanamide;

(2S,3R)-3-[(4-anilinopiperidin-1-yl)carbonyl]-6-(4-ethoxyphenyl)-N,2-dihydroxy hexanamide;

(2S,3R)-6-(4-ethoxyphenyl)-N,2-dihydroxy-3-({4-[5-(trifluoromethyl)pyridin-2-yl]piperazin-1-yl}carbonyl)hexanamide;

(2S,3R)-6-(4-ethoxyphenyl)-N,2-dihydroxy-3-{[4-(pyridin-2-yloxy)piperidin-1-yl]carbonyl}hexanamide;

(2S,3R)-3-{[4-(5-cyanopyridin-2-yl)piperazin-1-yl]carbonyl}-6-(4-ethoxyphenyl)-N,2-dihydroxyhexanamide;

(2S,3R)-6-(4-ethoxyphenyl)-N,2-dihydroxy-3-{[4-(6-methylpyridin-2-yl)piperazin-1-yl]carbonyl}hexanamide;

(2S,3R)-3-{[4-(6-chloropyridin-2-yl)piperazin-1-yl]carbonyl}-6-(4-ethoxyphenyl)-N,2-dihydroxyhexanamide;

(2S,3R)-3-{[4-(5-chloropyridin-2-yl)piperazin-1-yl]carbonyl}-6-(4-ethoxyphenyl)-N,2-dihydroxyhexanamide;

(2S,3R)-3-{[4-(4-chloro-2-fluorophenyl)piperazin-1-yl]carbonyl}-6-(4-ethoxyphenyl)-N,2-dihydroxyhexanamide;

(2S,3R)-6-(4-ethoxyphenyl)-N,2-dihydroxy-3-({4-[4-(trifluoromethyl)phenoxy]piperidin-1-yl}carbonyl)hexanamide;

(2S,3R)-3-{[4-(2-chlorophenoxy)piperidin-1-yl]carbonyl}-6-(4-ethoxyphenyl)-N,2-dihydroxyhexanamide;

(2S,3R)-3-{[4-(2-chlorophenyl)piperazin-1-yl]carbonyl}-6-(4-ethoxyphenyl)-N,2-dihydroxylhexanamide;

(2S,3R)-6-(4-ethoxyphenyl)-N,2-dihydroxy-3-({4-[6-methyl-2-(trifluoromethyl)quinolin-4-yl]piperazin-1-yl}carbonyl)hexanamide;

(2S,3R)-6-(4-ethoxyphenyl)-N,2-dihydroxy-3-({4-[3-(trifluoromethyl)pyridin-2-yl]piperazin-1-yl}carbonyl)hexanamide;

(2S,3R)-3-{[4-(3,5-dichloropyridin-4-yl)piperazin-1-yl]carbonyl}-6-(4-ethoxyphenyl)-N,2-dihydroxyhexanamide;

(2S,3R)-6-(4-ethoxyphenyl)-N,2-dihydroxy-3-{[4-(2-methoxyphenyl)piperazin-1-yl]carbonyl}hexanamide;

(2S,3R)-3-{[4-(4-chlorophenyl)piperazin-1-yl]carbonyl}-6-(4-ethoxyphenyl)-N,2-dihydroxylhexanamide;

(2S,3R)-6-(4-ethoxyphenyl)-N,2-dihydroxy-3-[(4-pyrazin-2-ylpiperazin-1-yl)carbonyl]hexanamide;

(2S,3R)-6-(4-ethoxyphenyl)-N,2-dihydroxy-3-{[4-(2-morpholin-4-ylethyl)piperazin-1-yl]carbonyl}hexanamide;

(2S,3R)-3-{[4-(2-cyanophenyl)piperazin-1-yl]carbonyl}-6-(4-ethoxyphenyl)-N,2-dihydroxyhexanamide;
(2S,3R)-3-{[4-(2-fluorophenyl)piperazin-1-yl]carbonyl}-N,2-dihydroxy-6-[4-(trifluoro methoxy)phenyl]hexanamide;
(2S,3R)-3-{[4-(6-chloropyridin-2-yl)piperazin-1-yl]carbonyl}-N,2-dihydroxy-6-[4-(trifluoromethoxy)phenyl]hexanamide;
(2S,3R)—N,2-dihydroxy-3-[(4-pyridin-2-ylpiperazin-1-yl)carbonyl]-6-[4-(trifluoromethoxy)henyl]hexanamide;
(2S,3R)-6-(4-ethoxyphenyl)-N,2-dihydroxy-3-[(4-{[4-(trifluoromethyl)pyrimidin-2-yl]amino}piperidin-1-yl)carbonyl]hexanamide;
(2S,3R)-6-(4-ethoxyphenyl)-N,2-dihydroxy-3-({4-[(3-methoxyphenyl)amino]piperidin-1-yl}carbonyl)hexanamide;
(2S,3R)-3-[(4-{[3-(dimethylamino)phenyl]amino}piperidin-1-yl)carbonyl]-6-(4-ethoxy phenyl)-N,2-dihydroxyhexanamide;
(2S,3R)-3-({4-[(3-aminopyridin-2-yl)amino]piperidin-1-yl}carbonyl)-6-(4-ethoxyphenyl)-N,2-dihydroxyhexanamide;
(2S,3R)-6-(4-ethoxyphenyl)-N,2-dihydroxy-3-({4-[(4-hydroxyphenyl)amino]piperidin-1-yl}carbonyl)hexanamide;
(2S,3R)-6-(4-ethoxyphenyl)-3-{[(1S,4S)-5-(4-fluorophenyl)-2,5-diazabicyclo[2.2.1]hept-2-yl]carbonyl}-N,2-dihydroxyhexanamide;
(2S,3R)-6-(4-ethoxyphenyl)-N,2-dihydroxy-3-({4-[2-(2-thienyl)ethyl]piperazin-1-yl}carbonyl)hexanamide;
(2S,3R)-3-[(4-cyclohexylpiperazin-1-yl)carbonyl]-6-(4-ethoxyphenyl)-N,2-dihydroxyhexanamide;
(2S)-6-(4-ethoxyphenyl)-N,2-dihydroxy-3-{[4-(2-hydroxyethyl)piperidin-1-yl]carbonyl}hexanamide;
(2S,3R)-6-(4-ethoxyphenyl)-3-{[4-(4-fluorophenyl)piperidin-1-yl]carbonyl}-N,2-dihydroxyhexanamide;
(2S,3R)—N,2-dihydroxy-6-(4-methoxyphenyl)-3-[(4-propylpiperidin-1-yl)carbonyl]hexanamide.

In another embodiment, the invention provides a compound according to Formula (VII):

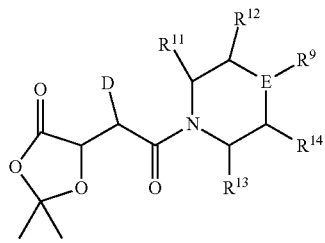

wherein E is selected from —CH and N; $R^9$ is selected from optionally substituted phenyl selected from optionally substituted cyano phenyl (e.g. 5-cyanophenyl, 2-cyanophenyl), optionally substituted chlorophenyl (e.g. 4-chlorophenyl, 2-chlorophenyl, dichloropyridin), 4-chloro-2-fluorophenyl, 2-methoxy phenyl and 4-fluorophenyl; optionally substituted pyrazinyl (e.g. 4-pyrazin-2-yl); substituted pyridinyl, such as chloropyridinyl (e.g. 6-chloropyridin-2-yl, 5-chloropyridin-2-yl, dichloropyridinyl), cyanopyridinyl (e.g. 5-cyanopyridin-2-yl), methylpyridinyl (e.g. 6-methylpyridine-2-yl) and trifluoromethylpyridinyl (e.g. 5-(trifluoromethyl)pyridinyl, 3-(trifluoromethyl)pyridin), optionally substituted fused pyridinyl such as 6-methyl-2-(trifluoromethyl)quinolinyl; optionally substituted $C_3$-$C_8$-cycloalkyl $C_1$-$C_6$ alkyl; optionally substituted thienyl ethyl (e.g. 2-(2-thienyl)ethyl); optionally substituted $C_3$-$C_8$-cycloalkyl, including cyclohexyl; optionally substituted heterocycloalkyl $C_1$-$C_6$ alkyl, including morpholino ethyl (e.g. 2-morpholin-4-ylethyl); optionally substituted $C_1$-$C_6$ alkyl, including propyl and hydroxyethyl; optionally substituted amino, including amino substituted by optionally substituted aryl and optionally substituted heteroaryl, e.g. amino substituted by the following substitutents: phenyl, methoxy phenyl (e.g. 3-methoxy phenyl), trifluoromethyl pyrimidyl (e.g. 3-(trifluoromethyl)pyrimidin-2-yl, 5-(trifluoromethyl)pyrimidin-2-yl), dimethyl amino phenyl (e.g. 3-(dimethyl amino) phenyl), amino pyridinyl (e.g. 3-aminopyridin-2-yl), chloro phenyl, hydroxyl phenyl (e.g. 4-hydroxyphenyl); and optionally substituted alkoxy, including trifluoro methyl phenoxy (e.g. 4-(trifluoromethyl)phenoxy), pyridinyl oxy (e.g. 4-(pyridin-2-yloxy)) and chloro phenoxy (e.g. 2-chlorophenoxy);

$R^{11}$, $R^{12}$, $R^{13}$ and $R^{14}$ are independently selected from H; optionally substituted $C_1$-$C_6$ alkyl, including methyl; optionally substituted $C_2$-$C_6$ alkenyl; optionally substituted $C_2$-$C_6$ alkynyl; or $R^{11}$ and $R^{14}$ can form together a —$CH_2$— linkage;
D is as described above;
$R^{15}$ is optionally substituted $C_1$-$C_6$ alkyl, including trifluoromethyl, methyl and ethyl; as well as pharmaceutically acceptable salts thereof.

In a further embodiment, the invention provides a compound according to Formula (VII) selected from the group:
(5S)-5-((1R)-4-(4-ethoxyphenyl)-1-{[4-(4-fluorophenyl)piperazin-1-yl]carbonyl}butyl)-2,2-dimethyl-1,3-dioxolan-4-one;
(5S)-5-((1R)-4-[4-(ethyloxy)phenyl]-1-{[4-(phenylamino)piperidin-1-yl]carbonyl}butyl)-2,2-dimethyl-1,3-dioxolan-4-one;
(5S)-5-[(1R)-4-[4-(ethyloxy)phenyl]-1-({4-[5-(trifluoromethyl)pyridin-2-yl]piperazin-1-yl}carbonyl)butyl]-2,2-dimethyl-1,3-dioxolan-4-one;
(5S)-5-((1R)-4-[4-(ethyloxy)phenyl]-1-{[4-(pyridin-2-yloxy)piperidin-1-yl]carbonyl}butyl)-2,2-dimethyl-1,3-dioxolan-4-one;
6-(4-({2R}-2-[(4S)-2,2-dimethyl-5-oxo-1,3-dioxolan-4-yl]-5-[4-(ethyloxy)phenyl]pentanoyl}piperazin-1-yl)pyridine-3-carbonitrile;
(5S)-5-((1R)-4-[4-(ethyloxy)phenyl]-1-{[4-(6-methylpyridin-2-yl)piperazin-1-yl]carbonyl}butyl)-2,2-dimethyl-1,3-dioxolan-4-one;
(5S)-5-{(1R)-1-{[4-(6-chloropyridin-2-yl)piperazin-1-yl]carbonyl}-4-[4-(ethyloxy)phenyl]butyl}-2,2-dimethyl-1,3-dioxolan-4-one;
(5S)-5-{(1R)-1-{[4-(5-chloropyridin-2-yl)piperazin-1-yl]carbonyl}-4-[4-(ethyloxy)phenyl]butyl}-2,2-dimethyl-1,3-dioxolan-4-one;
(5S)-5-{(1R)-1-{[4-(4-chloro-2-fluorophenyl)piperazin-1-yl]carbonyl}-4-[4-(ethyloxy)phenyl]butyl}-2,2-dimethyl-1,3-dioxolan-4-one;
(5S)-5-{(1R)-4-[4-(ethyloxy)phenyl]-1-[(4-{[4-(trifluoromethyl)phenyl]oxy}piperidin-1-yl)carbonyl]butyl}-2,2-dimethyl-1,3-dioxolan-4-one;
(5S)-5-{(1R)-1-({4-[(2-chlorophenyl)oxy]piperidin-1-yl}carbonyl)-4-[4-(ethyloxy)phenyl]butyl}-2,2-dimethyl-1,3-dioxolan-4-one;
(5S)-5-{(1R)-1-{[4-(2-chlorophenyl)piperazin-1-yl]carbonyl}-4-[4-(ethyloxy)phenyl]butyl}-2,2-dimethyl-1,3-dioxolan-4-one;
(5S)-5-[(1R)-4-[4-(ethyloxy)phenyl]-1-({4-[6-methyl-2-(trifluoromethyl)quinolin-4-yl]piperazin-1-yl}carbonyl)butyl]-2,2-dimethyl-1,3-dioxolan-4-one;

(5S)-5-[(1R)-4-[4-(ethyloxy)phenyl]-1-({4-[3-(trifluoromethyl)pyridin-2-yl]piperazin-1-yl}carbonyl)butyl]-2,2-dimethyl-1,3-dioxolan-4-one;
(5S)-5-{(1R)-1-{[4-(3,5-dichloropyridin-4-yl)piperazin-1-yl]carbonyl}-4-[4-(ethyloxy)phenyl]butyl}-2,2-dimethyl-1,3-dioxolan-4-one;
(5S)-5-[(1R)-4-[4-(ethyloxy)phenyl]-1-({4-[2-(methyloxy)phenyl]piperazin-1-yl}carbonyl)butyl]-2,2-dimethyl-1,3-dioxolan-4-one;
(5S)-5-{(1R)-1-{[4-(4-chlorophenyl)piperazin-1-yl]carbonyl}-4-[4-(ethyloxy)phenyl]butyl}-2,2-dimethyl-1,3-dioxolan-4-one;
(5S)-5-{(1R)-4-[4-(ethyloxy)phenyl]-1-[(4-pyrazin-2-ylpiperazin-1-yl)carbonyl]butyl}-2,2-dimethyl-1,3-dioxolan-4-one;
(5S)-5-((1R)-4-[4-(ethyloxy)phenyl]-1-{[4-(2-morpholin-4-ylethyl)piperazin-1-yl]carbonyl}butyl)-2,2-dimethyl-1,3-dioxolan-4-one;
2-(4-{(2R)-2-[(4S)-2,2-dimethyl-5-oxo-1,3-dioxolan-4-yl]-5-[4-(ethyloxy)phenyl]pentanoyl}piperazin-1-yl)benzonitrile;
(5S)-5-((1R)-1-{[4-(6-chloropyridin-2-yl)piperazin-1-yl]carbonyl}-4-{4-[(trifluoromethyl)oxy]phenyl}butyl)-2,2-dimethyl-1,3-dioxolan-4-one;
(5S)-5-{(1R)-4-[4-(ethyloxy)phenyl]-1-[(4-{[4-(trifluoromethyl)pyrimidin-2-yl]amino}piperidin-1-yl)carbonyl]butyl}-2,2-dimethyl-1,3-dioxolan-4-one;
(5S)-5-{(1R)-4-[4-(ethyloxy)phenyl]-1-[(4-{[3-(methyloxy)phenyl]amino}piperidin-1-yl)carbonyl]butyl}-2,2-dimethyl-1,3-dioxolan-4-one;
(5S)-5-{(1R)-1-[(4-{[3-(dimethylamino)phenyl]amino}piperidin-1-yl)carbonyl]-4-[4-(ethyloxy)phenyl]butyl}-2,2-dimethyl-1,3-dioxolan-4-one;
(5S)-5-{(1R)-1-({4-[(3-aminopyridin-2-yl)amino]piperidin-1-yl}carbonyl)-4-[4-(ethyloxy)phenyl]butyl}-2,2-dimethyl-1,3-dioxolan-4-one;
(5S)-5-[(1R)-4-[4-(ethyloxy)phenyl]-1-({4-[(4-hydroxyphenyl)amino]piperidin-1-yl}carbonyl)butyl]-2,2-dimethyl-1,3-dioxolan-4-one;
(5S)-5-((1R)-4-[4-(ethyloxy)phenyl]-1-{[(1S,4S)-5-(4-fluorophenyl)-2,5-diazabicyclo[2.2.1]kept-2-yl]carbonyl}butyl)-2,2-dimethyl-1,3-dioxolan-4-one;
(5S)-5-[(1R)-4-(4-ethoxyphenyl)-1-({4-[2-(2-thienyl)ethyl]-1-piperazinyl}carbonyl)butyl]-2,2-dimethyl-1,3-dioxolan-4-one;
(5S)-5-{(1R)-1-[(4-cyclohexylpiperazin-1-yl)carbonyl]-4-[4-(ethyloxy)phenyl]butyl}-2,2-dimethyl-1,3-dioxolan-4-one;
(5S)-5-((1R)-4-[4-(ethyloxy)phenyl]-1-{[4-(2-hydroxyethyl)piperidin-1-yl]carbonyl}butyl)-2,2-dimethyl-1,3-dioxolan-4-one;
(5S)-5-((1R)-4-[4-(ethyloxy)phenyl]-1-{[4-(4-fluorophenyl)piperidin-1-yl]carbonyl}butyl)-2,2-dimethyl-1,3-dioxolan-4-one;
(5S)-2,2-dimethyl-5-{(1R)-4-[4-(methyloxy)phenyl]-1-[(4-propylpiperidin-1-yl)carbonyl]butyl}-1,3-dioxolan-4-one.

Compounds according to the present invention also comprise its tautomers, its geometrical isomers, its optically active forms as enantiomers, diastereomers and its racemate forms, as well as pharmaceutically acceptable salts thereof. Preferred pharmaceutically acceptable salts of the Formula (VI) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

In another embodiment of the invention, are provided compounds of Formula (VI) for use as a medicament.

In another embodiment of the invention, is provided a pharmaceutical composition comprising a compound of Formula (VI) and a pharmaceutically acceptable carrier, diluent or excipient thereof.

In another embodiment of the invention, is provide a use of N-hydroxyamide derivatives according to Formula (VI) for the preparation of a medicament for the prophylaxis and/or treatment of a disorder selected from autoimmune disorders, inflammatory diseases, stroke, cardiovascular diseases, neurodegenerative diseases, cancer, pre-term labor, endometriosis, respiratory diseases and fibrosis, including multiple sclerosis, inflammatory bowel disease, arthritis, emphysema, chronic obstructive pulmonary disease, pulmonary, pancreatic fibrosis, skin and liver fibrosis.

In another embodiment of the invention, is provided a use of N-hydroxyamide derivatives according to Formula (VI) for the modulation, in particular for the inhibition, of the matrix metalloproteinase activity. Particularly, is provided a use according to the invention wherein said matrix metalloproteinase is selected from MMP-2, MMP-9 and MMP-12. Preferably, compounds according to the invention are selective inhibitors of metalloproteineases selected from MMP-2, MMP-9 and/or MMP-12 over MMP-1.

In another embodiment, the invention provides a method of treatment and/or prophylaxis of a disease comprising the administration of a compound according to Formula (VI), in a patient in need thereof and wherein the disease is selected from autoimmune disorders, inflammatory diseases, cardiovascular diseases, neurodegenerative diseases, stroke, cancer, pre-term labor, endometriosis, respiratory diseases and fibrosis, including multiple sclerosis, arthritis, emphysema, chronic obstructive pulmonary disease (COPD), liver, skin and pulmonary fibrosis.

The compounds of Formula (VI) are useful for the treatment and/or prophylaxis of autoimmune disorders, inflammatory diseases, cardiovascular diseases, neurodegenerative diseases, stroke, cancer, pre-term labor, endometriosis, respiratory diseases and fibrosis, including multiple sclerosis, arthritis, emphysema, chronic obstructive pulmonary disease, liver, skin and pulmonary fibrosis.

The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of the invention and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.-

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, pre-measured ampoules or syringes of the liquid compositions or pills, tablets, capsules or the like in the case of solid compositions. In such compositions, the derivative of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above mentioned, the N-hydroxyamide derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

Synthesis of Compounds of the Invention:

The novel derivatives according to Formula (I) can be prepared from readily available starting materials by several synthetic approaches, using both solution-phase and solid-phase chemistry protocols. Examples of synthetic pathways for the will be described.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), µL (microliter), ACN (acetonitrile), BINAP (2,2'-bis(diphenylphosphino)-1,1'-binaphthalene), Boc (tert-Butoxycarbonyl), $CDCl_3$ (deuterated chloroform), $CD_3OD$ (Deuterated methanol), $CH_3CN$ (Acetonitrile), c-hex (Cyclohexane), db a (dibenzylidene acetone), DCC (dicyclohexyl carbodiimide), DCM (Dichloromethane), DIC (Diisopropyl carbodiimide), DIEA (Diisopropylethyl-amine), DMF (Dimethylformamide), DMSO (Dimethylsulfoxide), DMSO-$d_6$ (Deuterated dimethylsulfoxide), dppf (1,1'-diphenylphosphino ferrocen), EDC (1-(3-Dimethyl-amino-propyl)-3-ethylcarbodiimide), ESI (Electro-spray ionization), EtOAc (Ethyl acetate), $Et_2O$ (Diethyl ether), EtOH (Ethanol), Fmoc (9-Fluorenyl methoxycarbonyl), HATU (Dimethylamino-([1,2,3]triazolo[4,5-b]pyridin-3-yloxy)-methylene]dimethyl-ammonium hexafluorophosphate), HPLC (High Performance Liquid Chromatography), i-PrOH (2-propanol), $K_2CO_3$ (Potassium carbonate), LC (Liquid Chromatography), MeOH (Methanol), $MgSO_4$ (Magnesium sulfate), MS (mass spectrometry), MTBE (Methyl tert-butyl ether), $NaHCO_3$ (Sodium bicarbonate), $NaBH_4$ (Sodium borohydride), NMM (N-methyl morpholine), NMR (Nuclear Magnetic Resonance), RT (room temperature), PyBOP® (Benzotriazole-1-yl-oxy-tris-pyrrolidino-phosphonium hexafluorophosphate), Rt (retention time), SPE (solid phase extraction), TBTU (2-(1-H-benzotriazole-1-yl)-1,1,3,3-tetramethyluromium tetrafluoro borate), TEA (Triethylamine), TFA (Trifluoroacetic acid), THF (Tetrahydrofuran), THP (Tetrahydropyranyl), TLC (Thin Layer Chromatography), UV (Ultraviolet).

Synthetic Approaches:

A preferred process for preparing a compound of Formula (I) consists in coupling a dioxolane-protected di-carboxylic acid of formula (II) with the appropriate amine (III) to form the intermediate (IV) wherein A, $R^1$, $R^2$, $R^4$, $R^5$, $R^6$, $R^7$ and n are defined as above (Scheme 1 below). General protocols for such coupling are given below in the Examples, using conditions and methods well known to those skilled in the art to prepare an amide bond from an amine and a carboxylic acid or carboxylic acid derivative (e.g. acid chloride), with or without standard coupling agents, such as e.g. DIC, EDC, TBTU, DCC, HATU, PyBOP®, Isobutyl chloroformate, 1-methyl-2-chloropyridinium iodide (Mukaiyama's reagent) or others in the presence or not of bases such as TEA, DIEA, NMM in a suitable solvent such as DCM, THF or DMF.

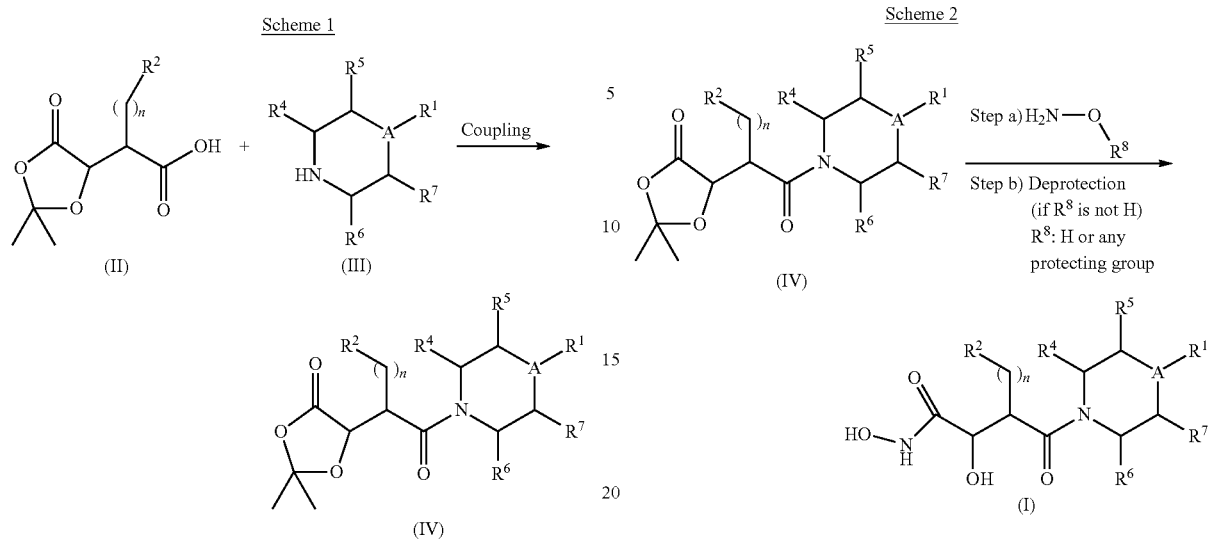

Compounds of Formula (III) are commercially available or can be obtained from protocols is herein described.

An attractive method for the preparation of compounds of Formula (III) wherein A is N and $R^1$ is an optionally substituted aryl or heteroaryl may be the reaction of piperazine of Formula (IX) with an aryl halide or sulfonate of Formula (X) where X is a leaving group such as Cl, Br, I, Ms, or Tf, in the presence of a palladium catalyst such as $Pd(OAc)_2$ or $Pd_2(dba)_3$, $PdCl_2(dppf)$, a phosphine such as (+/−)-BINAP, $PPh_3$, $P(p-Tol)_3$, 1,1'-diphenyl phosphino ferrocene (dppf) and a base such as t-BuOK or t-BuONa. In some cases, when the aryl halide or sulfonate of Formula (X) is sufficiently reactive (e.g. 2-chloro-pyridine), the reaction can proceed without the palladium catalyst and without phosphines.

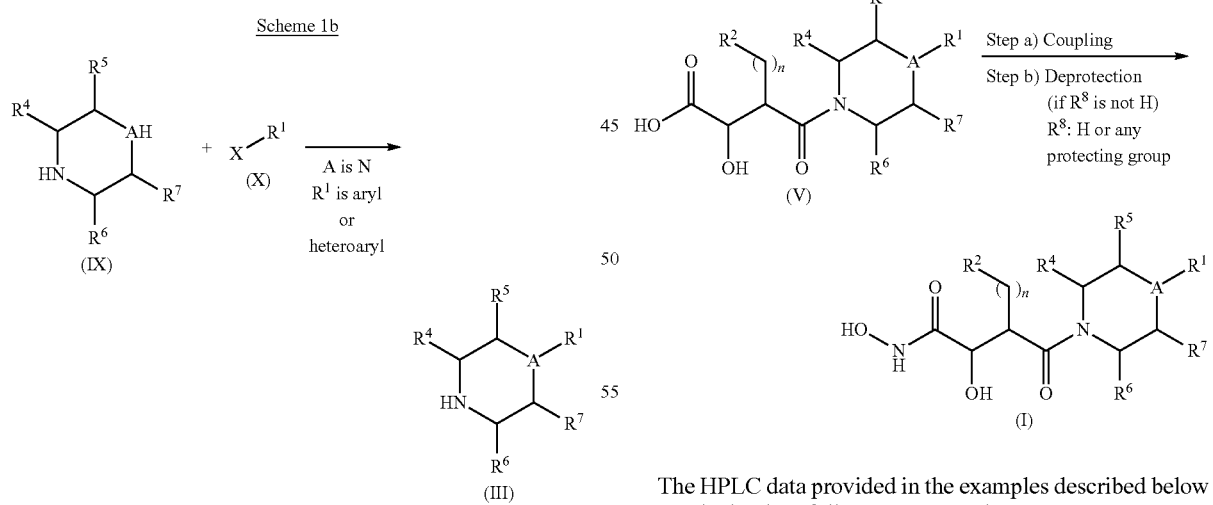

Intermediate of formula (IV) can be reacted with a hydroxylamine or with a protected hydroxylamine $H_2NO$—$R^8$ where $R^8$ is a protecting group such as t-butyl, benzyl, trialkylsilyl or any suitable protecting group, followed by a known deprotection step to form compound of Formula (I) (Scheme 2 below).

Intermediates of formula (II) may be prepared by methods known or by protocols herein described.

An alternative route for the preparation of compounds of Formula (I) may be the coupling of a carboxylic acids of formula (V) with hydroxylamine or with a protected hydroxylamine $H_2NO$—$R^8$ where $R^8$ is a protecting group such as t-butyl, benzyl, trialkylsilyl, tetrahydropyranyl (THP) or any suitable protecting group, with or without standard coupling agents, such as e.g. DIC, EDC, TBTU, DCC, HATU, PyBOP®, Isobutyl chloroformate, 1-methyl-2-chloropyridinium iodide (Mukaiyama's reagent), followed by a known deprotection step to form compound of Formula (I) (Scheme 3 below).

The HPLC data provided in the examples described below were obtained as follows. HPLC columns: Waters Xterra® MS $C_8$ column 50 mm×4.6 mm at a flow of 2 mL/min for conditions A and B. Waters Xterra® MS C8 column 150 mm×4.6 mm at a flow of 1 mL/min for conditions C and D.

Conditions A: 8 min gradient from 0.1% TFA in $H_2O$ to 0.07% TFA in $CH_3CN$.

Conditions B: 8 min gradient from 95% $H_2O$ to 100% $CH_3CN$.

Conditions C: 20 min gradient from 95% H₂O to 100% CH₃CN.

Conditions D: 20 min gradient from 95% H₂O to 40% CH₃CN. UV detection (maxplot) for all conditions.

The preparative HPLC were obtained with a Waters Xterra® Prep MS C₈ 10 µm column 300 mm×30 mm; UV detection (254 nM and 220 nM); flow: 30 mL/min. The MS data provided in the examples described below were obtained as followed: Mass spectrum: LC/MS Waters ZMD (ESI). The NMR data provided in the examples described below were obtained as followed: ¹H-NMR: Bruker DPX-300 MHz.

According to a further general process, compounds of Formula (I) can be converted to alternative compounds of Formula (I), employing suitable interconversion techniques well known by a person skilled in the art.

If the above set of general synthetic methods are not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3ʳᵈ Edition 1999. Those skilled in the art will recognize that certain reactions are best carried out when potentially reactive functionality on the molecule is masked or protected, thus avoiding side reactions and/or increasing the yield of the reaction. Examples of protecting group moieties may be found in Philip J. Kocienski, 1994 above and in Greene et al., 1999, above. The need and choice of protecting groups for a particular reaction is known to those skilled in the art and depends on the nature of the functional group to be protected (hydroxy, amino, carboxy, etc.), the structure and the stability of the molecule of which the substituent is part of the reaction conditions.

Compounds of this invention can be isolated in association with solvent molecules by crystallization from evaporation of an appropriate solvent. The pharmaceutically acceptable is acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

The following reagents/resins commercially available were used:

Diisopropyl (S)-(−)-malate (from Avocado), 2,3,4,5,6-pentafluorophenol (from Fluka), 3-bromo-2-methylpropene (from Aldrich), allyl bromide (from Fluka), HATU (from Aldrich), 2,2-dimethoxypropane (from Fluka), lithium bis(trimethylsilyl)amide (from Aldrich), 4-bromophenetole (from Aldrich), 1-bromo-4-(trifluoromethoxy)benzene (from Aldrich), tri-o-tolylphosphine (from Aldrich), palladium(II) acetate (from Acros), copper (II) chloride (from Aldrich), 2-chloropyridine (from Aldrich), (R)-(−)-2-methylpiperazine (from Astatech), (S)-2-methyl-piperazine (from Aldrich), 1-(2-pyridyl)piperazine (from Aldrich), 3-phenyl-5-piperazino-1,2,4-thiadiazole (from Maybridge), 2-bromopyrimidine (from Aldrich), 1-bromo-2-fluorobenzene (from Fluka), 2-chloro-4-(trifluoromethyl)pyridine (from ABCR), 2,2"-bis(diphenylphosphino)-1,1'-binaphthalene (from Fluka), fluoro-N,N,N',N' tetramethylformamidinium hexafluorophosphate (from Aldrich), diiso propyl (R)-(+)-malate (from Aldrich), 1-(4-methoxyphenyl)-piperazine (from Chess), 2-chloro-4-methylpyridine (from Aldrich), 2-chloro-1-fluoro-4-methoxybenzene (from ABCR),1-bromo-4-chloro-2-fluorobenzene (from Aldrich), 2,5-dichloropyridine (from Aldrich), 4-(4-fluorophenyl)-1,2,3,6-tetrahydropyridine hydrochloride (from Acros), 4-phenyl-1,2,3,6-tetrahydropyridine hydrochloride (from Acros), 4-(4-chlorophenyl)-1,2,3,6-tetrahydropyridine hydrochloride (from Aldrich), 1-(2-thienylethyl)-piperazine (from Emlcachem), 1-cyclohexylpiperazine (from Spectrum), 4-piperidineethanol (from Aldrich), 4-(4-fluorophenyl)piperidine hydrochloride (from Arch), 4-propylpiperidine (from Aldrich), 1-Boc-piperazine (from Fluka), isonicotinic acid (from Fluka), 2-chloro-5-fluoropyrimidine (from Carbocore), 2-Bromo-5-trifluoromethyl-pyridine (from ABCR), 2,5-dibromopyridine (from Aldrich), 1-bromo-4-propylbenzene (from Aldrich), 2-bromo-6-methoxynaphthalene (from Fluka), 1-bromo-4-trifluoromethylbenzene (from Aldrich), 4-bromo-4'-fluorobiphenyl (from Pfaltz-Bauer), 1-bromo-4-(trifluoromethoxy) (from Apollo), 4-bromo-1,2-dimethoxybenzene (from Fluka), 4-fluorophenyl methyl sulfone (from ABCR),5-bromo-2,3-dihydrobenzo[b]furan (from Fluorochem), 4-bromo-1,2-(methylenedioxy)benzene (from Aldrich), 1-bromo-4-methoxybenzene (from Aldrich), 1-chloro-4-(trifluoromethanesulfonyl)benzene (from ABCR),1-bromo-4-tert-butylbenzene (from Aldrich), 1-bromo-4-ethoxybenzene (from Aldrich), 1-bromo-4-chlorobenzene (from Fluka), 1-Boc-piperazine (from Fluka), thiophene-2-carbonyl chloride (from Aldrich), iodomethane (from Aldrich), benzyl bromide (from Fluka), (iodomethyl)cyclopentane (from Acros), 1-bromo-3-fluoro-4-(trifluoromethoxy)benzene (from Apollo), 4'-bromobiphenyl-4-yl methyl ether (from Aldrich), 1-bromo-4-cyclohexylbenzene (from Lancaster), 5-bromo-1-benzofuran (from Maybridge), 5-bromo-2,2-difluoro-1,3-benzodioxole (from Apollo), 4-bromo-2-fluoro-1-methoxybenzene (from Aldrich), 4,4'-dibromobiphenyl (from Aldrich), 4-bromo-2-fluoro-1-(trifluoromethoxy)benzene (from Apollo), 6-bromoquinoline (from Maybridge), 1-bromo-3,5-bis(trifluoromethyl)benzene (from Aldrich), 1-bromo-4-methylbenzene (from Aldrich), 2-bromo-5-chlorothiophene (from Aldrich).

Intermediate 1: A 55/45 diastereoisomeric mixture of pentafluorophenyl (2S)-2-[(4S)-2,2-dimethyl-5-oxo-1,3-dioxolan-4-yl]-4-methylpentanoate and pentafluorophenyl (2R)-2-[(4S)-2,2-dimethyl-5-oxo-1,3-dioxolan-4-yl]-4-methylpentanoate

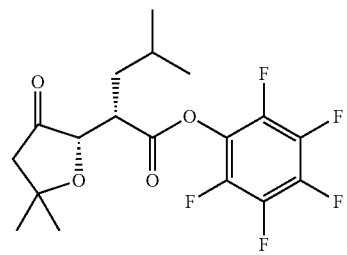

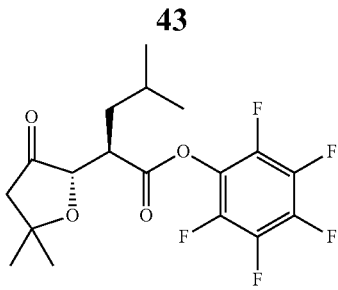

To a solution of 2,3,4,5,6-pentafluorophenyl (2R)-2-[(4S)-2,2-dimethyl-5-oxo-1,3-dioxolan-4-yl]-4-methylpentanoate (prepared according to WO 94/02447 or similarly to Seebach et al., 1990, *Org. Syntheses, Coll. Vol. III*, p 153-159; 5.0 g; 12.62 mmol; 1.0 eq.) in DCM (30 mL) was added TEA (1.81 mL; 12.62 mmol; 1.0 eq.). After 24 h of reaction at RT, the solvent was evaporated. Purification by chromatography (SiO$_2$, gradient starting from 18/82 EtOAc/c-hex up to 25/75 EtOAc/c-hex in about 30 min) gave the title compound as a white powder (4.22 g; 84%) as a diastereoisomeric mixture 55/45 (determined by NMR). $^1$H NMR (CDCl$_3$): δ 4.69 (d, 0.55H, J=4.5 Hz), 4.53 (d, 0.45H, J=6 Hz), 3.28 (m, 1H), 2.05-1.65 (m, 2H), 1.62 (m, 3H), 1.59-1.48 (m, 4H), 0.97 (m, 6H).

Intermediate 2: Formation of (2R)-2-[(4S)-2,2-dimethyl-5-oxo-1,3-dioxolan-4-yl]-5-(4-ethoxyphenyl)pentanoic acid

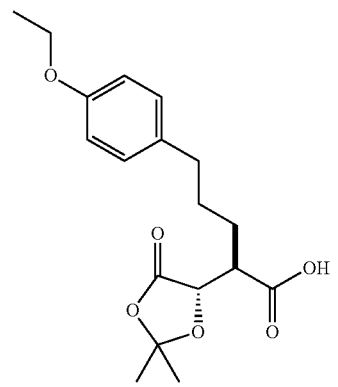

Step a) Formation of di-isopropyl (2R,3S)-2-allyl-3-hydroxybutanedioate (Intermediate 2a)

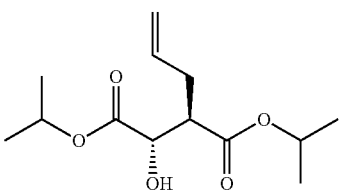

To a cold (−78° C.) solution of diisopropyl (S)-(−)-malate (4.74 mL; 22.9 mmol; 1.0 eq.) in anhydrous THF (8.50 mL) was slowly added under argon lithium bis(trimethylsilyl)amide (48.1 mL; 1.0 M in THF; 48.11 mmol; 2.1 eq.) keeping the temperature below −66° C. After to 45 min of addition, the reaction mixture was stirred at −78° C. for 2 h, then the temperature of the reaction mixture was allowed to reach 11° C. After 1 h at that temperature, the mixture was cooled at −78° C. and allyl bromide (2.9 mL; 34.4 mmol; 1.5 eq.) was added. The solution was stirred overnight allowing the temperature to reach RT. The reaction was then quenched with ice water and an aqueous saturated solution of NH$_4$Cl. The aqueous layer was extracted 3 times with EtOAc and the combined organic layers were washed with a saturated solution of NaCl, dried over MgSO$_4$ and evaporated to obtain an orange oil (5.4 g). Purification by chromatography (SiO$_2$, 10/90 EtOAc/c-hex) gave the title product as a colorless oil (3.05 g, 51.5%). $^1$H NMR (CDCl$_3$, 300 MHz) δ 5.76-5.59 (m, 1H), 5.07-4.80 (m, 4H), 4.08 (d, J=2.3 Hz, 1H), 3.03 (br s, 1H), 2.80-2.72 (m, 1H), 2.53-2.41 (m, 1H), 2.34-2.21 (m, 1H), 1.14 (d, J=6.4 Hz, 6H), 1.07 (d, J=6.4 Hz, 6H).

Step b) Formation of di-isopropyl (2R,3S)-2-[(2E)-3-(4-ethoxyphenyl)-2-propenyl]-3-hydroxybutanedioate

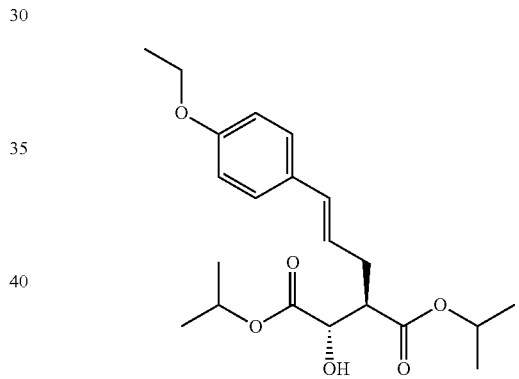

To a solution of diisopropyl (2R,3S)-2-allyl-3-hydroxybutanedioate (3.0 g; 11.6 mmol; 1.0 eq.) and DIEA (3.86 mL; 28.9 mmol; 2.4 eq.) in CH$_3$CN (30.0 mL) was added 4-bromophenetole (2.0 mL; 13.9 mmol; 1.2 eq.). To this solution was added a mixture of tri-o-tolylphosphine (0.35 g; 1.16 mmol; 0.1 eq.) and palladium(II) acetate (0.03 g; 0.12 mmol; 0.01 eq.) in CH$_3$CN (3.0 mL) which was sonicated before the addition to the reaction mixture. The reaction was stirred under argon at reflux for 2.5 h, cooled to RT and the solvents were evaporated under reduce pressure. The resulting residue was then taken up in EtOAc and washed with an aqueous saturated solution of NaCl. Evaporation of the solvent gave an oil (4.3 g). Purification by chromatography (SiO$_2$, gradient from 20/80 EtOAc/c-hex to 100/0 EtOAc/c-hex) gave the title product as a colorless oil (4.41 g, 100%). M$^+$(ESI): 379.3. $^1$H NMR (CDCl$_3$, 300 MHz) δ 7.14 (d, J=8.6 Hz, 2H), 6.70 (d, J=8.6 Hz, 2H), 6.46 (d, J=15.6 Hz, 1H), 6.00-5.86 (m, 1H), 5.05-4.83 (m, 2H), 4.13 (dd, J=7.0 Hz, J=3.0 Hz, 1H), 3.90 (q, J=7.0 Hz, 2H), 3.10 (d, J=7.2 Hz, 1H), 2.89-2.78 (m, 1H), 2.70-2.55 (m, 1H), 2.52-2.35 (m, 1H), 1.27 (t, J=7.0 Hz, 3H), 1.22-1.00 (m, 12H).

Step c) Formation of diisopropyl (2R,3S)-2-[3-(4-ethoxyphenyl)propyl]-3-hydroxybutane dioate

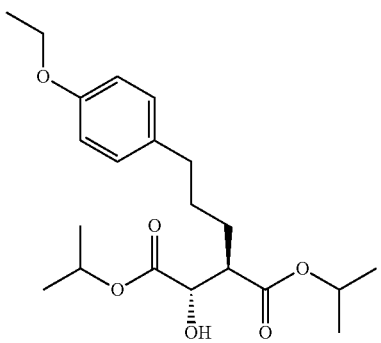

To a solution of diisopropyl (2R,3S)-2-[(2E)-3-(4-ethoxyphenyl)-2-propenyl]-3-hydroxy butanedioate (2.0 g; 5.28 mmol; 1.0 eq.) in methanol (154 mL) under $N_2$ atmosphere was added Pd/C (10%; 56 mg; 0.05 mmol; 0.01 eq.). The mixture was then hydrogenated under 2 bars of hydrogen for 14 h at RT. The reaction mixture was then filtered and evaporated to obtain an oil (1.91 g). Purification by chromatography ($SiO_2$, 20/80 EtOAc/c-hex) gave the title product as a colorless oil (1.9 g, 95%). $M^+$(ESI): 381.2. $^1$H NMR (CDCl$_3$, 300 MHz) δ 7.00 (d, J=8.7 Hz, 2H), 6.73 (d, J=8.7 Hz, 2H), 5.10-4.86 (m, 2H), 4.13 (br s, 1H), 3.93 (q, J=7.0 Hz, 2H), 3.12 (br s, 1H), 2.76-2.67 (m, 1H), 2.55-2.46 (m, 2H), 1.87-1.49 (m, 4H), 1.32 (t, J=7.0 Hz, 3H), 1.24-1.10 (m, 12H).

Step d) Formation of (2R,3S)-2-[3-(4-ethoxyphenyl)propyl]-3-hydroxybutanedioic acid

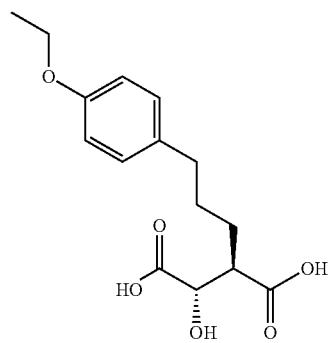

To a solution of diisopropyl (2R,3S)-2-[3-(4-ethoxyphenyl)propyl]-3-hydroxybutanedioate (25.4 g; 66.8 mmol; 1.0 eq.) in THF/water (3/1; 500 mL) was added potassium hydroxide (22.5 g; 400.5 mmol; 6.0 eq.). The reaction mixture was then stirred for 3 days at RT and the organic layer was extracted with an aqueous solution of NaOH (1M). The combined aqueous layers were then washed with MBTE (2×), acidified to pH1 with an aqueous solution of HCl (37%) and extracted with EtOAc. The combined organic phases were dried over MgSO$_4$ and evaporated to give an orange oil (22.9 g). This residue was taken up in an aqueous solution of NaOH (5M, 46 mL). 30 mL of water was then added and the resulting solution was acidified until precipitation of the product (pH 3-4). The product was then filtered to obtain a white solid (10.5 g, 49.6%). This solid was dissolved in an aqueous solution of HCl (1N) and extracted with EtOAc to obtain after evaporation the title product as a white oil (9.77 g; 49.4%) which solidified on standing at RT. $^1$H NMR (DMSO-d$_6$, 300 MHz) δ 12.36 br s (2H), 7.01 (d, J=8.7 Hz, 2H), 6.80 (d, J=8.7 Hz, 2H), 5.42 br s (1H), 4.08 (d, J=5.8 Hz, 1H), 3.90 (q, J=7.0 Hz, 2H), 2.63-2.53 (m, 1H), 2.53-2.42 (m, 2H), 1.61-1.36 (m, 4H), 1.30 (t, J=7.0 Hz, 3H).

Step e) Formation of (2R)-2-[(4S)-2,2-dimethyl-5-oxo-1,3-dioxolan-4-yl]-5-(4-ethoxy phenyl)pentanoic acid To a solution of (2R,3S)-2-[3-(4-ethoxyphenyl)propyl]-3-hydroxybutanedioic acid (3.06 g; 10.33 mmol; 1.0 eq.) in acetone (50.0 mL) was added 2,2-dimethoxypropane (1.8 g; 17.6 mmol; 1.7 eq.) and copper(II) chloride (135 mg; 1.03 mmol; 0.1 eq.). The resulting reaction mixture was stirred for 14 h at RT. The reaction mixture was evaporated and the residue taken up in Et$_2$O. Filtration on a pad of celite gave the title product as a greenish oil used in the next step without further purification. $^1$H NMR (CDCl$_3$, 300 MHz) δ 7.05 (d, J=8.6 Hz, 2H), 6.80 (d, J=8.6 Hz, 2H), 4.48 d (J=5.0 Hz, 1H), 3.98 (q, J=7.0 Hz, 2H), 3.10-2.81 (m, 1H), 2.74-2.41 (m, 3H), 220-1.15 (m, 4H), 1.61 (s, 3H), 1.50 (s, 3H), 1.35 (t, J=7.0 Hz, 3H).

Intermediate 3:
(3R)-3-Methyl-1-pyridin-2-ylpiperazine

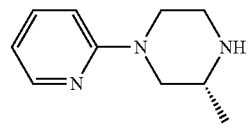

To a solution of (R)-2-methyl piperazine (6.6 g, 0.066 mol) in xylene (100 mL) at 140° C. under nitrogen was added 2-chloro pyridine (4 g, 0.035 mol) slowly over a period of 1 h. The heating was continued for additional 12 h and cooled to RT. The solvent was removed under reduced pressure and the resulting residue was purified by chromatography using chloroform methanol (8/2) as eluent to afford the title product as a liquid (2.5 g, 40%). TLC-Chloroform/MeOH (8/2); R$_f$=0.2. HPLC purity: 97%.

Intermediate 4:
(3S)-3-methyl-1-pyridin-2-ylpiperazine

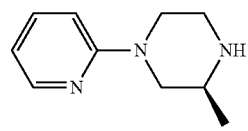

The title compound was prepared following the protocol used for the preparation of Intermediate 3, but starting from (S)-2-methyl piperazine (43%). TLC-Chloroform/MeOH (8/2); R$_f$=0.2.

Intermediate 5:
(3R)-1-(2-fluorophenyl)-3-methylpiperazine

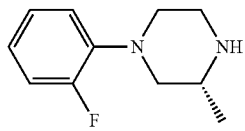

To a mixture of 1-bromo-2-fluorobenzene (5.0 g, 28.5 mmol), (R)-2-methylpiperazine (3.15 g, 31.3 mmol) and sodium-tert-butoxide (4.0 g, 42 mmol) in dry toluene (100 mL) under nitrogen was added Pd(OAc)$_2$ (250 mg, 1.1 mmol) followed by BINAP (750 mg, 1.2 mmol). The reaction mixture was then refluxed for 16 h and cooled. The reaction mixture was washed with water, dried and evaporated to a residue. The residue was purified by chromatography using chloroform/methanol (8/2) as eluent to afford the title compound as a liquid (3.0 g, 55%). TLC-Chloroform/Methanol (9/1); R$_f$: 0.25. HPLC purity: 95%.

Intermediate 6:
(3S)-1-(2-Fluorophenyl)-3-methylpiperazine

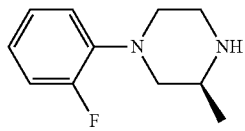

The title compound was prepared following the protocol used for the preparation of Intermediate 5, but starting from (S)-2-methylpiperazine (40%). TLC-Chloroform/Methanol (9/1); R$_f$: 0.25. HPLC purity: 97%.

Intermediate 7:
2-[(3R)-3-methylpiperazin-1-yl]pyrimidine

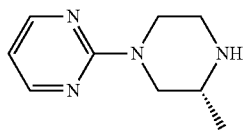

To a solution of (R)-2-methyl piperazine (4.0 g, 40 mmol) in xylene (100 mL) at 140° C. under nitrogen was added 2-bromo pyrimidine (6.36 g, 40 mmol) slowly over a period of 30 min. The heating was continued for additional 15 h and cooled. The solid precipitate was filtered and dried under suction and neutralized with a saturated aqueous solution of sodium bicarbonate. The product was extracted with DCM (2×50 mL), dried and evaporated to afford the title compound as a liquid (2.4 g, 34%). TLC-Chloroform/MeOH (8/2); R$_f$: 0.2.

Intermediate 8:
2-[(3S)-3-methylpiperazin-1-yl]pyrimidine hydrobromide

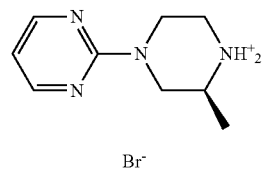

To a solution of (S)-2-methyl piperazine (4.0 g, 40.0 mmol) in xylene (100 mL) at 140° C. under nitrogen was added 2-bromopyrimidine (6.36 g, 40.0 mmol) slowly over a period of 30 min. The heating was continued for additional 15 h and cooled. The solid precipitated was filtered and dried under suction to afford the title compound (4 g, 40%). TLC-Chloroform/MeOH (8/2); R$_f$: 0.15.

Intermediate 9: (3R)-3-Methyl-1-[4-(trifluoromethyl)pyridin-2-yl]piperazine

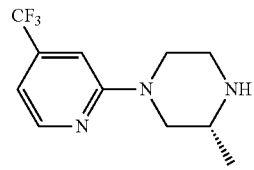

To a solution of (R)-2-methyl piperazine (4.0 g, 40 mmol) in xylene (100 mL) at 140° C. under nitrogen was added 2-chloro-4-trifluoromethylpyridine (726 g, 40.0 mmol) slowly over a period of 30 min. The heating was continued for additional 12 h and cooled. The reaction mixture was evaporated to a residue and the residue was purified by chromatography using chloroform/methanol (8/2) as eluent to afford of the title compound as a liquid (3.5 g, 36%). TLC-Chloroform/MeOH (8/2); R$_f$: 0.25.

Intermediate 11:
1-(5-phenyl-[1,2,4]oxadiazol-3-yl)piperazine dihydrochloride

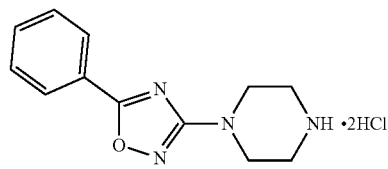

Step a) Formation of tert-butyl 4-cyanopiperazine-1-carboxylate

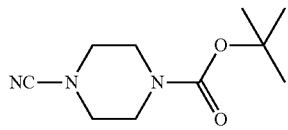

To a solution of 1-Boc-piperazine (25 g, 0.13 mol) in anhydrous DCM (500 mL) at 0° C. was added TEA (52 mL, 0.40 mol) followed by a solution of cyanogen bromide (28.5 g, 0.27 mol) in anhydrous DCM (250 mL) slowly over a period of 30 min. The reaction mixture was stirred at RT for 16 hours and washed with a 10% aqueous solution of sodium bicarbonate, water and brine. The organic layer was dried and the solvent was removed under vacuum. The residue was purified by chromatography using chloroform/methanol (95/5) as eluent to afford 15 g (57%) of the title compound as a solid. TLC-Chloroform/methanol (9/1): R$_f$=0.7.

Step b) Formation of tert-butyl 4-[(hydroxyamino)(imino)methyl]piperazine-1-carboxylate

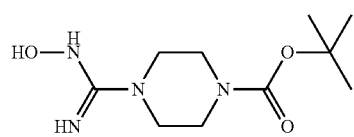

To a solution of tert-butyl 4-cyanopiperazine-1-carboxylate (15 g, 76 mmol) in ethanol (150 mL) was added hydroxylamine (50% aqueous solution, 6.2 mL, 92 mmol) and the reaction mixture was stirred at RT for 6 hours. The solvent was evaporated under vacuum and the solid obtained was triturated with hexane (100 mL) and filtered to obtain 15 g (80%) of the title compound as a solid. TLC-Chloroform/methanol (9/1): R$_f$=0.15.

Step c) Formation of tert-butyl 4-(5-phenyl-1,2,4-oxadiazol-3-yl)piperazine-1-carboxylate

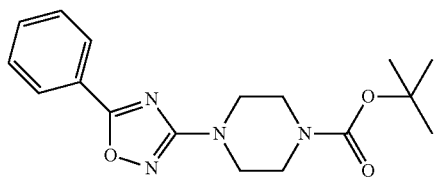

To a solution of tert-butyl 4-[(hydroxyamino)(imino)methyl]piperazine-1-carboxylate (7 g, 28.6 mmol) in anhydrous DCM (150 mL) was added benzoic acid (3.49 g, 28.6 mmol) followed by diisopropyl carbodiimide (DIC, 3.6 g, 28.6 mmol). The reaction mixture was stirred at RT for 8 hours and filtered. The filtrate was evaporated and the residue obtained was refluxed in pyridine (100 mL) for 3 hours. The solvent was removed under vacuum and the residue was dissolved in DCM. The organic layer was washed with a 10% aqueous solution of sodium bicarbonate, water and brine. The organic layer was dried and the solvent was evaporated. The residue was purified by chromatography using petrol ether/EtOAc (9/1) as eluent to afford 5 g (53%) of the title compound as a solid. TLC-Pet ether/EtOAc (9/1): R$_f$=0.7). HPLC purity: 96%.

Step d) Formation of 1-(5-phenyl-1,2,4-oxadiazol-3-yl)piperazine dihydrochloride

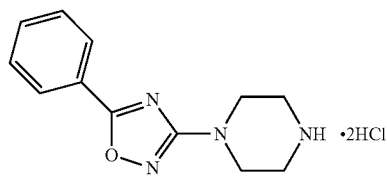

A solution of tert-butyl 4-(5-phenyl-1,2,4-oxadiazol-3-yl)piperazine-1-carboxylate (5 g) in a 2M solution of HCl in ether (100 mL) was stirred at RT for 6 hours. The solvent was removed under vacuum to afford 4.3 g (93%) of the title compound as a solid. TLC-Chloroform/methanol (8/2): R$_f$=0.2. HPLC purity: 97%.

Intermediate 12: 1-(pyridin-4-yl-[1,2,4]oxadiazol-3-yl)-piperazine dihydrochloride

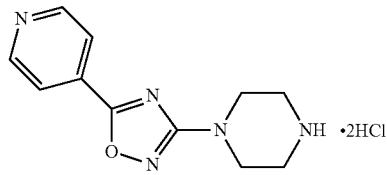

The title product was prepared following the procedure of Intermediate 11 (step a to d) but using isonicotinic acid in step c). The title compound was obtained as a solid. TLC-Chloroform/methanol (8/2): R$_f$=0.2. HPLC purity: 97%.

Intermediate 13: 5-O-benzyl-3-carboxy-3,4-dideoxy-1,2-O-(1-methylethylidene)-L-threo-pentonic acid

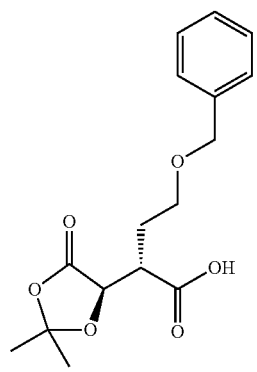

Step a) Formation of isopropyl 5-O-benzyl-3,4-dideoxy-3-(isopropoxycarbonyl)-L-threo-pentonate

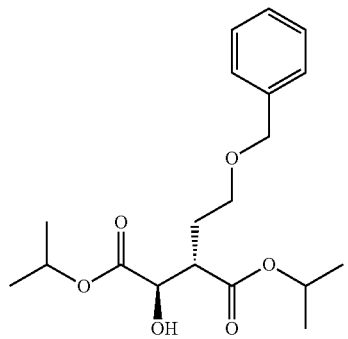

In a 3 necked 250 ml round bottom flask under N$_2$, DIEA (15.0 mL, 100 mmol) and 2,2'-bipyridyl (10 mg) were poured in anhydrous THF (50 ml), cooled to 0° C. and was treated with n-BuLi (3 N, 34 mL, 100 mmol). The resulting solution was stirred at 0° C. for 1 h then cooled further down to −78° C. and to the reaction mixture was added dropwise D-diisopropyl malate (10.0 g, 0.0458 mol) dissolved in dry THF (50 mL). After the addition, the reaction mixture was warmed to −20° C. and then HMPA (16.5 mL, 91 mmol) was added. To the resulting mixture was added 2-iodoethyl phenylmethyl ether (prepared following the protocols described in Mahboobi et al., 1988, *Helv. Chimica Acta*, 71(8), 2034-2041) (13.0 g, 50 mmol) dissolved in anhydrous THF (25 mL) and the reaction mixture was stirred at −20° C. for 1 h and allowed to reach room temperature over night.

The reaction was quenched with an aqueous saturated solution of NH$_4$Cl and then extracted with EtOAc. The aqueous layer was acidified with an aqueous solution of HCl (1.5 N) and was further extracted with EtOAc. The combined organic layers were washed with water, dried over MgSO$_4$, concentrated and then purified by column chromatography to obtain the title intermediate (7.0 g) as a colorless liquid.

Step b) Formation of 3-carboxy-3,4-dideoxy-5-O-(phenylmethyl)-L-threo-pentonic acid

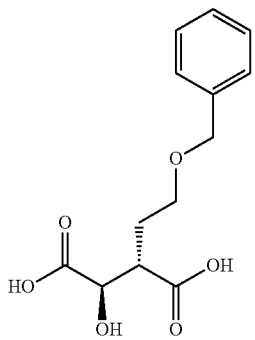

isopropyl 5-O-benzyl-3,4-dideoxy-3-(isopropoxycarbonyl)-L-threo-pentonate (7 g, 19.8 mmol) was taken in THF (50 mL), cooled to 0° C. and was treated with KOH (5.5 g, 99 mmol) in water (50 mL). The resulting mixture was stirred at RT for 3 h. THF was removed and the residue was taken in water. The aqueous layer was washed with ether (100 mL) and was acidified with an aqueous solution of HCl (1.5 N), then was then further extracted with EtOAc (2×100 mL), washed with water, dried over Na$_2$SO$_4$ and then concentrated to give the title product as colorless liquid (3.5 g).

Step c) Formation of 5-O-benzyl-3-carboxy-3,4-dideoxy-1,2-O-(1-methylethylidene)-L-threo-pentonic acid The Intermediate 13 was prepared following the procedure of Intermediate 2 (step e) but starting from 3-carboxy-3,4-dideoxy-5-O-(phenylmethyl)-L-threo-pentonic acid (3.2 g, 11.93 mmol). The crude product (colorless oil, 3.60 g, 98% yield) was used in the next step without any further purification as a mixture of 2 diastereoisomers, 72/28). HPLC (Condition A): Rt: 1.7 min and 1.8 (HPLC purity: 92.4%).

(3S)-3-methyl-1-(4-methylpyridin-2-yl)piperazine, (3R)-1-(2-fluoro-5-methoxyphenyl)-3-methylpiperazine, (3R)-1-(4-chloro-2-fluorophenyl)-3-methylpiperazine, (3R)-1-(5-chloro pyridin-2-yl)-3-methylpiperazine, (3R)-3-methyl-1-(4-trifluoromethoxyphenyl)-piperazine, (3R)-1-biphenyl-4-yl-3-methyl piperazine, (3R)-1-(3-chlorophenyl)-3-methyl piperazine and (3R)-3-methyl-1-(5-phenyl-pyridin-2-yl)piperazine can be obtained from similar protocols by starting from 2-chloro-4-methylpyridine, 2-chloro-1-fluoro-4-methoxy benzene, 1-bromo-4-chloro-2-fluorobenzene, 2,5-dichloropyridine respectively, 1-bromo-4-(trifluoromethoxy)benzene, 4-bromobiphenyl, 1-bromo-3-chlorobenzene and 2-chloro-5-phenylpyridine respectively.

Intermediate 14: 5-fluoro-2-[(3R)-3-methylpiperazin-1-yl]pyrimidine

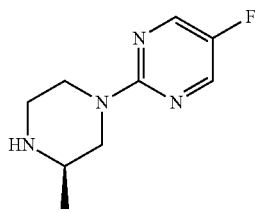

A solution of 2-chloro-5-fluoropyrimidine (239 mg, 1.80 mmol) and (R)-2-methylpiperazine (271 mg, 2.71 mmol) in iPrOH (1 mL) and DIEA (617 µL) was heated in MW at 130° C. for 30 min. Solvent was removed under reduced pressure and the crude (600 mg) was purified by chromatography on silica using DCM/methanol (9/1) as eluent to afford The title compound as a white solid (416 mg, quantitative). TLC-DCM/MeOH (8/2); R$_f$: 0.3. $^1$H NMR (DMSO-d6) δ 8.14 (s, 2H), 4.48 (d, J=13.2 Hz, 2H), 4.33 (brs, 1H), 2.98-3.13 (m, 2H), 2.83 (m, 2H), 2.67 (t, J=12.7 Hz, 1H), 1.20 (m, 3H).

Intermediate 15: (3R)-3-methyl-1-[5-(trifluoromethyl)pyridin-2-yl]piperazine

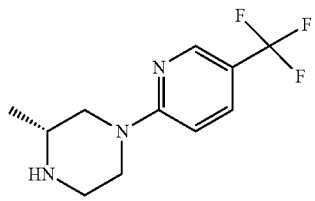

A suspension of 2-bromo-5-trifluoromethyl-pyridine (2.37 g; 10.0 mmol; 1.0 eq.), (R)-2-methylpiperazine (2.00 g; 20.0 mmol; 2.0 eq.) and DIEA (1.94 g; 15.0 mmol; 1.5 eq.) in 4 mL of DMA was heated at 140° C. for 14 h. The mixture was cooled to room temperature. After evaporation of the solvent under vacuum, the residue was dissolved in a 1/1 mixture of DCM/Et$_2$O. A 4N solution of HCl was added (10 mL) then the resulting precipitate was collected and washed with Et$_2$O. The solid was then poured to an aq. solution of NaOH (5N, 20 mL) and the resulting mixture was extracted with Et$_2$O (3×). The combined organic layers were washed with brine, dried over MgSO$_4$, filtered and evaporated to give the title compound as an orange solid (1680 mg, 69%) used without further purification for is the next steps. M$^+$(ESI): 246.3. HPLC (Condition A), Rt: 1.0 min (HPLC purity: 99.9%).

Intermediate 16: 1-(5-bromopyridin-2-yl)piperazine

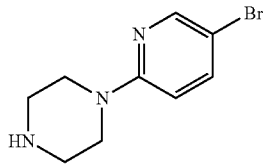

The title compound was prepared following the procedure of the Intermediate 15, but starting from 2,5-dibromopyridine. Purification by chromatography (DCM/MeOH 80/20) gave the title compound as a brown powder (73%). M$^+$(ESI): 244.2. HPLC (Condition A), Rt: 1.1 min (HPLC purity: 79.7%).

Intermediate 17: (3R)-3-methyl-1-(4-propylphenyl)piperazine

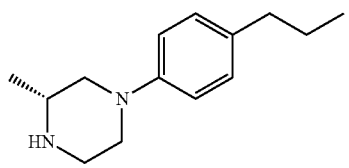

A mixture of (R)-2-methylpiperazine (3.00 g, 30.0 mmol, 1.0 eq), 1-bromo-4-propylbenzene (627 g, 31.5 mmol, 1.05 eq.), (+/−)-BINAP (747 mg, 1.2 mmol, 0.04 eq.) and sodium tert-butoxide (4.32 g, 45.0 mmol, 1.5 eq.) in toluene (70 mL) was degassed for 15 min with N2. Palladium(II) acetate (337 mg, 1.5 mmol, 0.05 eq.) was then added at once. The reaction mixture was then heated to reflux for 16 h then cooled to RT. The mixture was then filtered on a bed of cellite and washed with Et$_2$O. The combined organic layers were then washed with H$_2$O (3×), dried over MgSO$_4$, filtered and evaporated to give a dark to brown oil. This residue was purified by chromatography on silicagel (DCM/MeOH 80/20) to give the title product as yellow oil (2.35 g, 36%). M$^+$(ESI): 2192.

Intermediate 18: (3R)-1-(6-methoxy-2-naphthyl)-3-methylpiperazine

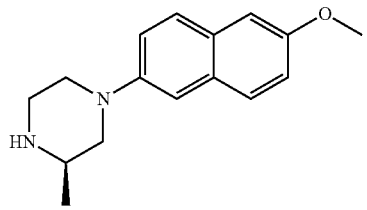

The title compound was prepared following the procedure of Intermediate 17, but starting from 2-bromo-6-methoxynaphthalene. Purification by chromatography (DCM/MeOH 80/20) afforded the title compound as an off white solid (43%). HPLC (Condition A), Rt: 2.2 min (HPLC purity: 98.4%). M$^+$(ESI): 257.2

Intermediate 19: (3R)-1-[4-(1-benzofuran-3-yl)phenyl]-3-methylpiperazine

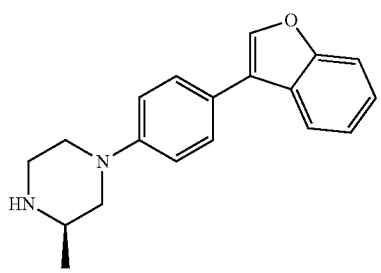

The title compound was prepared following the procedure of Intermediate 17, but starting from 3-(4-bromophenyl)-1-benzofuran (obtained as described in Malamas et al., 2000, *J. Med. Chem.*, 43, 1293-1310). Purification by chromatography (DCM/MeOH 80/20) afforded the title compound as beige solid (21%). HPLC (Condition A), Rt: 3.0 min (HPLC purity: 93.4%). M$^+$(ESI): 293.2

Intermediate 20: (3R)-3-methyl-1-(4-propoxyphenyl)piperazine

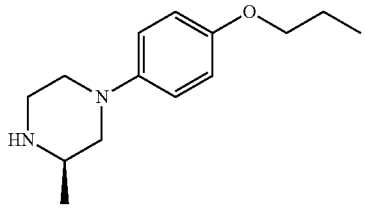

The title compound was prepared following the procedure of Intermediate 17, but starting from 1-bromo-4-propoxybenzene. Purification by chromatography (DCM/MeOH 80/20) afforded the title compound as a brown oil (34%). HPLC (Condition A), Rt: 1.9 min (HPLC purity: 80.2%). M⁺(ESI): 235.2

Intermediate 21: (3R)-3-methyl-1-[4-(trifluoromethyl)phenyl]piperazine

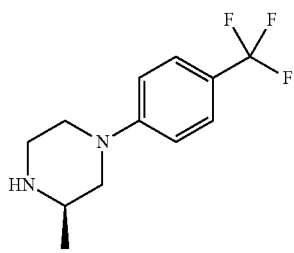

The title compound was prepared following the procedure of Intermediate 5, but starting from 1-bromo-4-trifluoromethylbenzene. Purification by flash chromatography (CHCl₃/MeOH) gave the title compound as a pale yellow solid. M⁺(ESI): 245.2. HPLC (Condition A), Rt: 2.31 min (HPLC purity: 97.5%).

Intermediate 22: (3R)-1-(4'-fluorobiphenyl-4-yl)-3-methylpiperazine

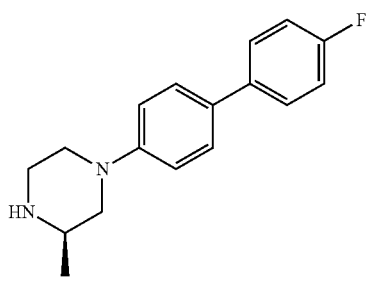

A mixture of (R)-2-methylpiperazine (2.2 g, 22.1 mmol, 1.0 eq.), tris(dibenzylidene acetone)dipalladium(0) (607 mg, 0.66 mmol, 0.03 eq.) and (+/−)-BINAP (137 mg, 0.22 mmol; 0.01 eq.) in toluene was degassed 15 min under N₂. 4-bromo-4'-fluorobiphenyl (4.99 g, 19.9 mmol, 0.90 eq.) was added followed by sodium tert-butoxide (2.97 g, 30.9 mmol, 1.4 eq.). The resulting mixture was heated to 90° C. for 14 h. The reaction was cooled to room temperature, filtered on a bed of cellite and washed with Et₂O. The combined organic layers were then washed with H₂O (3×), dried over MgSO₄, filtered and evaporated to give a dark brown oil. This residue was purified by chromatography on silicagel (DCM/MeOH 20/80) to give the title product as off white solid (3.0 g, 50%) M⁺(ESI): 271.3. HPLC (Condition A), Rt: 2.8 min (HPLC purity: 99.8%).

Intermediate 23: 1-[4-(trifluoromethoxy)phenyl]piperazine, dihydrochloride

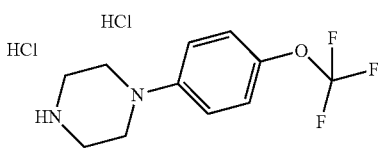

A solution of piperazine (2.0 g, 23.2 mmol), 1-bromo-4-(trifluoromethoxy)benzene (5.6 g, 23.2 mmol) and sodium tert-butoxide (3.3 g, 34.8 mmol) was prepared in anhydrous toluene (50 mL). The solution was degassed by argon bubbling for 10 min. Then palladium(II) acetate (260 mg, 1.16 mmol) and (+/−)-BINAP (580 mg, 0.93 mmol) were added. The resulting mixture was slowly heated from RT to reflux and maintained at reflux for 1 hour. Then the reaction mixture was cooled to RT and concentrated under reduced pressure. The residue was taken up with Et₂O (200 mL), filtrated on Celite and washed with brine. The organic layer was dried (MgSO₄) and the solvent was removed under reduced pressure to give a dark brown oil. Purification by flash chromatography (DCM/MeOH/25% aq. ammonia 80/20/2) gave a brown oil. This oil was taken up with DCM/Et₂O and treated with activated charcoal at RT for 10 min. After filtration on Celite, the solution was concentrated under reduced pressure. Then a solution of HCl 1M in Et₂O (25 mL) was added dropwise. Filtration of the precipitate, washing with Et₂O and drying under reduced pressure gave 2.87 g (39%) of the title compound as a white powder. M⁺(ESI): 247.2. HPLC (Condition A), Rt: 2.4 min (HPLC purity: 98.6%).

Intermediate 24: (3R)-3-methyl-1-[4-(trifluoromethoxy)phenyl]piperazine

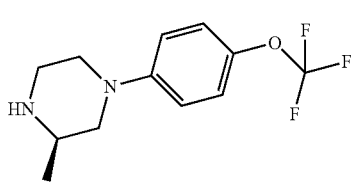

The title compound was prepared following the procedure of Intermediate 20 but starting from (R)-(−)-2-methylpiperazine. Purification by flash chromatography (DCM/MeOH)

gave the title compound as a yellow solid. M⁺(ESI): 261.2. HPLC (Condition A), Rt: 2.3 min (HPLC purity: 100%).

Intermediate 25: (3R)-1-(3,4-dimethoxyphenyl)-3-methylpiperazine

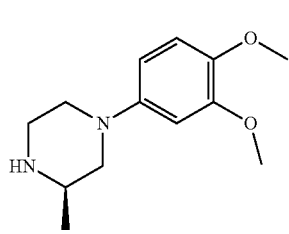

A mixture of (R)-(−)-2-methylpiperazine (2.0 g, 20 mmol), 4-bromo-1,2-dimethoxybenzene (4.33 g, 20 mmol) and sodium tert-butoxide (2.88 g, 30 mmol) was prepared in anhydrous toluene (50 mL). The solution was degassed by argon bubbling for 10 min. Then palladium(II) acetate (220 mg, 1 mmol) and (+/−)-BINAP (500 mg, 0.8 mmol) were added. The resulting mixture was heated at reflux for 4 hours. Then the reaction mixture was cooled to RT and diluted with Et₂O (50 mL). The salts were removed by filtration on Celite and the solvents were removed under reduced pressure to give a dark brown oil. Purification by flash chromatography (CHCl₃/MeOH) gave a brown oil. This oil was taken up with DCM/Et₂O, treated with activated charcoal at RT for 10 min and filtered on Celite. The solvents were removed under reduced pressure to give 1.33 g (28%) of the title compound as a yellow oil. M⁺(ESI): 237.2. HPLC (Condition A), Rt: 1.2 min (HPLC purity: 93.2%).

Intermediate 26: (3R)-3-methyl-[4-(methylsulfonyl)phenyl]piperazine

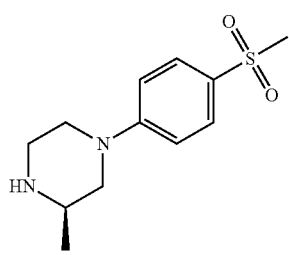

A mixture of 4-fluorophenyl methyl sulfone (2.00 g), (R)-2-methylpiperazine (2.30 g) and K₂CO₃ (3.20 g) in anhydrous DMF (80 mL) was heated at 100° C. for 5 hours. The reaction mixture was filtered to remove salts and the solvent was evaporated under reduced pressure to give a yellow oil. Purification by flash chromatography (CHCl₃/MeOH) gave 1.36 g (47%) of the title compound as a pale yellow solid. M⁺(ESI): 255.2. HPLC (Condition A), Rt: 1.0 min (HPLC purity: 100%).

Intermediate 27: (3R)-1-(2,3-dihydro-1-benzofuran-5-yl)-3-methylpiperazine

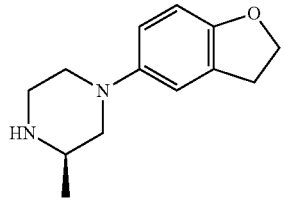

The title compound was prepared following the procedure of Intermediate 25, but starting from 5-bromo-2,3-dihydrobenzo[b]furan. Purification by flash chromatography (CHCl₃/MeOH) gave the title compound as a brown oil. M⁺(ESI): 219.2. HPLC (Condition A), Rt: 1.3 min (HPLC purity: 99.9%).

Intermediate 28: (3R)-1-(1,3-benzodioxol-5-yl)-3-methylpiperazine

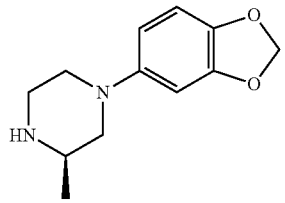

The title compound was prepared following the procedure of Intermediate 25, but starting from 4-bromo-1,2-(methylenedioxy)benzene. Purification by flash chromatography (CHCl₃/MeOH) gave the title compound as a yellow oil. M⁺(ESI): 221.2. HPLC (Condition A), Rt: 1.3 min (HPLC purity: 100%).

Intermediate 29: (3R)-1-(4-methoxyphenyl)-3-methylpiperazine

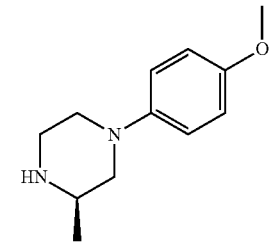

The title compound was prepared following the procedure of Intermediate 25, but starting from 1-bromo-4-methoxybenzene. Purification by flash chromatography (CHCl₃/

MeOH) gave the title compound as a yellow oil. M⁺(ESI): 207.2. HPLC (Condition A), Rt: 1.2 min (HPLC purity: 922%).

Intermediate 30: (3R)-3-methyl-1-{4-[(trifluoromethyl)sulfonyl]phenyl}piperazine

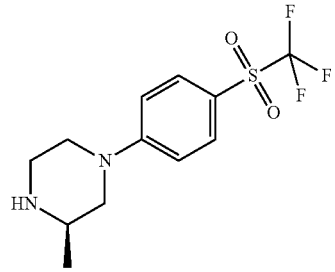

The title compound was prepared following the procedure of Intermediate 26, but starting from 1-chloro-4-(trifluoromethanesulfonyl)benzene. Purification by flash chromatography (CHCl₃/MeOH) gave the title compound as a pale yellow solid. M⁺(ESI): 309.2. HPLC (Condition A), Rt: 2.3 min (HPLC purity: 99.5%).

Intermediate 31: (3R)-1-(4-tert-butylphenyl)-3-methylpiperazine

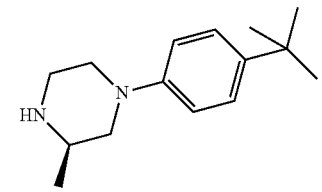

The title compound was prepared following the procedure of Intermediate 5 but starting from 1-bromo-4-tert-butylbenzene. Purification by chromatography using dichloromethane/methanol (8/2) as eluent afforded The title compound as a liquid (1.5 g, 27%). M⁺(ESI): 233.3. HPLC (Condition A), Rt: 2.8 min (HPLC purity: 96.6%).

Intermediate 32: (3R)-1-(4-ethoxyphenyl)-3-methylpiperazine

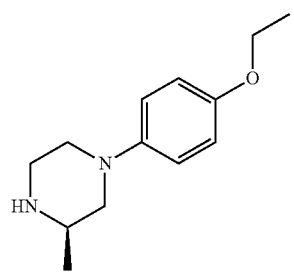

The title compound was prepared following the procedure of Intermediate 22 but starting from 1-bromo-4-ethoxybenzene. Purification by flash chromatography (CHCl₃/MeOH) gave the title compound as a brown solid. M⁺(ESI): 221.3. HPLC (Condition A), Rt: 1.5 min (HPLC purity: 97.6%).

Intermediate 33: (3R)-1-(4-chlorophenyl)-3-methylpiperazine

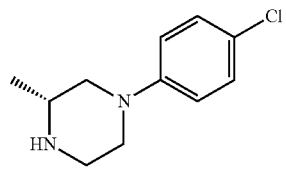

The title compound was prepared following the procedure of Intermediate 22 but starting from 1-bromo-4-chlorobenzene. Purification by flash chromatography (CHCl₃/MeOH) gave the title compound as a beige solid. M⁺(ESI): 211.2. HPLC purity: >96%).

Intermediate 34: 1-[5-(2-thienyl)-1,2,4-oxadiazol-3-yl]piperazine, dihydrochloride Step a) tert-Butyl 4-cyanopiperazine-1-carboxylate

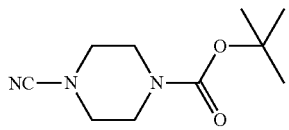

To a cold (0° C.) solution of 1-Boc-piperazine (25 g, 0.13 mol) in dry dichloromethane (500 mL) was added TEA (52 mL, 0.40 mol) followed by a solution of cyanogen bromide (28.5 g, 0.27 mol) in anhydrous DCM (250 mL) over a period of 30 min. The reaction mixture was stirred at RT for 16 hours, then washed with a 10% aq. solution of sodium bicarbonate, water, brine and dried. The solvent was removed under vacuum and the residue was purified by flash chromatography (CHCl₃/MeOH 95/5) to give 15 g (57%) of The title compound as a solid. TLC-CHCl₃/MeOH (9/1): R$_f$=0.7.

Step b) tert-Butyl 4-[(hydroxyamino)(imino)methyl]piperazine-1-carboxylate

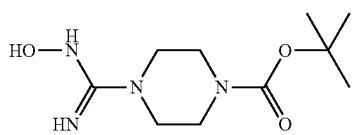

To a solution of tert-butyl 4-cyanopiperazine-1-carboxylate (15 g, 76 mmol) in EtOH (150 mL) was added hydroxylamine (50% aqueous solution, 6.2 mL, 92 mmol) and the reaction mixture was stirred at RT for 6 hours. The solvent was evaporated under vacuum. The residue was triturated with hexane (100 mL) and filtered to give 15 g (80%) of The title compound as a solid. TLC-CHCl$_3$/MeOH (9/1): R$_f$=0.15.

Step c) tert-Butyl 4-[5-(2-thienyl)-1,2,4-oxadiazol-3-yl]piperazine-1-carboxylate

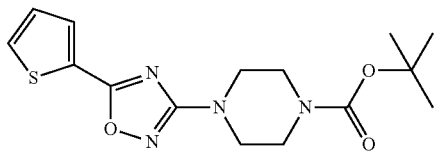

To a cold (0° C.) solution of tert-butyl 4-[(hydroxyamino)(imino)methyl]piperazine-1-carboxylate (8 g, 32.7 mmol) in anhydrous DCM (150 mL) was added thiophene-2-carbonyl chloride (4.8 g, 32.7 mmol) followed by DIEA (7.2 mL, 39.2 mmol). The reaction mixture was stirred at RT for 12 hours and then filtered. The filtrate was evaporated and the residue was refluxed in pyridine (100 mL) for 3 hours. The solvent was removed under vacuum and the residue was dissolved in DCM. The organic layer was washed with a 10% aq. solution of sodium bicarbonate, water, brine and dried. The solvent was concentrated and the residue was purified by chromatography (Pet. Ether/EtOAc 7/3) to give 2.2 g (20%) of The title compound as a solid. TLC-Pet ether/EtOAc (9/1): R$_f$=0.75. HPLC purity>97%.

Step d) 1-(5-(2-thienyl)-1,2,4-oxadiazol-3-yl)piperazine, dihydrochloride

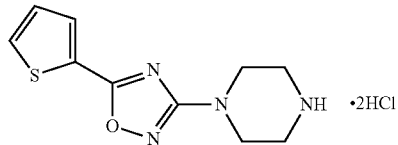

A solution of tert-butyl 4-(5-(2-thienyl)-1,2,4-oxadiazol-3-yl)piperazine-1-carboxylate (2.2 g) in 2M HCl in Et$_2$O (50 mL) was stirred at RT for 6 hours. The solvent was removed under vacuum to give 1.6 g (78%) of The title compound as a solid. TLC-CHCl$_3$/MeOH (8/2): R$_f$=0.2. HPLC purity>98%.

(3S)-3-methyl-1-(4-methylpyridin-2-yl)piperazine, (3R)-1-(2-fluoro-5-methoxyphenyl)-3-methylpiperazine, (3R)-1-(4-chloro-2-fluorophenyl)-3-methylpiperazine, (3R)-1-(5-chloro pyridin-2-yl)-3-methylpiperazine, (3R)-1-biphenyl-4-yl-3-methyl-piperazine, (3R)-1-(3-chlorophenyl)-3-methyl piperazine and (3R)-3-methyl-1-(5-phenyl-pyridin-2-yl)piperazine, (3R)-1-(4-cyclohexylphenyl)-3-methylpiperazine, (3R)-1-(1-benzofuran-5-yl)-3-methyl piperazine, (3R)-1-(2,2-difluoro-1,3-benzodioxol-5-yl)-3-methylpiperazine, (3R)-1-(3-fluoro-4-methoxyphenyl)-3-methylpiperazine, (3R)-1-(3-fluoro-4-isopropoxyphenyl)-3-methylpiperazine, (3R)-1-[3-fluoro-4-(trifluoromethoxy)phenyl]-3-methylpiperazine, 3-[(3R)-3-methylpiperazin-1-yl]quinoline, and (3R)-1-(5-chloro-2-thienyl)-3-methyl piperazine can be obtained from similar protocols by starting from 2-chloro-4-methyl pyridine, 2-chloro-1-fluoro-4-methoxy benzene, 1-bromo-4-chloro-2-fluorobenzene, 2,5-di chloropyridine, 4-bromobiphenyl, 1-bromo-3-chlorobenzene, 2-chloro-5-phenylpyridine, 1-bromo-4-cyclohexylbenzene, 5-bromo-1-benzofuran, 5-bromo-2,2-difluoro-1,3-benzodioxole, 4-bromo-2-fluoro-1-methoxybenzene, 4-bromo-2-fluoro-1-isopropoxy benzene, 4-bromo-2-fluoro-1-(trifluoromethoxy)benzene, 3-bromoquinoline, and 2-bromo-5-chlorothiophene respectively.

Intermediate 35: Formation of (2R)-2-[(4S)-2,2-dimethyl-5-oxo-1,3-dioxolan-4-yl]propanoic acid

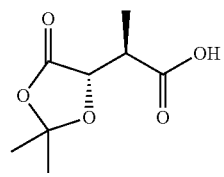

Step a) Formation of di-isopropyl (2S,3R)-2-methyl-3-hydroxybutanedioate

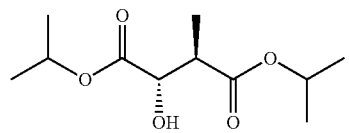

To a cold (−78° C.) solution of diisopropyl-(S)-(−)-malate (4.72 mL, 22.9 mmol, 1 eq.) in anhydrous THF (8.50 mL) was added slowly a solution (1 M) of lithium bis(trimethylsilyl)amide (48.1 mL, 48.1 mmol, 2.10 eq.) in THF. The temperature was raised to 20° C. over 30 minutes, than lowered again to −78° C. Iodomethane (1.7 mL, 28 mmol, 1.20 eq.) was added and the mixture stirred at RT for 16 hours. The reaction mixture was then cooled to 0° C. and a saturated solution of NH$_4$Cl was added. The resulting mixture was diluted with water, extracted three times with EtOAc. The combined organic phases were washed with brine, dried over MgSO$_4$, filtered and evaporated under reduced pressure. The residue was then purified by chromatography (SiO$_2$, 20/80 EtOAc/c-hex) to give the product (mixture of diatereoisomers) as a colourless oil (3.77 g, 71%).

Step b) Formation of (2S,3R)-2-hydroxy-3-methylsuccinic acid

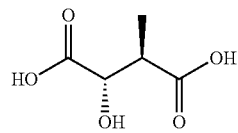

Diisopropyl (2S,3R)-2-hydroxy-3-methylsuccinate (3.70 g; 15.93 mmol; 1.0 eq.) was taken in THF (55 mL), cooled to 0° C. and treated with KOH (5.36 g, 96 mmol) in water (18.5 mL). The resulting mixture was stirred at RT for 48 h. THF was removed and the residue to was taken in water. The aqueous layer was washed with Et$_2$O (100 mL) and was acidified with an aqueous solution of HCl (1.5 N), then was extracted with EtOAc (continuous extraction during 20 hours). The organic phase was dried over Na$_2$SO$_4$ and then concentrated to give the title product (mixture of diastereoisomers) as pale yellow oil (2.4 g, quant.).

Step c) Formation of (2R)-2-[(4S)-2,2-dimethyl-5-oxo-1,3-dioxolan-4-yl]propanoic acid To a solution of (2S,3R)-2-hydroxy-3-methylsuccinic acid (2.40 g; 16.2 mmol; 1.0 eq.) in acetone (80.0 mL) was added 2,2-dimethoxypropane (3.98 g; 32.4 mmol; 2.0 eq.) and copper(II) chloride (218 mg; 1.62 mmol; 0.1 eq.). The resulting reaction mixture was stirred for 4 h at RT. The reaction mixture was evaporated and the residue taken up in CHCl$_3$. Activated charcoal is added and the resulting mixture stirred for one hour. Filtration on a pad of celite gave the title product (mixture of diastereoisomers) as a greenish oil (2.48 g, 82%) used in the next step without further purification.

Intermediate 36: (2S)-2-[(4R)-2,2-dimethyl-5-oxo-1,3-dioxolan-4-yl]propanoic acid

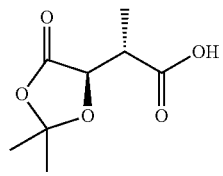

Step a) Formation of di-isopropyl (2R,3S)-2-methyl-3-hydroxybutanedioate

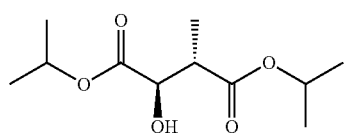

To a cold (−78° C.) solution of diisopropyl-(R)-(+)-malate (9.4 mL; 45.8 mmol; 1.0 eq.) in anhydrous THF (17 mL) was added slowly a solution (1 M) of lithium bis(trimethylsilyl) amide (96.2 mL; 1.00 M; 96.2 mmol; 2.1 eq.) in THF. The temperature was raised to 20° C. over 30 minutes, than lowered again to −78° C. Iodomethane (3.4 mL; 55.0 mmol; 1.2 eq.) was added and the mixture stirred at RT for 16 hours. The reaction to mixture was then cooled to 0° C. and a saturated solution of NH$_4$Cl was added. The resulting mixture was diluted with water, extracted three times with EtOAc. The combined organic layers were washed with brine and dried over MgSO$_4$, filtered and evaporated under reduced pressure. The residue was then purified by chromatography (SiO$_2$, 20/80 EtOAc/c-hex) to give the product (mixture of diastereoisomers) as a colourless oil (9.80 g, 92%).

Step b) Formation of (2R,3S)-2-hydroxy-3-methylsuccinic acid

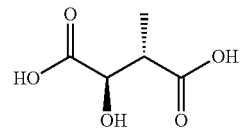

Diisopropyl (2R,3S)-2-hydroxy-3-methylsuccinate (9.75 g; 42.0 mmol; 1.00 eq.) was taken in THF (146 mL), cooled to 0° C. and was treated with KOH (14.1 g, 152 mmol) in water (49 mL). The resulting mixture was stirred at RT for 48 h. THF was removed and the residue was taken in water. The aqueous layer was washed with ether (100 mL) and was acidified with an aqueous solution of HCl (1.5 N), then was extracted with EtOAc (continuous extraction during 20 hours). The organic phase was dried over Na$_2$SO$_4$ and then concentrated to give the title product (mixture of diastereoisomers) as a pale yellow oil (2.49 g).

Step c) Formation of (2S)-2-[(4R)-2,2-dimethyl-5-oxo-1,3-dioxolan-4-yl]propanoic acid To a solution of (2R,3S)-2-hydroxy-3-methylsuccinic acid (2.48 g; 16.8 mmol; 1.0 eq.) in acetone (80.0 mL) was added 2,2-dimethoxypropane (4.13 g; 33.6 mmol; 2.0 eq.) and copper(II) chloride (226 mg; 1.68 mmol; 0.1 eq.). The resulting reaction mixture was stirred for 16 h at RT. The reaction mixture was evaporated and the residue taken up in CHCl$_3$. Activated charcoal is added and the resulting mixture stirred for one hour. Filtration on a pad of celite gave the title product (mixture of diatereoisomers) as a greenish oil (1.85 g, 59%) used in the next step without further purification.

Intermediate 37: Formation of (2R)-2-[(4S)-2,2-dimethyl-5-oxo-1,3-dioxolan-4-yl]-3-phenylpropanoic acid

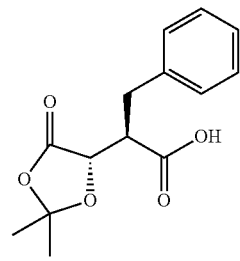

Step a) Formation of Diisopropyl (2R,3S)-2-benzyl-3-hydroxysuccinate

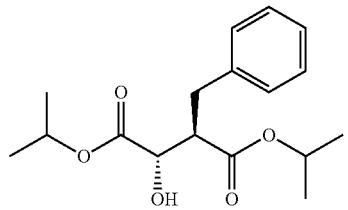

To a cold (−78° C.) solution of diisopropyl-(S)-(−)-malate (4.72 mL, 22.9 mmol, 1 eq.) in anhydrous THF (8.50 mL) was added slowly a solution (1 M) of lithium bis(trimethylsilyl) amide (48.1 mL, 48.1 eq., 2.10 eq.) in tetrahydrofuran. The temperature was raised to 20° C. over 30 minutes, than lowered again to −78° C. Benzyl bromide (4.70 g; 27.5 mmol; 1.20 eq.) was added and the mixture stirred at RT for 16 hours. The reaction mixture was then cooled to 0° C. and a saturated solution of NH$_4$Cl was added. The resulting mixture was diluted with water, extracted three times with EtOAc. The combined organic layers were washed with brine and dried over MgSO$_4$, filtered and evaporated under reduced pressure. The residue was then purified by chromatography (SiO$_2$, 20/80 EtOAc/c-hex) to give the product as a colourless oil (3.00 g, 42%).

Step b) Formation of (2R,3S)-2-benzyl-3-hydroxysuccinic acid

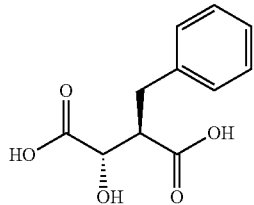

Diisopropyl (2R,3S)-2-benzyl-3-hydroxysuccinate (2.90 g; 15.9 mmol; 1.0 eq.) was taken in TIM (44 mL), cooled to 0° C. and was treated with KOH (3.17 g, 56.4 mmol) in water (14.5 mL). The resulting mixture was stirred at RT for 48 h. Tiff was removed and the residue was taken in water. The aqueous layer was washed with ether (100 mL) and was acidified with an aqueous solution of HCl (1.5 N), then was extracted with EtOAc. The combined organic layers were dried over Na$_2$SO$_4$ and then concentrated to give the title product as white solid (1.73 g, 82%).

Step c) (2R)-2-[(4S)-2,2-dimethyl-5-oxo-1,3-dioxolan-4-yl]-3-phenylpropanoic acid To a solution of (2R,3S)-2-benzyl-3-hydroxysuccinic acid (1.70 g; 7.58 mmol; 1.0 eq.) in acetone (50.0 mL) was added 2,2-dimethoxypropane (1.86 g; 15.2 mmol; 2.0 eq.) and copper(II) chloride (102 mg; 0.76 mmol; 0.1 eq.). The resulting reaction mixture was stirred for 2 h at RT. The reaction mixture was evaporated and the residue taken up in CHCl$_3$. Activated charcoal is added and the resulting mixture stirred for one hour. Filtration on a pad of celite gave the title product as a greenish oil (1.46 g) used in the next step without further purification.

Intermediate 38: Formation of (2S)-2-[(4R)-2,2-dimethyl-5-oxo-1,3-dioxolan-4-yl]-3-phenylpropanoic acid

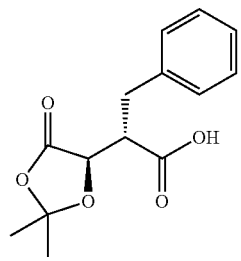

Step a) Formation of Diisopropyl (2S,3R)-2-benzyl-3-hydroxysuccinate

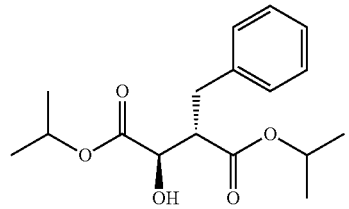

To a cold (−78° C.) solution of diisopropyl-(R)-(+)-malate (9.4 mL; 45.82 mmol; 1.00 eq.) in anhydrous THF (17 mL) was added slowly a solution (1 M) of lithium bis(trimethylsilyl)amide (96.2 mL; 1.00 M; 96.2 mmol; 2.10 eq.) in THF. The temperature was raised to 20° C. over 30 minutes, than lowered again to −78° C. Benzyl bromide (9.40 g; 55.0 mmol; 1.20 eq.) was added and the mixture stirred at RT for 16 hours. The reaction mixture was then cooled to 0° C. and a saturated solution of NH$_4$Cl was added. The resulting mixture was diluted with water, extracted three times with EtOAc. The combined organic layers were washed with brine and dried over MgSO$_4$, filtered and evaporated under reduced pressure. The residue was then purified by chromatography (SiO$_2$, 20/80 EtOAc/c-hex) to give the product as a colourless oil (9.76 g, 69%).

Step b) (2R,3S)-2-benzyl-3-hydroxysuccinic acid

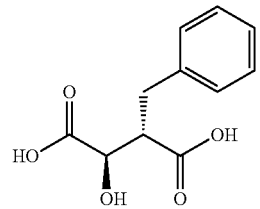

Diisopropyl (2S,3R)-2-benzyl-3-hydroxysuccinate (9.76 g; 31.65 mmol; 1.00 eq.) was taken in THF (150 mL), cooled to 0° C. and was treated with KOH (10.65 g; 189.90 mmol; 6.00 eq.) in water (50 mL). The resulting mixture was stirred at RT for 48 h. THF was removed and the residue was taken in water. The aqueous layer was washed with ether (100 mL) and was chilled to 0° C. and cautiously acidified with an aqueous solution of HCl (1 N) until pH 3.8. The solid that separated was collected by filtration to give the title product (single diastereoisomer) as white solid (2.08 g, 29%).

Step c) Formation of (2S)-2-[(4R)-2,2-dimethyl-5-oxo-1,3-dioxolan-4-yl]-3-phenylpropanoic acid To a solution of (2R,3S)-2-benzyl-3-hydroxysuccinic acid (2.08 g; 9.28 mmol; 1.00 eq.) in acetone (50.0 mL) was added 2,2-dimethoxypropane (2.3 mL; 18.55 mmol; 2.0 eq.) and copper(II) chloride (124.73 mg; 0.93 mmol; 0.10 eq.). The resulting reaction mixture was stirred for 4 h at RT. The reaction mixture was evaporated and the residue taken up in CHCl₃. Activated charcoal is added and the resulting mixture stirred for one hour. Filtration on a pad of celite gave the title product (single diastereoisomer) as a greenish oil (1.81 g, 74%) used in the next step without further purification.

Intermediate 39: Formation of (2R)-3-cyclopentyl-2-[(4S)-2,2-dimethyl-5-oxo-1,3-dioxolan-4-yl]propanoic acid

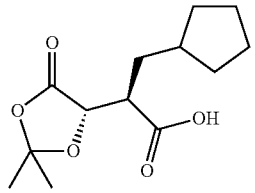

Step a) Formation of diisopropyl (2R,3S)-2-(cyclopentylmethyl)-3-hydroxysuccinate

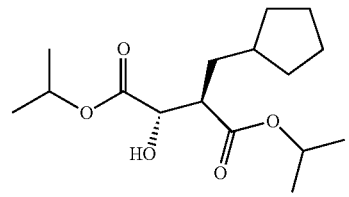

To a cold (5° C.) solution of diisopropyl-(S)-(−)-malate (50.0 g, 229.1 mmol, 1.0 eq.) and (iodomethyl)cyclopentane (55.6 g, 264.6 mmol, 1.15 eq.) in anhydrous THF (250 mL) under N₂ was added over a period of 90 min. a solution (1M) of lithium bis(trimethylsilyl)amide (481 mL; 1.0 M, 481.1 mmol, 2.1 eq.) in THF. The temperature was allowed to warm to 20° C. and the mixture was stirred for 15 hours until completion (monitoring by TLC (SiO₂); cyclohexane 8-ethyl acetate 2; treated with molibdic acid).

Step b) Formation of (2R,3S)-2-(cyclopentylmethyl)-3-hydroxysuccinic acid

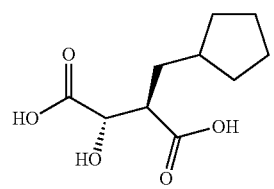

A solution of potassium hydroxide (183.2 mL; 5.0 M; 916.4 mmol, 4.0 eq.) in water was added to the previous reaction mixture and the solution was stirred at RT over 3 days. MTBE (200 mL) was added to the reaction mixture and after 5 minutes under stirring, layers were separated and organic phase was extracted with potassium hydroxide 1N (4×100 mL). Combined aqueous layers were washed with MTBE (2×150 mL) and cooled to 5° C. under stirring. Then concentrated hydrochloric acid was added dropwise until pH=3.9. After 30 minutes under stirring at 5° C., resulting suspension was filtered to give first crop of the half potassium salt as a white powder (12.88 g, 22%). Filtrate was saturated with sodium chloride avoiding super saturation (no solid sodium chloride visible in solution) and precipitation was observed, filtration was done to give second crop of the half potassium salt as a white solid (9.86 g, 17%). Batches were combined, taken up in 200 mL of hydrochloric acid and extracted with ethyl acetate (150 mL). After phase separation, aqueous phase was saturated with sodium chloride and extracted with ethyl acetate (150 mL). This loop was repeated twice then combined organic phase were dried over MgSO₄, filtered and concentrated to give the title product as an orange solid (18.97 g, 38%)

Step c) Formation of (2R)-3-cyclopentyl-2-[(4S)-2,2-dimethyl-5-oxo-1,3-dioxolan-4-yl]propanoic acid

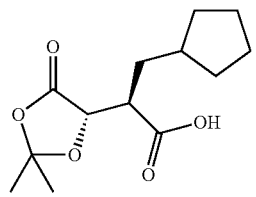

To a solution of (2R,3S)-2-(cyclopentylmethyl)-3-hydroxysuccinic acid (18.97 g, 87.73 mmol; 1.0 eq.) in acetone (300 mL) was added 2,2-dimethoxypropane (21.6 mL, 175.46 mmol, 2.0 eq.) and copper (II) chloride (1.18 g; 8.77 mmol, 0.1 eq.). The resulting reaction mixture was stirred for 16 h at RT. The reaction mixture was evaporated and the residue taken up in CHCl₃ (200 mL). Activated charcoal (10 g) was added and the resulting mixture was stirred at RT for 30 minutes. Filtration on a pad of celite gave the title product as yellowish oil. Purification by flash chromatography (Si60;

Example 1

(2S,3S)-N,2-dihydroxy-5-methyl-3-{[4-(2-pyridinyl)-1-piperazinyl]carbonyl}hexanamide (1)

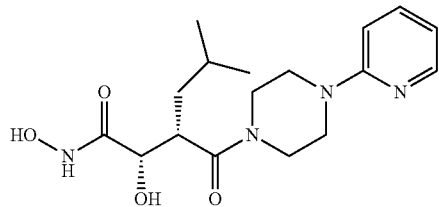
(1)

Step a) Formation of (5S)-2,2-dimethyl-5-((1S)-3-methyl-1-{[4-(2-pyridinyl)-1-piperazinyl]carbonyl}butyl)-1,3-dioxolan-4-one

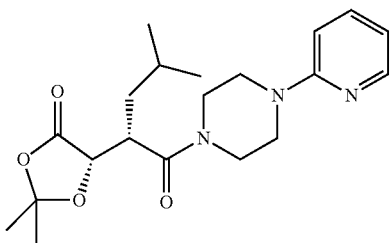

To a solution of a 55/45 diastereoisomeric mixture of pentafluorophenyl (2S)-2-[(4S)-2,2-dimethyl-5-oxo-1,3-dioxolan-4-yl]-4-methylpentanoate and pentafluorophenyl (2R)-2-[(4S)-2,2-dimethyl-5-oxo-1,3-dioxolan-4-yl]-4-methylpentanoate (Intermediate 1, 792.6 mg; 2.0 mmol; 1.0 eq.) in DMF (15 mL) was added 1-(2-pyridyl)piperazine (326.5 mg; 2.0 mmol; 1.0 eq.). After 14 h of reaction at RT, the solvent was evaporated to give an oil. Purification by chromatography (SiO$_2$) gave the title compound as a colorless oil (as a mixture of 2 diastereoisomers 50/50). This product was dissolved on iPrOH (10 mL) at kept at −20° C. for 48 h. The supernatant was collected and evaporated to give a colorless oil (301 mg, 40%, single diastereoisomer). M$^+$(ESI): 3763. HPLC (Condition A): Rt: 5.0 min (HPLC purity: 77.1%). $^1$H NMR (CDCl$_3$, 300 MHz) δ 822 (d, J=4.2 Hz, 1H), 7.58-7.47 (m, 1H), 6.74-6.63 (m, 2H), 4.54 (d, J=6.0 Hz, 1H), 3.88-3.41 (m, 8H), 3.33-322 (m, 1H), 1.89-1.62 (m, 3H), 1.61 (s, 3H), 1.55 (s, 3H), 0.99-0.88 (m, 6H).

Step b) Formation of (2S,3S)-N,2-dihydroxy-5-methyl-3-{[4-(2-pyridinyl)-1-piperazinyl]carbonyl}hexanamide To a solution of (5S)-2,2-dimethyl-5-((1S)-3-methyl-1-{[4-(2-pyridinyl)-1-piperazinyl]carbonyl}butyl)-1,3-dioxolan-4-one (250 mg; 0.67 mmol; 1.0 eq.) in iPrOH (5 mL) was added an aqueous solution of hydroxylamine (50%; 0.195 mL; 3.35 mmol; 5.0 eq.) and the resulting reaction mixture was stirred at RT for 2.5 h. After evaporation of the solvents, the crude mixture was purified by reverse-phase chromatography to give the title compound (1) as a white powder (74 mg; 31%). M$^-$(ESI): 349.2; M$^+$(ESI): 351.1. HPLC: Rt: 1.3 min (HPLC purity: 100%).

Example 2

(2S,3S)-N,2-dihydroxy-5-methyl-3-{[4-(3-phenyl-1,2,4-thiadiazol-5-yl)-1-piperazinyl]carbonyl}hexanamide (2)

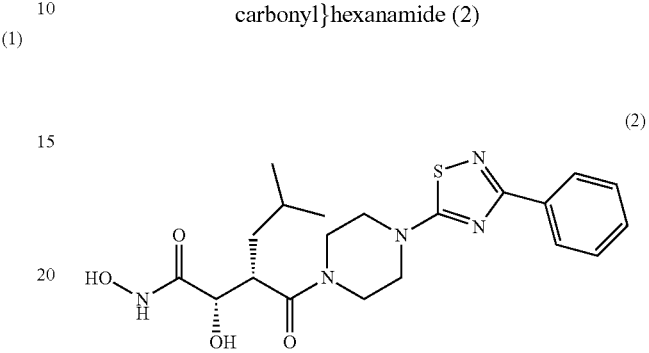
(2)

Step a) Formation of (5S)-2,2-dimethyl-5-((1S)-3-methyl-1-{[4-(3-phenyl-1,2,4-thiadiazol-5-yl)-1-piperazinyl]carbonyl}butyl)-1,3-dioxolan-4-one

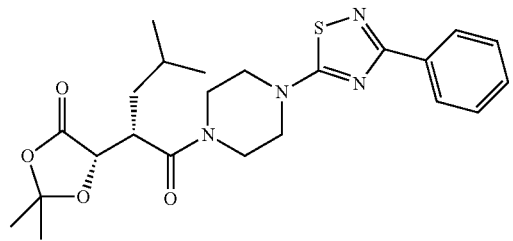

To a solution of a 55/45 diastereoisomeric mixture of pentafluorophenyl (2S)-2-[(4S)-2,2-dimethyl-5-oxo-1,3-dioxolan-4-yl]-4-methylpentanoate and pentafluorophenyl (2R)-2-[(4S)-2,2-dimethyl-5-oxo-1,3-dioxolan-4-yl]-4-methylpentanoate (Intermediate 1; 150.0 mg; 0.38 mmol; 1.0 eq.) in DMF (1.5 mL) was added 3-phenyl-5-piperazino-1,2,4-thiadiazole (93.2 mg; 0.38 mmol; 1.0 eq.) and the resulting reaction mixture was stirred at RT for 14 h. An aqueous solution of HCl (1N) was added and the resulting mixture was extracted with EtOAc, dried over MgSO$_4$, filtered and evaporated to give an oil. This residue was taken up in CD$_3$OD. The precipitate was filtered off and the mother liquids were evaporated and the resulting residue was then purified by chromatography (SiO$_2$, gradient from 2/1 to 1/1 c-hex/EtOAc in about 30 min) to give the title product as a colorless oil (10 mg; 5.8%). M$^+$(ESI): 459.0. HPLC (Condition A): Rt: 4.5 min (HPLC purity: 98.5%).

Step b) Formation of (2S,3S)-N,2-dihydroxy-5-methyl-3-{[4-(3-phenyl-1,2,4-thiadiazol-5-yl)-1-piperazinyl]carbonyl}hexanamide To a solution of (5S)-2,2-dimethyl-5-((1S)-3-methyl-1-{[4-(3-phenyl-1,2,4-thiadiazol-5-yl)-1-piperazinyl]carbonyl}butyl)-1,3-dioxolan-4-one (9.0 mg; 0.019 mmol; 1.0 eq.) in iPrOH (0.20 mL) was added an aqueous solution of hydroxylamine (50%; 0.0029 mL; 0.098 mmol; 5.0 eq.) and the resulting reaction mixture was stirred at RT for 2 h. Evaporation of the solvents gave the title product (2) as a colorless oil (9 mg; 100%). M⁻(ESI): 432.1; M⁺(ESI): 434.3. HPLC (Condition A): Rt: 3.1 min (HPLC purity: 79.3%).

Example 3

(2S,3S)-N,2-dihydroxy-5-methyl-3-({(2R)-2-methyl-4-[4-(trifluoromethyl)pyridin-2-yl]piperazin-1-yl}carbonyl)hexanamide (3)

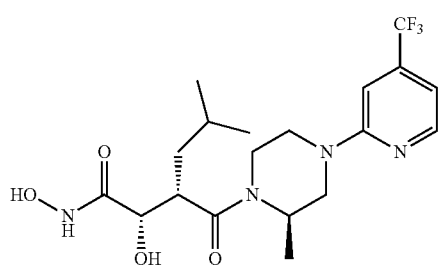

(3)

Step a) Formation of (5S)-2,2-dimethyl-5-[(1S)-3-methyl-1-({(2R)-2-methyl-4-[4-(trifluoromethyl)pyridin-2-yl]piperazin-1-yl}carbonyl)butyl]-1,3-dioxolan-4-one

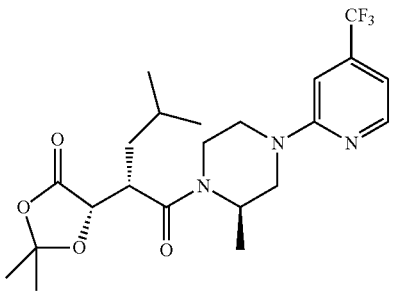

To a 55/45 diastereoisomeric mixture of pentafluorophenyl (2S)-2-[(4S)-2,2-dimethyl-5-oxo-1,3-dioxolan-4-yl]-4-methylpentanoate and pentafluorophenyl (2R)-2-[(4S)-2,2-dimethyl-5-oxo-1,3-dioxolan-4-yl]-4-methylpentanoate (Intermediate 1, 484.8 mg; 1.22 mmol; 1.0 eq.) and triethylamine (339.13 µl; 2.45 mmol; 2.0 eq.) in DMF (10.0 mL) was added (3R)-3-methyl-[4-(trifluoromethyl)pyridin-2-yl]piperazine (Intermediate 9, 300 mg; 1.22 mmol; 1.0 eq.). After 14 h of reaction at RT, the solvent was evaporated and the residue dissolved in ether and extracted with water (3×). The combined organic layers were dried and evaporated to give an oil. This residue was purified by chromatography to give the title product (170 mg; 30.4% as a mixture of 2 diastereoisomers). M⁺(ESI): 458.4. HPLC (Condition A): Rt: 4.1 min (HPLC purity: 91.8%).

Step b) Formation of (2R)-N,2-dihydroxy-5-methyl-3-({(2R)-2-methyl-4-[4-(trifluoro methyl)-2-pyridinyl]piperazinyl}carbonyl)hexanamide To a solution of (5S)-2,2-dimethyl-5-[(1S)-3-methyl-1-({(2R)-2-methyl-4-[4-(trifluoro methyl)pyridin-2-yl]piper-azin-1-yl}carbonyl)butyl]-1,3-dioxolan-4-one (142 mg; 0.31 mmol; 1.0 eq.) in MeOH (5.0 mL) was added an aqueous solution of hydroxylamine (50%; 0.046 mL; 1.55 mmol; 5.0 eq.) and the resulting reaction mixture was stirred at RT for 4.5 h. Evaporation of the solvents gave an oil. This residue was taken up in MeOH/ACN (2 mL/1 mL) and purified by reverse-phase chromatography to give the title product (3) as a white powder (40 mg; 29.8%) as a single diastereoisomer. M⁻(ESI): 431.0; M⁺(ESI): 433.6. HPLC (condition C): Rt: 10.8 min (HPLC purity: 98.7%).

Example 4

(2S,3S)-N,2-dihydroxy-5-methyl-3-{[(2R)-2-methyl-4-(2-pyridinyl)piperazinyl]carbonyl}hexanamide (4)

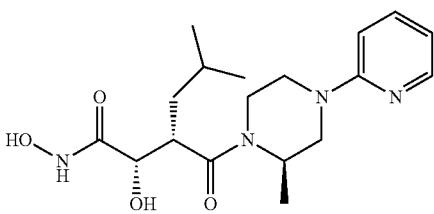

(4)

Step a) Formation of (5S)-2,2-dimethyl-5-((1S)-3-methyl-1-{[(2R)-2-methyl-4-(2-pyridinyl)piperazinyl]carbonyl}butyl)-1,3-dioxolan-4-one

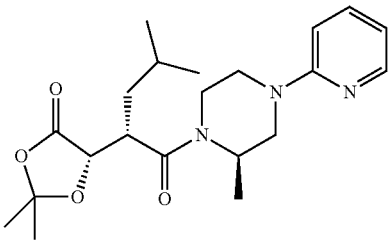

To a cold (0° C.) solution of (2R)-2-[(4S)-2,2-dimethyl-5-oxo-1,3-dioxolan-4-yl]-4-methylpentanoic acid (prepared according to WO 94/0244 or similarly to Seebach et al., 1990, Org. Syntheses, Coll. Vol. III, p 153-159; 7; 755.0 mg; 3.28 mmol; 1.0 eq.) and DIEA (1.18 mL; 6.89 mmol; 2.1 eq.) in DMF (4 mL) was added HATU (1.37 g; 3.61 mmol; 1.1 eq.) and the resulting reaction mixture was stirred for 2 min at 0° C. (3R)-3-methyl-1-pyridin-2-ylpiperazine (Intermediate 3, 639.3 mg; 3.61 mmol; 1.1 eq.) was then added and the resulting reaction mixture was stirred for 14 h at RT. Water was added and the mixture was extracted with Et₂O (3×). The combined organic layers were washed with an aqueous saturated solution of NaCl, dried over MgSO₄, filtered and evaporated to give an oil. This residue was purified by chromatography (gradient from 33% EtOAc in c-hex up to 50% EtOAc in c-hex in about 30 min) to give the title product as a white solid (625 mg, 49%) as a mixture of 2 diastereoisomers (HPLC (Condition D): Rt major: 13.7 min; Rt minor: 13.8 min.; major/minor: 55/45). M⁺(ESI): 390.3. HPLC (Condition A), Rt: 2.3 min (HPLC purity: 97.4%).

Step b) Formation of (2S,3S)-N,2-dihydroxy-5-methyl-3-{[(2R)-2-methyl-4-(2-pyridinyl)piperazinyl]carbonyl}hexanamide To a solution of (5S)-2,2-dimethyl-5-((1R)-3-methyl-1-{[(2R)-2-methyl-4-(2-pyridinyl)piperazinyl]carbonyl}butyl)-1,3-dioxolan-4-one (517 mg; 1.33 mmol; 1.0 eq) in iPrOH (2.0 mL) was added an aqueous solution of hydroxylamine (391.5 µl; 6.64 mmol; 5.0 eq.) and the resulting reaction mixture was stirred at RT for 40 min. HPLC analyses showed the presence of 2 diastereoisomers (75/25). This reaction mixture was dissolved in water (6 mL) and directly purified by reverse-phase chromatography (major diastereoisomer as the first eluted peak, gradient starting from 100% H$_2$O up to 75% H$_2$O in ACN in 5 min, then isocratic 75% H$_2$O in ACN for 25 min; flow: 50 mL/min) to give the title product (4) as a white powder (230 mg; 47%). $^1$H NMR (CD$_3$OD, 300 MHz) δ 8.10 (m, 1H), 7.58 (m, 1H), 6.84 (m, 1H), 6.69 (m, 1H), 4.84-4.70 (m, 1H), 4.60 (m, 1H), 4.48 (m, 0.4H), 4.19 (m, 1H), 4.13-3.98 (m, 2H), 3.71-3.55 (m, 0.6H), 3.30-3.07 (m, 2H), 3.05-2.82 (m, 1H), 1.94-1.76 (m, 1H), 1.55-1.38 (m, 3H), 1.35 (d, 1.3H, J=6.7 Hz), 1.23 (d, 1.7H, J=6.7 Hz), 0.93 (m, 6H). M$^+$(ESI): 365.2, M$^-$(ESI): 363.2. HPLC (Condition B), Rt: 2.4 min (HPLC purity: 97.6%).

Example 5

(2S,3S)-N,2-dihydroxy-5-methyl-3-{[(2S)-2-methyl-4-pyridin-2-yl piperazin-1-yl]carbonyl}hexanamide (5)

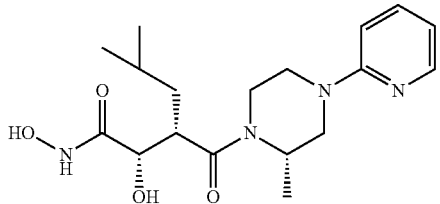

Step a) Formation of (5S)-2,2-dimethyl-5-((1S)-3-methyl-1-{[(2S)-2-methyl-4-pyridin-2-ylpiperazin-1-yl]carbonyl}butyl)-1,3-dioxolan-4-one

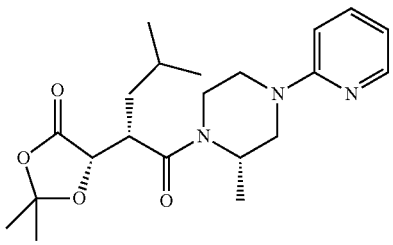

To a solution of a 55/45 diastereoisomeric mixture of pentafluorophenyl (2S)-2-[(4S)-2,2-dimethyl-5-oxo-1,3-dioxolan-4-yl]-4-methylpentanoate and pentafluorophenyl (2R)-2-[(4S)-2,2-dimethyl-5-oxo-1,3-dioxolan-4-yl]-4-methylpentanoate (Intermediate 1, 198 mg; 0.50 mmol; 1.0 eq.) in DMF (4 mL) was added (3S)-3-methyl-1-pyridin-2-ylpiperazine (Intermediate 4, 88.6 mg; 0.50 mmol; 1.0 eq.) and the resulting reaction mixture was stirred 48 h at RT. Water was added and the mixture was extracted with Et$_2$O. The combined organic layers were washed with brine, dried over MgSO$_4$, filtered and evaporated to give an oil. Purification by chromatography (SiO$_2$, gradient from 10% EtOAc in c-hex up to 40% EtOAc in c-hex in 15 min) gave the title compound as a colorless oil (43 mg; 22%) (mixture of 2 diastereoisomers). M$^+$(ESI): 390.3.

Step b) Formation of (2R,3S)-N,2-dihydroxy-5-methyl-3-{[(2S)-2-methyl-4-pyridin-2-ylpiperazin-1-yl]carbonyl}hexanamide The title product (5) was prepared following the procedure of Example 1 (step b) but starting from (5S)-2,2-dimethyl-5-((1S)-3-methyl-1-{[(2S)-2-methyl-4-pyridin-2-yl piperazin-1-yl]carbonyl}butyl)-1,3-dioxolan-4-one (as a mixture of 2 diastereoisomers) (28 mg, 71%). M$^-$(ESI): 363.2; M$^+$(ESI): 365.2. HPLC: Rt: 1.4 min (HPLC purity: 100%).

Example 6

(2S,3S)-6-(4-ethoxyphenyl)-N,2-dihydroxy-3-{[(2R)-2-methyl-4-pyridin-2-ylpiperazin-1-yl]-carbonyl}hexanamide (6)

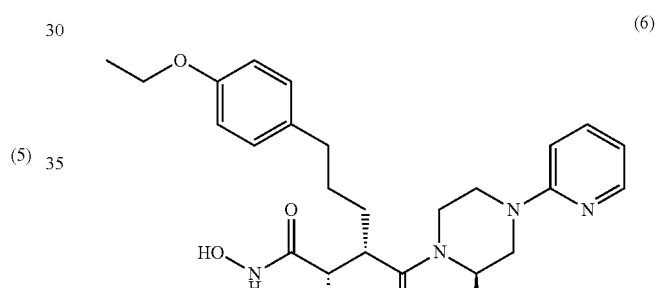

Step a) Formation of (5S)-5-((1S)-4-(4-ethoxyphenyl)-1-{[(2R)-2-methyl-4-(2-pyridinyl)piperazinyl]carbonyl}butyl)-2,2-dimethyl-1,3-dioxolan-4-one

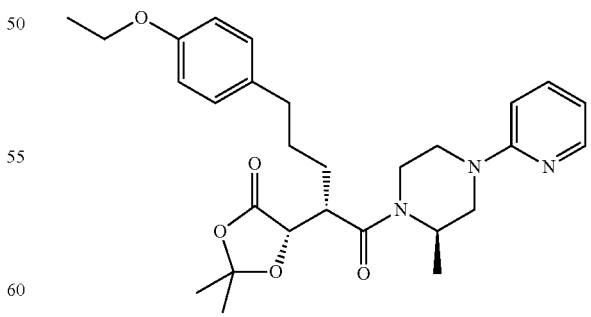

The title product was prepared following the procedure of Example 4 (step a) but starting from (3R)-3-methyl-1-pyridin-2-ylpiperazine (Intermediate 3) and (2R)-2-[(4S)-2,2-dimethyl-5-oxo-1,3-dioxolan-4-yl]-5-(4-ethoxyphenyl)pentanoic acid (Intermediate 2). Purification by chromatography (SiO₂, gradient from 33% EtOAc in c-hex up to 50% EtOAc in c-hex in about 30 min) gave the title compound as an orange solid (190 mg; 52%, as a mixture of 2 diastereoisomers). M⁺(ESI): 496.5. HPLC (Condition A): Rt: 3.2 min (HPLC purity: 982%).

Step b) Formation of (2S,3S)-6-(4-ethoxyphenyl)-N, 2-dihydroxy-3-{[(2R)-2-methyl-4-(2-pyridinyl)piperazinyl]carbonyl}hexanamide The title product (6) was prepared following the procedure of Example 1 (step b) but starting from (5S)-5-((1R)-4-(4-ethoxyphenyl)-1-{[(2R)-2-methyl-4-(2-pyridinyl)piperazinyl]carbonyl}butyl)-2,2-dimethyl-1,3-dioxolan-4-one (185 mg; 0.37 mmol; 1.0 eq.). Purification by reverse-phase chromatography (gradient from 10/90 0.1% TFA in ACN/0.1% TFA in H₂O up to 40/60 0.1% TFA in ACN/0.1% TFA in H₂O in 20 min) gave the title compound as a white powder (160 mg; 91% as a mixture of 2 diastereoisomers, 56/44). M⁻(ESI): 469.2; M⁺(ESI): 471.3. HPLC (condition A): Rt: 2.2 min (HPLC purity: 100%). HPLC (Condition C): Rt: major diast. 10.4 min; minor diast. 10.7 min major/minor: 56/44.

Example 7

(2S,3S)-6-(4-ethoxyphenyl)-N,2-dihydroxy-3-{[(2S)-2-methyl-4-(2-pyridinyl)piperazinyl]carbonyl}hexanamide (7)

The title product was prepared following the procedure of example 4 (step a) but starting from (3S)-3-methyl-1-pyridin-2-ylpiperazine (Intermediate 4) and (2R)-2-[(4S)-2,2-dimethyl-5-oxo-1,3-dioxolan-4-yl]-5-(4-ethoxyphenyl)pentanoic acid (Intermediate 2, 168 mg; 0.5 mmol; 1.0 eq.). Purification by chromatography (SiO₂, gradient from 40% EtOAc in c-hex up to 60% EtOAc in c-hex in about 30 min) gave the title compound (126 mg; 51%, as a mixture of 2 diastereoisomers).

Step b) Formation of (2S,3R)-6-(4-ethoxyphenyl)-N, 2-dihydroxy-3-{[(2S)-2-methyl-4-(2-pyridinyl)piperazinyl]carbonyl}hexanamide The title product (7) was prepared following the procedure of Example 1 (step b) but starting from (5S)-5-((1R)-4-(4-ethoxyphenyl)-1-{[(2S)-2-methyl-4-(2-pyridinyl)piperazinyl]carbonyl}butyl)-2,2-dimethyl-1,3-dioxolan-4-one (110 mg; 0.22 mmol; 1.0 eq.) giving after purification (reverse-phase chromatography) a white solid (51 mg; 49% as a mixture of 2 diastereoisomers). M⁻(ESI): 469.3; M⁺(ESI): 471.4. HPLC (Condition A): Rt: 2.2 min (HPLC purity: 99.2%).

Example 8

(2S,3S)-6-(4-ethoxyphenyl)-N,2-dihydroxy-3-{[(2R)-2-methyl-4-pyrimidin-2-ylpiperazin-1-yl]carbonyl}hexanamide (8)

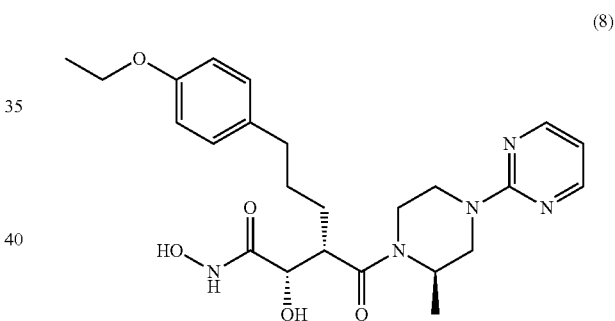

Step a) Formation of (5S)-5-((1S)-4-(4-ethoxyphenyl)-1-{[(2R)-2-methyl-4-(2-pyrimidinyl)piperazinyl]carbonyl}butyl)-2,2-dimethyl-1,3-dioxolan-4-one

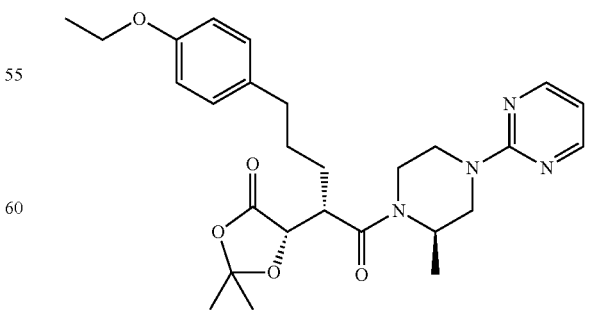

The title product was prepared following the procedure of Example 4 (step a) but starting from (2R)-2-[(4S)-2,2-dim-

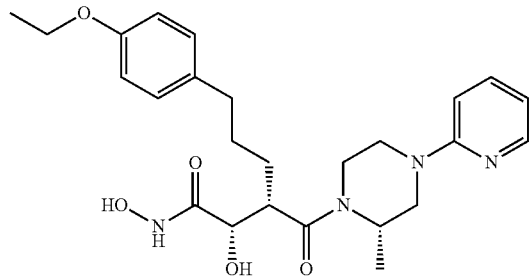

Step a) Formation of (5S)-5-((1S)-4-(4-ethoxyphenyl)-1-{[(2S)-2-methyl-4-(2-pyridinyl)piperazinyl]carbonyl}butyl)-2,2-dimethyl-1,3-dioxolan-4-one

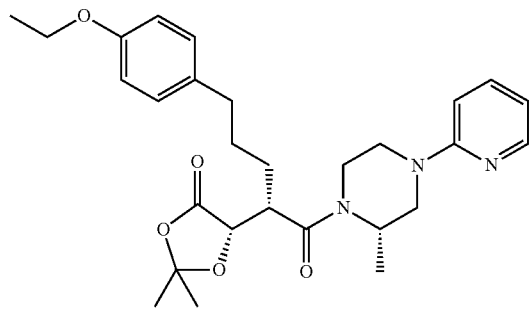

ethyl-5-oxo-1,3-dioxolan-4-yl]-5-(4-ethoxyphenyl)pentanoic acid (Intermediate 2, 150 mg; 0.45 mmol; 1.0 eq.) and 2-[(3R)-3-methylpiperazin-1-yl]pyrimidine (Intermediate 7, 87 mg; 0.49 mmol; 1.1 eq.) giving after purification by chromatography (SiO$_2$, gradient from 33% EtOAc in c-hex up to 50% EtOAc in c-hex in about 30 min) the title compound as a white foam (110 mg; 45% as a mixture of 2 diastereoisomers). M$^+$(ESI): 497.4. HPLC (Condition A): Rt: 4.0 min (HPLC purity: 98.5%).

Step b) Formation of (2S)-6-(4-ethoxyphenyl)-N,2-dihydroxy-3-{[(2R)-2-methyl-4-(2-pyrimidinyl)piperazinyl]carbonyl}hexanamide The title product (8) was prepared following the procedure of Example 1 (step b) but starting from (5S)-5-((1R)-4-(4-ethoxyphenyl)-1-{[(2R)-2-methyl-4-(2-pyrimidinyl) piperazinyl]carbonyl}butyl)-2,2-dimethyl-1,3-dioxolan-4-one (109 mg; 0.22 mmol; 1.0 eq.). Purification by reverse-phase chromatography (gradient from 20/80 0.1% TFA in ACN/0.1% TFA in H$_2$O up to 45/55 0.1% TFA in ACN/0.1% TFA in H$_2$O in 20 min) gave the title compound as a white powder (54 mg; 42% as a mixture of 2 diastereoisomers, 68/32). M$^-$(ESI): 470.2; M$^+$(ESI): 472.2. HPLC (Condition C): Rt: major diast. 9.8 min; minor diast. 10.1 min major/minor:68/32. HPLC (Condition A): Rt: 2.6 min (HPLC purity: 100%).

Example 9

(2S,3S)-6-(4-ethoxyphenyl)-3-{[(2R)-4-(2-fluorophenyl)-2-methylpiperazin-1-yl]carbonyl}-N,2-dihydroxyhexanamide (9)

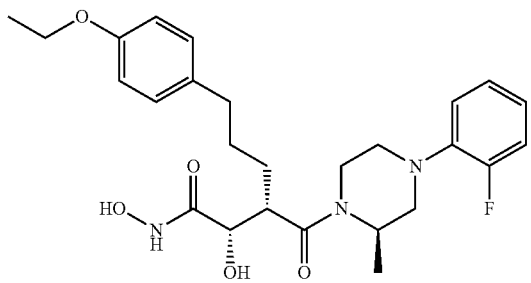

Step a) Formation of (5S)-5-((1S)-4-(4-ethoxyphenyl)-1-{[(2R)-4-(2-fluorophenyl)-2-methyl piperazinyl]carbonyl}butyl)-2,2-dimethyl-1,3-dioxolan-4-one

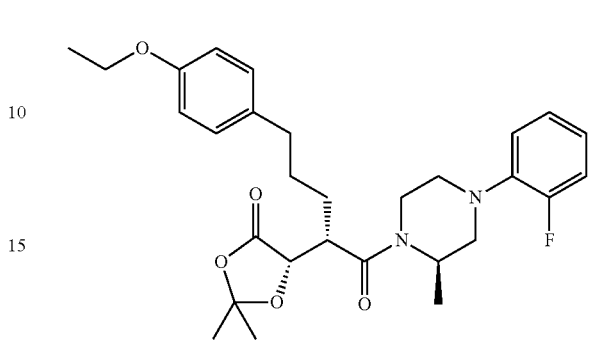

The title product was prepared following the procedure of Example 4 (step a) but starting from (2R)-2-[(4S)-2,2-dimethyl-5-oxo-1,3-dioxolan-4-yl]-5-(4-ethoxyphenyl)pentanoic acid (Intermediate 2, 150 mg; 0.45 mmol; 1.0 eq.) and (3R)-1-(2-fluorophenyl)-3-methyl piperazine (Intermediate 5, 95 mg; 0.49 mmol; 1.1 eq.) gave after purification by chromatography (SiO$_2$, gradient from 33% EtOAc in c-hex up to 50% EtOAc in c-hex in about 30 min) the title compound as a white foam (106 mg; 42% as a mixture of 2 diastereoisomers). M$^+$(ESI): 513.6. HPLC (Condition A): Rt: 5.0 min (HPLC purity: 99%).

Step b) Formation of (2S)-6-(4-ethoxyphenyl)-3-{[(2R)-4-(2-fluorophenyl)-2-methyl piperazinyl]carbonyl}-N,2-dihydroxyhexanamide The title product (9) was prepared following the procedure of Example 1 (step b) but starting from (5S)-5-((1R)-4-(4-ethoxyphenyl)-2-methyl piperazinyl]carbonyl}butyl)-2,2-dimethyl-1,3-dioxolan-4-one (112 mg; 0.22 mmol; 1.0 eq.). Purification by reverse phase chromatography (gradient from 40/60 0.1% TFA in ACN/0.1% TFA in H$_2$O up to 65/35 0.1% TFA in ACN/0.1% TFA in H$_2$O in 20 min) gave the title product as a white powder (82 mg; 76% as a mixture of 2 diastereoisomers, 67/33). M$^-$(ESI): 486.1; M$^+$(ESI): 488.1. HPLC (Condition C): Rt: major diast. 12.3 min; minor diast. 12.6 min major/minor:67/33.

Example 10

(2S,3S)-N,2-dihydroxy-5-methyl-3-{[(2R)-2-methyl-4-pyrimidin-2-yl piperazin-1-yl]carbonyl}hexanamide (10)

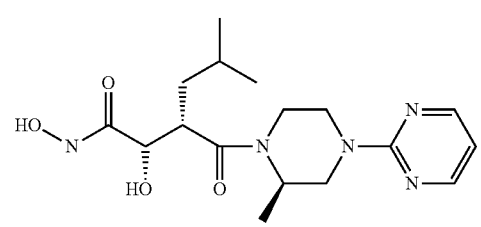

The title product was prepared following the procedure of Example 4 (step a and b) but starting from 2-[(3R)-3-methylpiperazin-1-yl]pyrimidine (Intermediate 7). Purification by reverse-phase chromatography gave the title product as a white powder. M⁻(ESI): 364.2; M⁺(ESI): 366.0. HPLC (Condition A): Rt: 2.0 min (HPLC purity: 99.4%).

Example 11

(2S,3S)-N,2-dihydroxy-5-methyl-3-{[(2S)-2-methyl-4-(4-methylpyridin-2-yl)piperazin-1-yl]carbonyl}hexanamide (11)

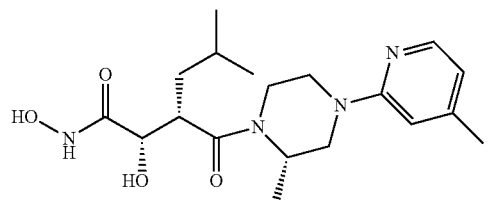

(11)

The title product was prepared following the procedure of Example 4 (step a and b) but starting from (3S)-3-methyl-1-(4-methylpyridin-2-yl)piperazine. Purification by reverse-phase chromatography gave the title product as a white powder. M⁻(ESI): 377.2; M⁺(ESI): 379.2. HPLC (Condition A): Rt: 2.2 min (HPLC purity: 84.4%).

Example 12

(2S,3S)-3-{[(2R)-4-(2-fluoro-5-methoxyphenyl)-2-methylpiperazin-1-yl]carbonyl}-N,2-dihydroxy-5-methylhexanamide (12)

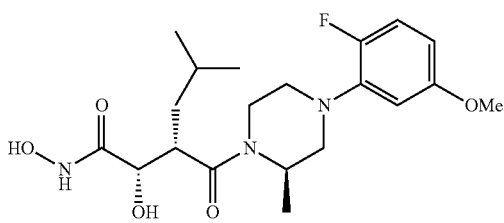

(12)

The title product was prepared following the procedure of Example 4 (step a and b) but starting from (3R)-1-(2-fluoro-5-methoxyphenyl)-3-methylpiperazine. Purification by reverse-phase chromatography gave the title product as a white powder. M⁻(ESI): 410.2; M⁺(ESI): 412.3. HPLC (Condition A): Rt: 3.1 min (HPLC purity: 68.2%).

Example 13

(2S,3S)-3-{[(2R)-4-(2-fluorophenyl)-2-methylpiperazin-1-yl]carbonyl}-N,2-dihydroxy-5-methylhexanamide (13)

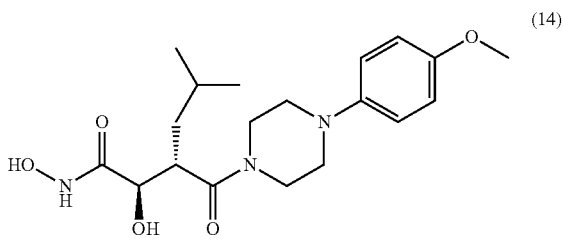

(13)

The title product was prepared following the procedure of Example 4 (step a and b) but starting from (3R)-1-(2-fluorophenyl)-3-methyl piperazine (Intermediate 5). Purification by reverse-phase chromatography gave the title product as a white powder. M⁻(ESI): 380.1; M⁺(ESI): 381.9. HPLC (Condition A): Rt: 3.1 min (HPLC purity: 100%).

Example 14

(2R,3S)-N,2-dihydroxy-3-{[4-(4-methoxyphenyl)piperazin-1-yl]carbonyl}-5-methylhexanamide (14)

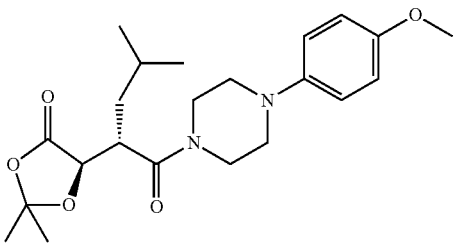

(14)

Step a) Formation of (5R)-5-((1S)-1-{[4-(4-methoxyphenyl)piperazin-1-yl]carbonyl}-3-methylbutyl)-2,2-dimethyl-1,3-dioxolan-4-one To a cold solution (0° C.) of (2S)-2-[(4R)-2,2-dimethyl-5-oxo-1,3-dioxolan-4-yl]-4-methylpentanoic acid (prepared according to WO 94/02447 or similarly to Seebach et al., 1990, *Org. Syntheses, Coll. Vol. III*, p 153-159 but starting from diisopropyl (R)-(+)-malate, 150 mg, 0.65 mmol) in anhydrous DCM (3 mL) were added DIEA (115 μL, 0.69 mmol) and fluoro-N,N,N',N'-tetramethylformamidinium hexafluorophosphate (190 mg, 0.72 mmol, Aldrich). The reaction mixture was stirred at 0° C. for 40 min. Then a solution of 1-(4-methoxyphenyl)-piperazine (138 mg, 0.72 mmol, Chess) and DIEA (115 μL, 0.69 mmol) in anhydrous DCM (1 mL) was added. The reaction mixture was stirred for 1 hour is at RT and then poured on a silica column (30 g, wet with c-Hex/EtOAc 4:1). Purification was performed with a gradient cHex/EtOAc 4:1 to c-Hex/EtOAc 1:1 in 30 min to give 158 mg of a white powder. Recrystallization from iPrOH gave 112 mg (43%) of the title compound as a white powder. HPLC, Rt: 3.02 min (purity: 99.0%). LC/MS, M+(ESI): 405.3. $^1$H NMR (CD$_3$OD, 300 MHz) δ 7.00 (d, J=9.2 Hz, 2H), 6.89 (d, J=9.2 Hz, 2H), 4.56 (d, J=8.7 Hz, 1H), 3.87 (m, 3H), 3.78 (s, 3H), 3.73 (m, 1H), 3.50 (m, 1H), 3.15-3.00 (m, 4H), 1.93-1.72 (m, 2H), 1.66 (s, 3H), 1.58 (m, 1H), 1.56 (s, 3H), 0.98 (d, J=6.4 Hz, 6H).

Step b) Formation of (2R,3S)-N,2-dihydroxy-3-{[4-(4-methoxyphenyl)piperazin-1-yl]carbonyl}-5-methylhexanamide (14)

To a suspension of (5R)-5-((1S)-1-{[4-(4-methoxyphenyl) piperazin-1-yl]carbonyl}-3-methylbutyl)-2,2-dimethyl-1,3-dioxolan-4-one (108 mg, 0.27 mmol) in iPrOH (4 mL) was added a 50% aqueous solution of hydroxylamine (80 μL) and the resulting mixture was stirred at RT for 2 hours. Then the white solid was filtered off, washed with water and dried under reduced pressure to give 56 mg (55%) of the title compound as a white powder. HPLC, Rt: 1.57 min (purity: 99.1%). LC/MS, M+(ESI): 380.2, M−(ESI): 378.2. $^1$H NMR (CD$_3$OD, 300 MHz) δ 7.01 (d, J=9.1 Hz, 2H), 6.89 (d, J=9.1 Hz, 2H), 4.05 (d, J=6.8 Hz, 1H), 3.96 (m, 2H), 3.80 (m, 1H), 3.78 (s, 3H), 3.68 (m, 1H), 3.49 (m, 1H), 3.15-2.99 (m, 4H), 1.72 (m, 1H), 1.54 (m, 1H), 1.29 (m, 1H), 0.96 (d, J=6.5 Hz, 3H), 0.95 (d, J=6.4 Hz, 3H).

Example 15

(2S,3S)-3-{[(2R)-4-(4-chloro-2-fluorophenyl)-2-methylpiperazin-1-yl]carbonyl}-N,2-dihydroxy-5-methylhexanamide (15)

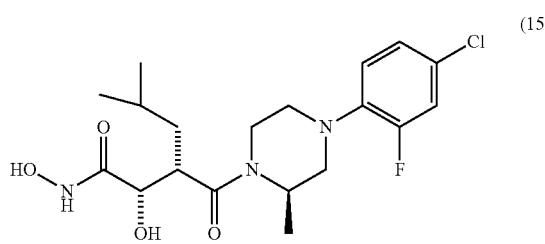

The title product was prepared following the procedure of Example 4 (step a and b) but starting from (3R)-1-(4-chloro-2-fluorophenyl)-3-methylpiperazine. Purification by reverse-phase chromatography gave the title product as a white powder. M−(ESI): 414.2; M+(ESI): 416.2. HPLC (Condition A): Rt: 3.4 min (HPLC purity: 99.0%).

Example 16

(2S,3S)-3-{[(2R)-4-(5-chloropyridin-2-yl)-2-methylpiperazin-1-yl]carbonyl}-N,2-dihydroxy-5-methylhexanamide (16)

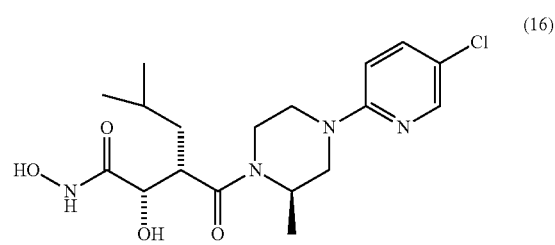

The title product was prepared following the procedure of Example 4 (step a and b) but starting from (3R)-1-(5-chloropyridin-2-yl)-3-methylpiperazine. Purification by reverse-phase chromatography gave the title product as a white powder. M−(ESI): 397.2; M+(ESI): 399.2. HPLC (Condition A): Rt: 1.4 min (HPLC purity: 97.7%).

Example 17

(2R,3S)-3-{[4(4-fluorophenyl)piperazin-1-yl]carbonyl}-N,2-dihydroxy-5-methylhexanamide (17)

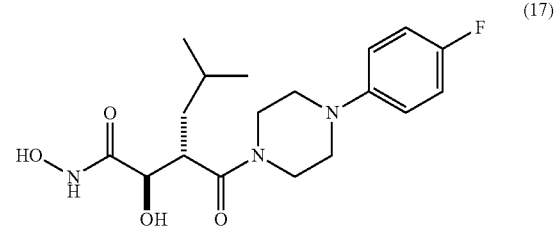

The title product was prepared following the procedure of Example 14 (step a and b) but starting from 1-(4-fluorophenyl)-piperazine di-hydrochloride and DIEA. Purification by reverse-phase chromatography gave the title product as a white powder. M−(ESI): 366.2; M+(ESI): 368.2. HPLC (Condition A): Rt: 2.1 min (HPLC purity: 100%).

Example 18

(2R,3S)-3-{[(1S,4S)-5-(4-fluorophenyl)-2,5-diazabicyclo[2.2.1]hept-2-yl]carbonyl}-N,2-dihydroxy-5-methylhexanamide (18)

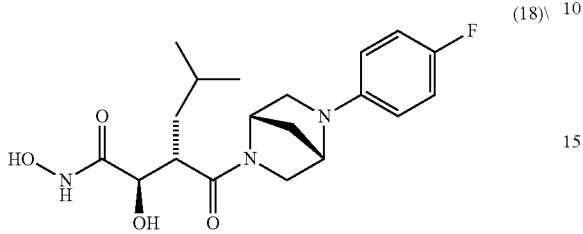

(18)

The title product was prepared following the procedure of Example 4 (step a and b) but starting from (1S,4S)-5-(4-fluorophenyl)-5-aza-2-azoniabicyclo[2.2.1]heptane chloride and DIEA. Purification by reverse-phase chromatography gave the title product as a white powder. M⁻(ESI): 378.2; M⁺(ESI): 380.0. HPLC (Condition A): Rt: 2.8 min (HPLC purity: 98.0%).

The novel derivatives according to Formula (VI) can be prepared from readily available starting materials by several synthetic approaches, using both solution-phase and solid-phase chemistry protocols. Examples of synthetic pathways for the will be described.

A preferred process for preparing a compound of Formula (VI) consists in coupling a dioxolane-protected di-carboxylic acid of formula (VII) with the appropriate amine (VIII) to form the intermediate (IX) wherein E, $R^1$ and $R^{15}$ and n are defined as above (Scheme 4 below). General protocols for such coupling are given below in the Examples, using conditions and methods well known to those skilled in the art to prepare an amide bond from an amine and a carboxylic acid or carboxylic acid derivative (e.g. acid chloride), with or without standard coupling agents, such as e.g. DIC, EDC, TBTU, DCC, HATU, PyBOP®, Isobutyl chloroformate, 1-methyl-2-chloropyridinium iodide (Mukaiyama's reagent) or others in the presence or not of bases such as TEA, DIEA, NMM in a suitable solvent such as DCM, THF or DMF.

Scheme 4

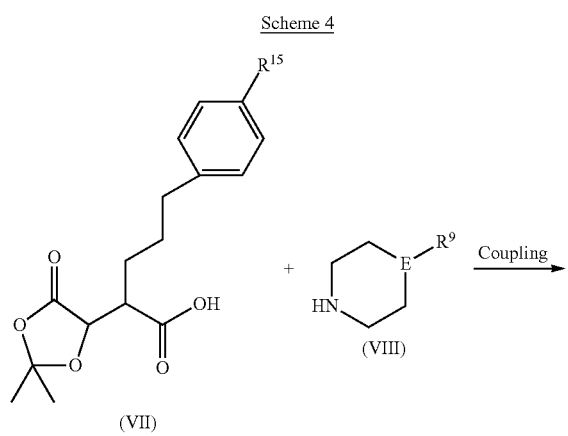

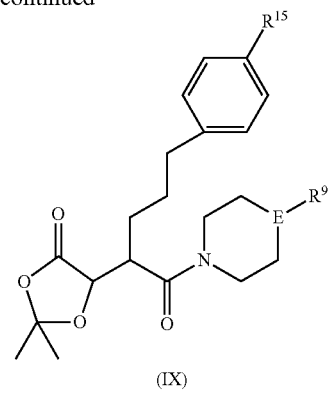

(IX)

Compounds of formula (VIII) are commercially available or can be obtained from protocols herein described.

Intermediate of formula (IX) can be reacted with hydroxylamine or can be reacted with a protected hydroxylamine $H_2NO—R^8$ where $R^8$ is a protecting group such as t-butyl, benzyl, trialkylsilyl, tetrahydropyranyl (THP) or a any suitable protecting group, followed by a known deprotection step to form compound of Formula (VI) (Scheme 5 below).

Scheme 5

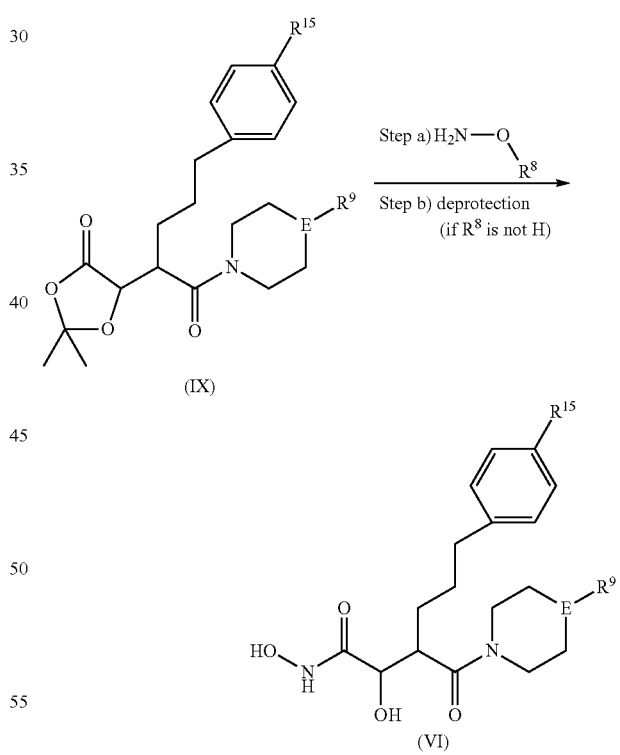

The HPLC data provided in the examples described below were obtained as followed. HPLC: Waters Xterra® $C_8$ 3.5 μm column 50 mm×4.6 mm; UV detection (maxplot); flow: 2 mL/min;

Conditions: 8 min gradient from 0.1% TFA in $H_2O$ to 0.07% TFA in $CH_3CN$. The preparative HPLC were obtained with a Waters Xterra® Prep MS $C_8$ 10 μm column 300 mm×30 mm; UV detection (254 nM and 220 nM); flow: 30 mL/min. The MS data provided in the examples described below were obtained as followed: Mass spectrum: LC/MS Waters ZMD (ESI). The NMR data provided in the examples described below were obtained as followed: $^1$H-NMR: Bruker DPX-300 MHz.

The following reagents commercially available were used:

Diisopropyl (S)-(−)-malate (from Avocado), 2,3,4,5,6-pentafluorophenol (from Fluka), 3-bromo-2-methylpropene (from Aldrich), allyl bromide (from Fluka), HATU (from Aldrich), 2,2-dimethoxypropane (from Fluka), lithium bis(trimethylsilyl)amide (from Aldrich), 4-bromophenetole (from Aldrich), 1-bromo-4-(trifluoromethoxy)benzene (from Aldrich), tri-o-tolylphosphine (from Aldrich), palladium(11) acetate (from Acros), copper (II) chloride (from Aldrich), 1-(2-pyridyl)piperazine (from Aldrich), 1-(4-fluoro phenyl)-piperazine dihydrochloride (from Aldrich), 1-[5-(trifluoromethyl)pyridin-2-yl]piperazine (from Maybridge), 2-(piperidinium-4-yloxy)pyridinium dichloride (from Array), 6-piperazin-1-ylnicotinonitrile (from Maybridge), 1-(6-methylpyridin-2-yl)piperazine (from EmkaChem), 1-(6-chloropyridin-2-yl)piperazine (from Bionet), 1-(5-chloropyridin-2-yl) piperazine (from JW-Pharmlab), 1-(4-chloro-2-fluorophenyl)piperazine (from ABCR), 4-(2-chlorophenoxy) piperidinium chloride (from Array), 1-(2-chlorophenyl) piperazine (from EmkaChem), 6-methyl-4-piperazin-1-yl-2-(trifluoromethyl)quinoline (from Maybridge), 1-[3-(trifluoromethyl)pyridin-2-yl]piperazine (from Maybridge), 1-(3,5-dichloropyridin-4-yl)piperazine (from Maybridge), 1-(2-methoxyphenyl)piperazine (from Fluka), 1-(4-chloro phenyl)piperazine (from Acros), 2-piperazin-1-ylpyrazine (from EmkaChem), 4-(2-piperazin-1-ylethyl)morpholine (from EmkaChem), 2-piperazin-1-ylbenzonitrile (from EmkaChem), (1S,4S)-5-(4-fluorophenyl)-5-aza-2-azoniabicyclo[2.2.1]heptane (from Aldrich).

Intermediate 2: (2R)-2-[(4S)-2,2-dimethyl-5-oxo-1,3-dioxolan-4-yl]-5-(4-ethoxyphenyl)pentanoic acid

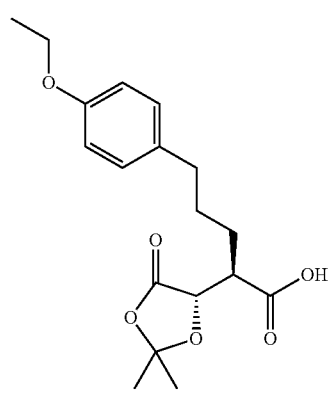

was synthesized as described above.

Intermediate 2a: diisopropyl (2R,3S)-2-allyl-3-hydroxybutanedioate

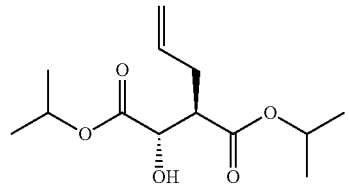

was synthesized as described above.

Intermediate 10: (2R)-2-[(4S)-2,2-dimethyl-5-oxo-1,3-dioxolan-4-yl]-5-[4-(trifluoromethoxy)phenyl]pentanoic acid

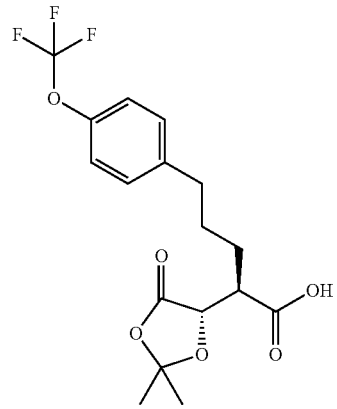

Step a) Formation of diisopropyl (2S,3R)-2-hydroxy-3-{(2E)-3-[4-(trifluoromethoxy)phenyl]-2-propenyl}butanedioate

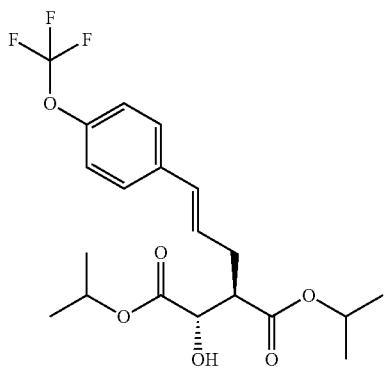

To a solution of diisopropyl (2R,3S)-2-allyl-3-hydroxybutanedioate (Intermediate 2a, 5.0 g; 19.4 mmol; 1.0 eq.), TEA (6.23 mL; 46.5 mmol; 2.4 eq.) in CH$_3$CN (50.0 mL) was added 1-bromo-4-(trifluoromethoxy)benzene (5.13 g; 21.3 mmol; 1.1 eq.). To this solution was added a sonicated mixture of tri-o-tolylphosphine (0.59 g; 1.94 mmol; 0.10 eq.) and palladium(II) acetate (43.46 mg; 0.19 mmol; 0.01 eq.) in CH₃CN (4 mL). The reaction was stirred at 80° C. for 14 h, cooled to RT and the solvents were evaporated (rotavap). The residue was taken up in EtOAc and washed with an aqueous saturated solution of NH₄Cl, an aqueous saturated solution of NaHCO₃ and then with an aqueous saturated solution of NaCl and dried over MgSO₄. Evaporation of the solvent gave an oil. Purification by chromatography (SiO₂, gradient from 10/90 EtOAc/c-hex to 100/0 EtOAc/c-hex in 30 min.) gave a colorless oil (6.98 g, 86.2%). M⁺(ESI): 419.2; M⁻(ESI): 417.0.

Step b) Formation of diisopropyl (2S,3R)-2-hydroxy-3-{3-[4-(trifluoromethoxy)phenyl]propyl}butanedioate

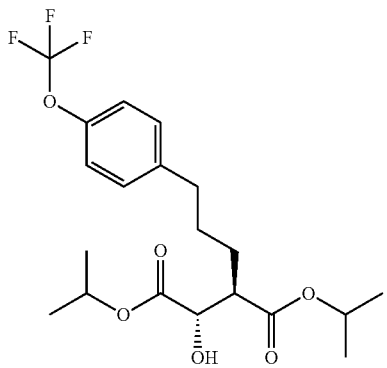

To a solution of diisopropyl (2S,3R)-2-hydroxy-3-{(2E)-3-[4-(trifluoromethoxy)phenyl]-2-propenyl}butanedioate (6.98 g; 16.68 mmol; 1.00 eq.) in methanol (105 mL) under N₂ atmosphere was added Pd—C (10%; 200 mg; 0.17 mmol; 0.01 eq.). The mixture was then hydrogenated under 2 bars of hydrogen for 14 h at RT. The reaction mixture was then filtered and evaporated to obtain the title compound (6.95 g; 99.1%).

Step c) Formation of (2S,3R)-2-hydroxy-3-{3-[4-(trifluoromethoxy)phenyl]propyl}butanedioic acid

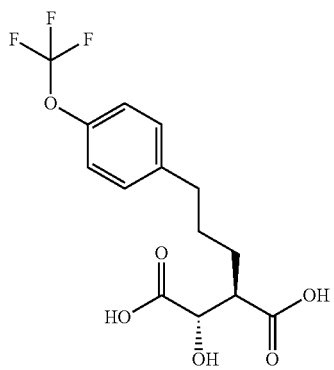

To a solution of diisopropyl (2S,3R)-2-hydroxy-3-{3-[4-(trifluoromethoxy)phenyl]propyl}butanedioate (6.98 g; 16.6 mmol; 1.0 eq.) in THF/water (3/1; 140 mL) was added potassium hydroxide (5.59 g; 99.6 mmol; 6.0 eq.). The reaction mixture was then stirred for 14 h at RT. The aq. layers were acidified with an aqueous solution of HCl to pH 2, extracted with EtOAc. The combined organic layers were then dried over MgSO₄ and evaporated to give the title compound as an oil (6.19 g), used in the next steps without further purification.

Step d) Formation of (2R)-2-[(4S)-2,2-dimethyl-5-oxo-1,3-dioxolan-4-yl]-5-[4-(trifluoro methoxy)phenyl]pentanoic acid To a solution of (2S,3R)-2-hydroxy-3-{3-[4-(trifluoromethoxy)phenyl]propyl}butanedioic acid (5.58 g; 16.6 mmol; 1.0 eq.) in acetone (61 mL) was added 2,2-dimethoxypropane (3.5 mL; 28.2 mmol; 1.70 eq.) and copper(II) chloride (220 mg; 1.66 mmol; 0.1 eq.). The resulting reaction mixture was stirred 14 h at RT. The reaction mixture was evaporated and the residue taken up in Et₂O and filtered on a pad of cellite. The liquids were evaporated again and the residue was treated with activated charcoal in Et₂O and filtered on a pad of cellite to give the title product as a greenish oil used in the next step without further purification. (5.85 g; 93.7%). M⁺(ESI): 377.0; M⁻(ESI): 375.1.

Example 19

(2S,3R)-6(4-ethoxyphenyl)-3-{[4-(4-fluorophenyl)piperazin-1-yl]carbonyl}-N,2-dihydroxyhexanamide (19)

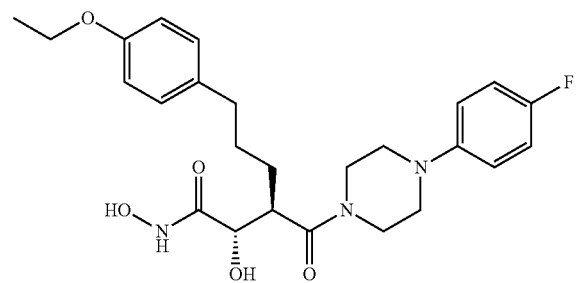

Step a) Formation of (5S)-5-((1R)-4-(4-ethoxyphenyl)-1-{[4-(4-fluorophenyl)piperazin-1-yl]carbonyl}butyl)-2,2-dimethyl-1,3-dioxolan-4-one

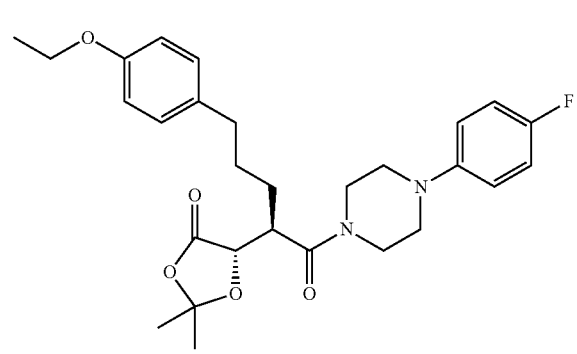

To a cold (0° C.) solution of (2R)-2-[(4S)-2,2-dimethyl-5-oxo-1,3-dioxolan-4-yl]-5-(4-ethoxyphenyl)pentanoic acid (Intermediate 2, 150 mg, 0.44 mmol, 1.0 eq) and DIEA (242 mg, 1.9 mmol, 4.1 eq) in anhydrous DMF (2 mL) was added dimethylamino-([1,2,3]triazolo[4,5-b]pyridin-3-yloxy)-methylene]-dimethyl-ammonium hexafluorophosphate (186 mg, 0.49 mmol, 1.1 eq). After 2 min of reaction, the 1-(4-fluoro-phenyl)-piperazine dihydrochloride was added and the reaction stirred overnight at room temperature. Water was then added and the aq. phase was extracted with Et$_2$O (3×). The combined organic phases were dried over MgSO$_4$, filtered and concentrated. The crude compound was purified on Silica gel (gradient from 33% EtOAc in c-hex to 50% in about 30 min) to obtain the title compound as a white solid (120 mg, 49%). M$^+$(ESI): 499.4; HPLC (Condition A), Rt: 4.53 min (HPLC purity: 98.7%).

Step b) (2S,3R)-6-(4-ethoxyphenyl)-3-{[4-(4-fluorophenyl)piperazin-1-yl]carbonyl}-N,2-dihydroxy-hexanamide To a solution of (5S)-5-((1R)-4-(4-ethoxyphenyl)-1-{[4-(4-fluorophenyl)-1-piperazinyl]carbonyl}butyl)-2,2-dimethyl-1,3-dioxolan-4-one (120 mg; 0.24 mmol; 1.0 eq.) in iPrOH (1 mL) was added an aq. solution of hydroxylamine (50%, 71 µl; 1.2 mmol; 5.0 eq.) and the reaction mixture was stirred for 45 min. CH$_3$CN (4 mL) was then added and the resulting mixture was purified by chromatography by reverse-phase preparative HPLC (gradient from 25% to 45% of CH$_3$CN containing 0.1% TFA, in water containing 0.1% TFA). The collected fractions were lyophilized to give the title compound (19) as a white solid (75 mg, 66%). $^1$H NMR (CDCl$_3$, 300 MHz) δ 7.1-6.99 (m, 6H), 6.80 (d, J=8.2 Hz, 2H), 4.26 (m, 1H), 4.06 (m, 1H), 3.96 (t, 2H, J=6.8 Hz), 3.80 (m, 1H), 3.63 (m, 2H), 3.40 (m, 1H), 3.23-3.00 (m, 4H), 2.58 (m, 2H), 1.85-1.52 (m, 4H), 1.38 (t, J=6.9 Hz, 3H). M$^-$(ESI): 472.1; M$^+$(ESI): 474.6. HPLC: Rt: 3.2 min (HPLC purity: 93.7%).

The compounds of Examples 20-49 were prepared by the procedure of Example 19 using the appropriate amine (in the presence of 1 eq. of DIEA when the amine used is a mono-hydrochloride salt, and in the presence of 2 eq. DIEA when the amine is a di-hydrochloride salt). The products were purified by preparative reverse-phase chromatography (HPLC).

Example 20

(2S,3R)-3-[(4-anilinopiperidin-1-yl)carbonyl]-6(4-ethoxyphenyl)-N,2-dihydroxyhexanamide (20)

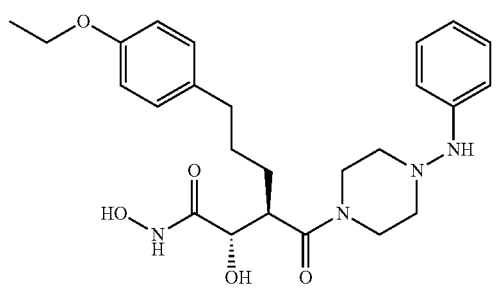

(20)

The title compound was prepared following the procedure of Example 19 using N-phenylpiperidin-4-amine. M$^-$(ESI): 468.0; M$^+$(ESI): 470.3. HPLC: Rt: 2.5 min (HPLC purity: 99.8%).

Example 21

(2S,3R)-6-(4-ethoxyphenyl)-N,2-dihydroxy-3-({4-[5-(trifluoromethyl)pyridin-2-yl]piperazin-1-yl}-carbonyl)hexanamide (21)

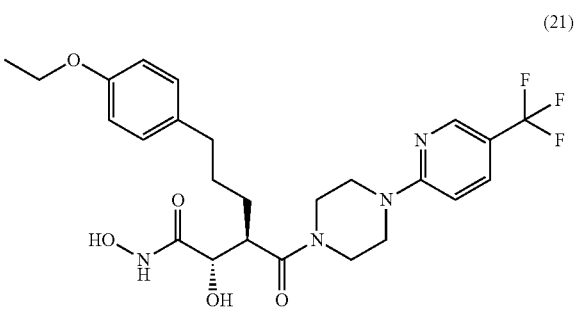

(21)

The title compound was prepared following the procedure of Example 19 using 1-[5-(trifluoromethyl)pyridin-2-yl]piperazine. M$^-$(ESI): 523; M$^+$(ESI): 525. HPLC: Rt: 3.4 min (HPLC purity: 96%).

Example 22

(2S,3R)-6-(4-ethoxyphenyl)-N,2-dihydroxy-3-{[4-pyridin-2-yloxy)piperidin-1-yl]carbonyl}hexanamide (22)

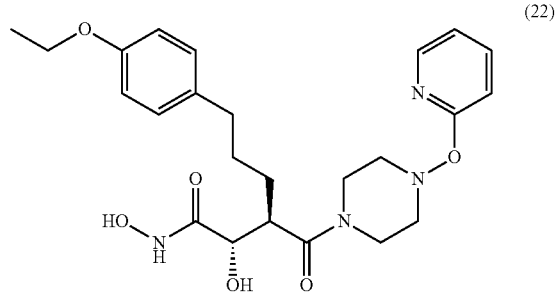

(22)

The title compound was prepared following the procedure of Example 19 using 2-(piperidinium-4-yloxy)pyridinium dichloride and DIEA. M⁻(EST): 470; M⁺(ESI): 472. HPLC: Rt: 2.8 min (HPLC purity: 98.3%).

Example 23

(2S,3R)-3-{[4-(5-cyanopyridin-2-yl)piperazin-1-yl]carbonyl}-6-(4-ethoxyphenyl)-N,2-dihydroxyhexanamide (23)

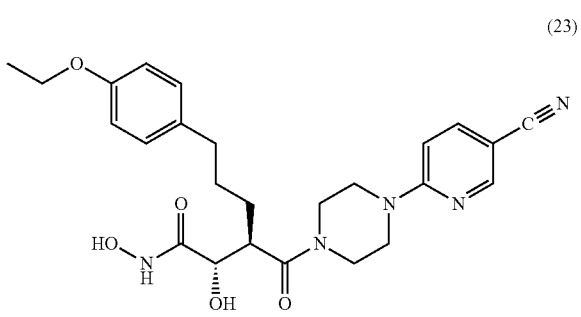

(23)

The title compound was prepared following the procedure of Example 19 using 6-piperazin-1-ylnicotinonitrile. M⁻(ESI): 480.6; M⁺(ESI): 482.8. HPLC: Rt: 3.2 min (HPLC purity: 962%).

Example 24

(2S,3R)-6-(4-ethoxyphenyl)-N,2-dihydroxy-3-{[4-(6-methylpyridin-2-yl)piperazin-1-yl]carbonyl}hexanamide (24)

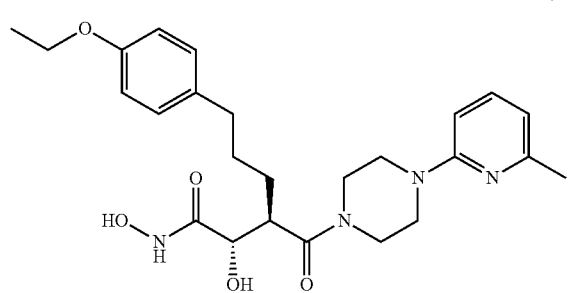

(24)

The title compound was prepared following the procedure of Example 19 using 1-(6-methylpyridin-2-yl)piperazine. M⁺(ESI): 471.3. HPLC: Rt: 2.3 min (HPLC purity: 80.2%).

Example 25

(2S,3R)-3-{[4-(6-chloropyridin-2-yl)piperazin-1-yl]carbonyl}-6-(4-ethoxyphenyl)-N,2-dihydroxyhexanamide (25)

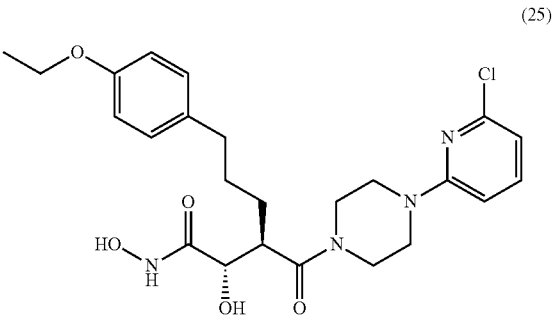

(25)

The title compound was prepared following the procedure of Example 19 using 1-(6-chloropyridin-2-yl)piperazine. M⁻(ESI): 489.3; M⁺(ESI): 491.7. HPLC: Rt: 3.8 min (HPLC purity: 98.1%).

Example 26

(2S,3R)-3-{[4(5-chloropyridin-2-yl)piperazin-1-yl]carbonyl}-6-(4-ethoxy phenyl)-N,2-dihydroxyhexanamide (26)

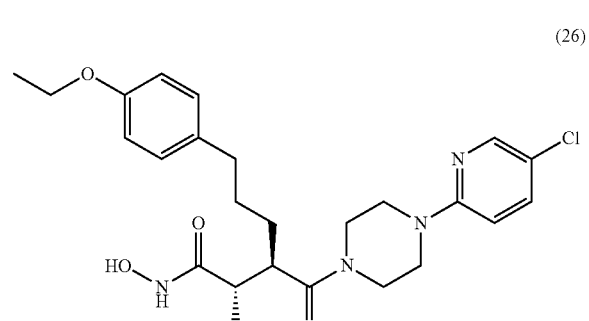

(26)

The title compound was prepared following the procedure of Example 19 using 1-(5-chloropyridin-2-yl)piperazine. M⁻(ESI): 489; M⁺(ESI): 491. HPLC: Rt: 2.9 min (HPLC purity: 97.9%).

Example 27

(2S,3R)-3-{[4-(4-chloro-2-fluorophenyl)piperazin-1-yl]carbonyl}-6-(4-ethoxyphenyl)-N,2-dihydroxyhexanamide (27)

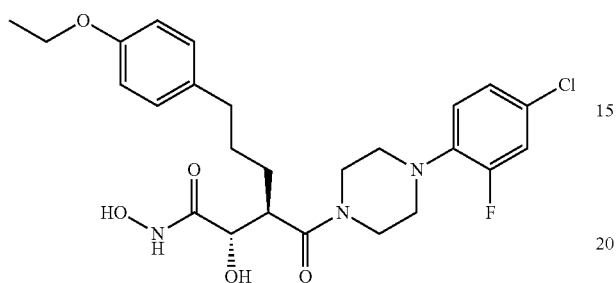

The title compound was prepared following the procedure of Example 19 using 1-(4-chloro-2-fluorophenyl)piperazine. M⁻(ESI): 506; M⁺(ESI): 508. HPLC: Rt: 4 min (HPLC purity: 95.6%).

Example 28

(2S,3R)-6-(4-ethoxyphenyl)-N,2-dihydroxy-3-({4-[4-(trifluoromethyl)phenoxy]piperidin-1-yl}carbonyl)hexanamide (28)

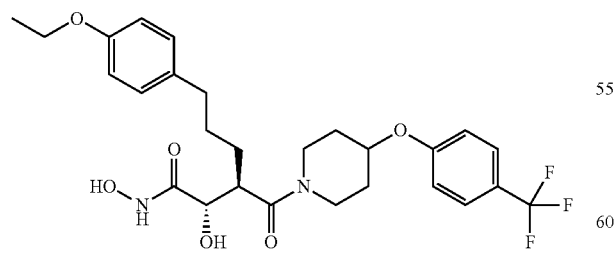

The title compound was prepared following the procedure of Example 19 using 4-[4-(trifluoromethyl)phenoxy]piperidinium chloride and DIEA. M⁻(ESI): 537.1; M⁺(ESI): 540.6. HPLC: Rt: 4.3 min (HPLC purity: 94.8%).

Example 29

(2S,3R)-3-{[4-(2-chlorophenoxy)piperidin-1-yl]carbonyl}-6-(4-ethoxyphenyl)-N,2-dihydroxyhexanamide (29)

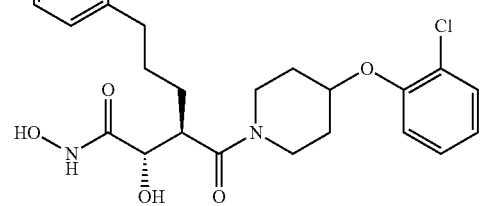

The title compound was prepared following the procedure of Example 19 using 4-(2-chlorophenoxy)piperidinium chloride and DIEA. M⁻(ESI): 503.8; M⁺(ESI): 505.0. HPLC: Rt: 4.1 min (HPLC purity: 90.7%).

Example 30

(2S,3R)-3-{[4-(2-chlorophenyl)piperazin-1-yl]carbonyl}-6-(4-ethoxyphenyl)-N,2-dihydroxyhexanamide (30)

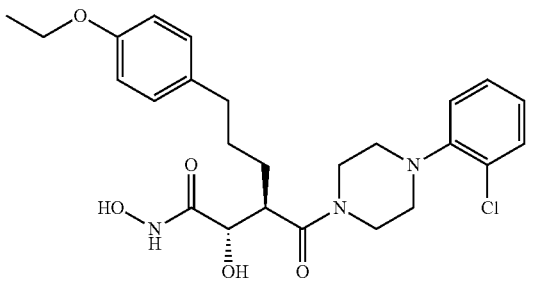

The title compound was prepared following the procedure of Example 19 using 1-(2-chlorophenyl)piperazine.

M⁻(ESI): 488.0; M⁺(ESI): 490.1. HPLC: Rt: 3.8 min (HPLC purity: 96%).

Example 31

(2S,3R)-6-(4-ethoxyphenyl)-N,2-dihydroxy-3-({4-[6-methyl-2-(trifluoromethyl)quinolin-4-yl]piperazin-1-yl}carbonyl)hexanamide (31)

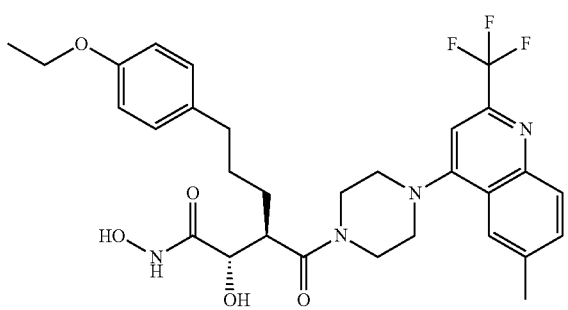

(31)

The title compound was prepared following the procedure of Example 19 using 6-methyl-4-piperazin-1-yl-2-(trifluoromethyl)quinoline. M⁻(ESI): 587.1; M⁺(ESI): 589.8. HPLC: Rt: 3.9 min (HPLC purity: 95.9%).

Example 32

(2S,3R)-6-(4-ethoxyphenyl)-N,2-dihydroxy-3-({4-[3-(trifluoromethyl)pyridin-2-yl]piperazin-1-yl}-carbonyl)hexanamide (32)

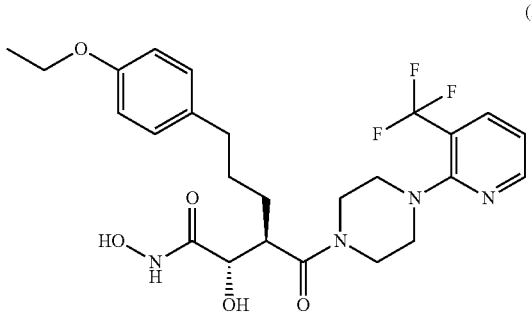

(32)

The title compound was prepared following the procedure of Example 19 using 1-[3-(trifluoromethyl)pyridin-2-yl]piperazine. M⁻(ESI): 523.2; M⁺(ESI): 525.1. HPLC: Rt: 3.7 min (HPLC purity: 93%).

Example 33

(2S,3R)-3-{[4-(3,5-dichloropyridin-4-yl)piperazin-1-yl]carbonyl}-6-(4-ethoxyphenyl)-N,2-dihydroxyhexanamide (33)

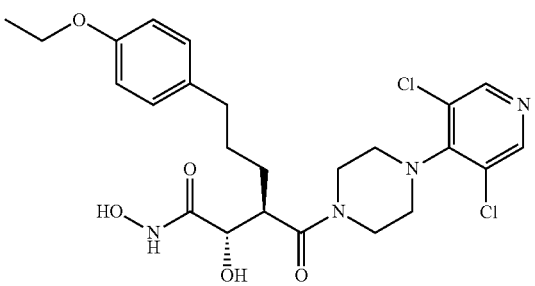

(33)

The title compound was prepared following the procedure of Example 19 using 1-(3,5-dichloropyridin-4-yl)piperazine. M⁻(ESI): 522.9; M⁺(ESI): 525.0. HPLC: Rt: 3.2 min (HPLC purity: 97.1%).

Example 34

(2S,3R)-6-(4-ethoxyphenyl)-N,2-dihydroxy-3-{[4-(2-methoxyphenyl)piperazin-1-yl]carbonyl}hexanamide (34)

(34)

The title compound was prepared following the procedure of Example 19 using 1-(2-methoxyphenyl)piperazine. M⁻(ESI): 484.0; M⁺(ESI): 486.1. HPLC: Rt: 2.7 min (HPLC purity: 94.7%).

Example 35

(2S,3R)-3-{[4-(4-chlorophenyl)piperazin-1-yl]-carbonyl}-6-(4-ethoxyphenyl)-N,2-dihydroxyhexanamide (35)

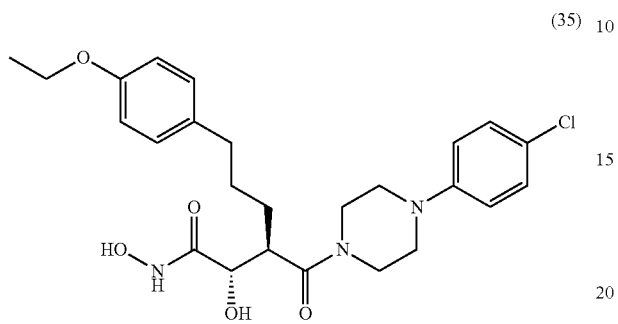

The title compound was prepared following the procedure of Example 19 using 1-(4-chlorophenyl)piperazine. M⁻(ESI): 488.1; M⁺(ESI): 490.0. HPLC: Rt: 3.8 min (HPLC purity: 91%).

Example 36

(2S,3R)-6-(4-ethoxyphenyl)-N,2-dihydroxy-3-[(4-pyrazin-2-ylpiperazin-1-yl)carbonyl]hexanamide (36)

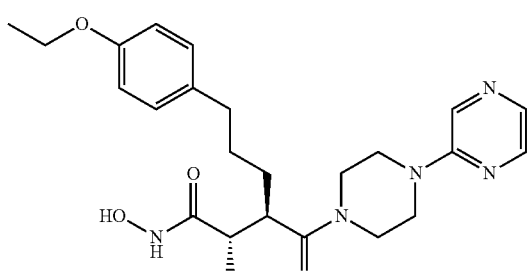

The title compound was prepared following the procedure of Example 19 using 2-piperazin-1-ylpyrazine. M⁻(ESI): 456.7; M⁺(ESI): 458.6. HPLC: Rt: 2.7 min (HPLC purity: 85.8%).

Example 37

(2S,3R)-6-(4-ethoxyphenyl)-N,2-dihydroxy-3-{[4-(2-morpholin-4-ylethyl)piperazin-1-yl]-carbonyl}hexanamide (37)

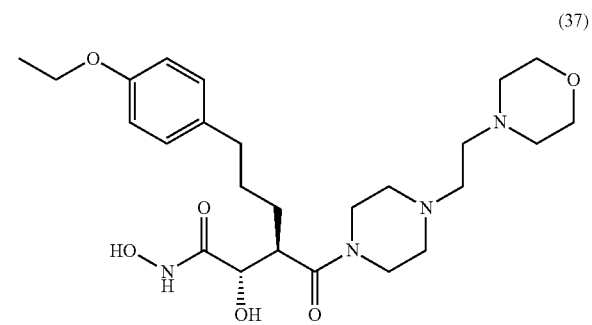

The title compound was prepared following the procedure of Example 19 using 4-(2-piperazin-1-ylethyl)morpholine. M⁻(ESI): 491.1; M⁺(ESI): 493.4. HPLC: Rt: 1.8 min (HPLC purity: 902%).

Example 38

(2S,3R)-3-{[4-(2-cyanophenyl)piperazin-1-yl]-carbonyl}-6-(4-ethoxyphenyl)-N,2-dihydroxyhexanamide (38)

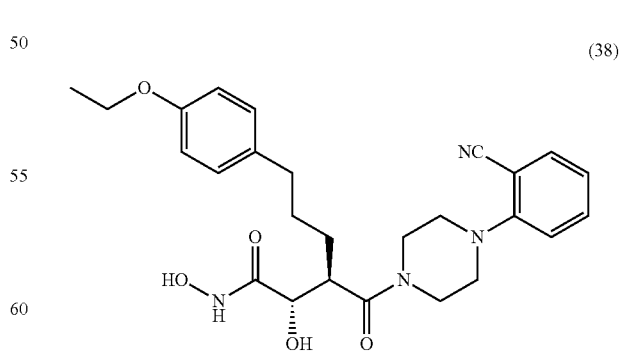

The title compound was prepared following the procedure of Example 19 using 2-piperazin-1-ylbenzonitrile. M⁻(ESI): 479.1; M⁺(ESI): 481.5. HPLC: Rt: 3.6 min (HPLC purity: 83%).

Example 39

(2S,3R)-3-{[4-(2-fluorophenyl)piperazin-1-yl]carbonyl}-N,2-dihydroxy-6-[4-(trifluoromethoxy)phenyl]hexanamide (39)

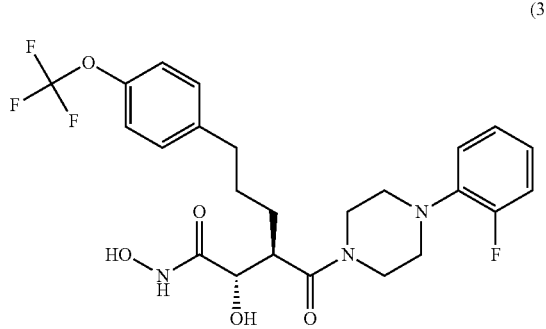

(39)

The title compound was prepared following the procedure of Example 19 using 1-(2-fluorophenyl)piperazine and (2R)-2-[(4S)-2,2-dimethyl-5-oxo-1,3-dioxolan-4-yl]-5-[4-(trifluoromethoxy)phenyl]pentanoic acid (Intermediate 10). M⁻(ESI): 512.6; M⁺(ESI): 514.7. HPLC: Rt: 3.9 min (HPLC purity: 93.4%).

Example 41

(2S,3R)—N,2-dihydroxy-3-[(4-pyridin-2-ylpiperazin-1-yl)carbonyl]-6-[4-(trifluoromethoxy)phenyl]hexanamide (41)

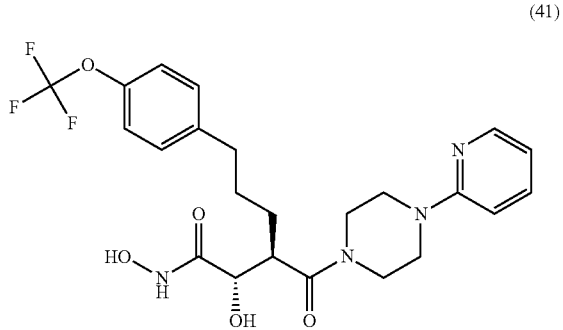

(41)

The title compound was prepared following the procedure of Example 19 using 1-pyridin-2-ylpiperazine and (2R)-2-[(4S)-2,2-dimethyl-5-oxo-1,3-dioxolan-4-yl]-5-[4-(trifluoromethoxy)phenyl]pentanoic acid (Intermediate 10). M⁻(ESI): 495.5; M⁺(ESI): 497.3. HPLC: Rt: 4.3 min (HPLC purity: 90.4%).

Example 40

(2S,3R)-3-{[4(6-chloropyridin-2-yl)piperazin-1-yl]carbonyl}-N,2-dihydroxy-6-[4-(trifluoromethoxy)phenyl]hexanamide (40)

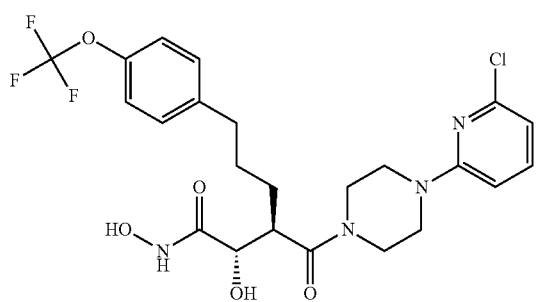

(40)

The title compound was prepared following the procedure of Example 19 using 1-(6-chloropyridin-2-yl)piperazine and (2R)-2-[(4S)-2,2-dimethyl-5-oxo-1,3-dioxolan-4-yl]-5-[4-(trifluoromethoxy)phenyl]pentanoic acid (Intermediate 10). M⁻(ESI): 529.0; M⁺(ESI): 531.1. HPLC: Rt: 4 min (HPLC purity: 97.9%).

Example 42

(2S,3R)-6-(4-ethoxyphenyl)-N,2-dihydroxy-3-[(4-{[4-(trifluoromethyl)pyrimidin-2-yl]amino}piperidin-1-yl)carbonyl]hexanamide (42)

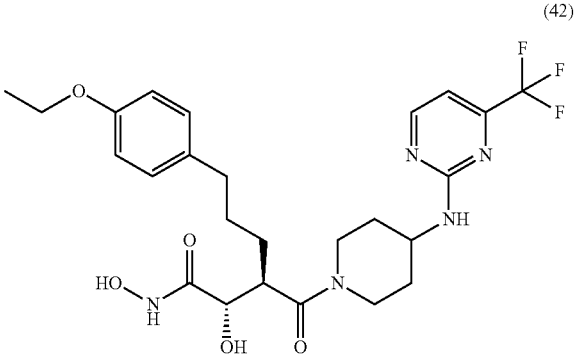

(42)

The title compound was prepared following the procedure of Example 19 using N-piperidin-4-yl-4-(trifluoromethyl)pyrimidin-2-amine. M⁻(ESI): 538.1; M⁺(ESI): 540.6. HPLC: Rt: 3.7 min (HPLC purity: 99.4%).

Example 43

(2S,3R)-6(4-ethoxyphenyl)-N,2-dihydroxy-3-({4-[(3-methoxyphenyl)amino]piperidin-1-yl}carbonyl)hexanamide (43)

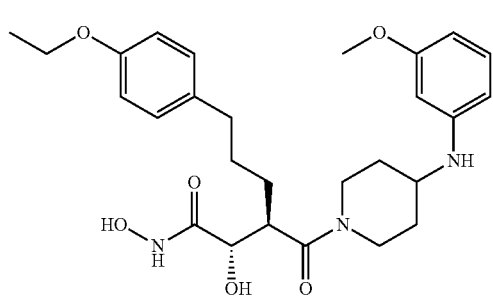

(43)

The title compound was prepared following the procedure of Example 19 using N-(3-methoxyphenyl)piperidin-4-amine. M⁻(ESI): 498.2; M⁺(ESI): 500.3. HPLC: Rt: 2.7 min (HPLC purity: 99.3%).

Example 44

(2S,3R)-3-[(4-{[3-(dimethylamino)phenyl]amino}piperidin-1-yl)carbonyl]-6-(4-ethoxyphenyl)-N,2-dihydroxyhexanamide (44)

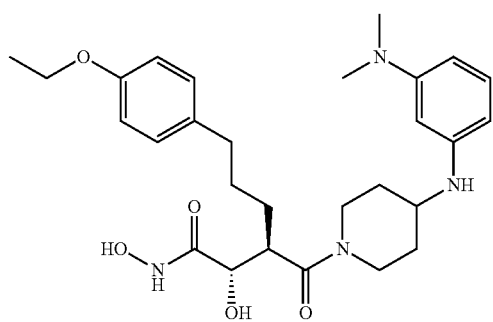

(44)

The title compound was prepared following the procedure of Example 19 using N,N-dimethyl-N-piperidin-4-ylbenzene-1,3-diamine. M⁻(ESI): 511.2; M⁺(ESI): 513.3. HPLC: Rt: 2.5 min (HPLC purity: 100%).

Example 45

(2S,3R)-3-({4-[(3-aminopyridin-2-yl)amino]piperidin-1-yl}carbonyl)-6-(4-ethoxyphenyl)-N,2-dihydroxyhexanamide (45)

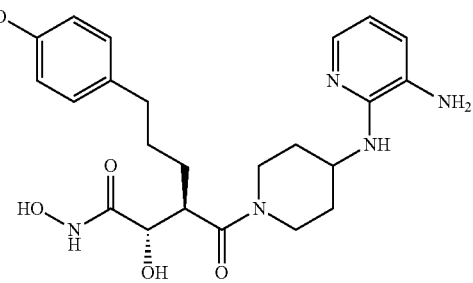

(45)

The title compound was prepared following the procedure of Example 19 using N²-piperidin-4-ylpyridine-2,3-diamine. M⁺(ESI): 486.3. HPLC: Rt: 2.3 min (HPLC purity: 96.3%).

Example 46

(2S,3R)-6-(4-ethoxyphenyl)-N,2-dihydroxy-3-({4-[(4-hydroxyphenyl)amino]piperidin-1-yl}carbonyl)hexanamide (46)

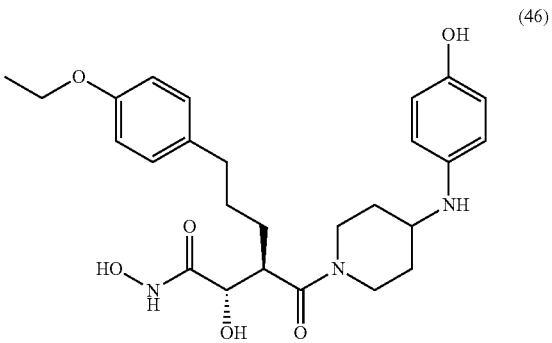

(46)

The title compound was prepared following the procedure of Example 19 using 4-(piperidin-4-ylamino)phenol. M⁺(ESI): 486.6. HPLC: Rt: 2.8 min (HPLC purity: 87.3%).

Example 47

(2S,3R)-6-(4-ethoxyphenyl)-3-{[(1S,4S)-5-(4-fluorophenyl)-2,5-diaza bicyclo[2.2.1]hept-2-yl]carbonyl}-N,2-dihydroxyhexanamide (47)

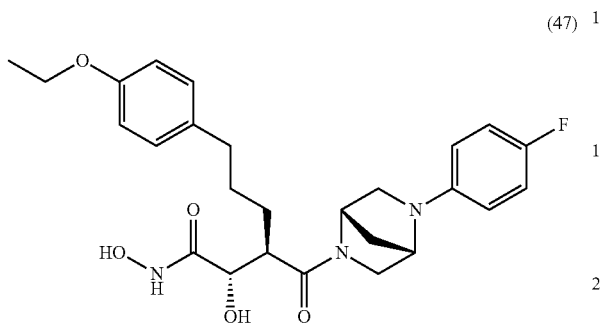

The title compound was prepared following the procedure of Example 19 using (1S,4S)-5-(4-fluorophenyl)-5-aza-2-azoniabicyclo[2.2.1]heptane chloride and DIEA. M⁻(ESI): 484.1; M⁺(ESI): 486.3. HPLC: Rt: 3.4 min (HPLC purity: 98.2%).

Example 48

(2R,3S)-N,2-dihydroxy-5-methyl-3-[(4-pyridin-2-ylpiperazin-1-yl)carbonyl]hexanamide (48)

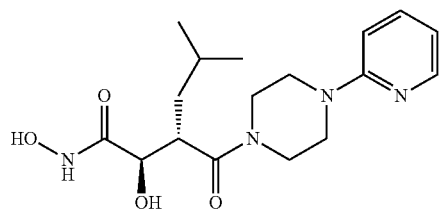

The title product was prepared following the procedure of Example 14 (step a and b) but starting from 1-(2-pyridyl)piperazine (Aldrich). Purification by reverse-phase chromatography gave the title product as a white powder. M⁻(ESI): 349.1; M⁺(ESI): 351.2. HPLC (Condition A): Rt: 1.1 min (HPLC purity: 100%).

Example 49

(2R,3S)-N,2-dihydroxy-5-methyl-3-({4-[4-(trifluoromethyl)phenyl]piperazin-1-yl}carbonyl)hexanamide (49)

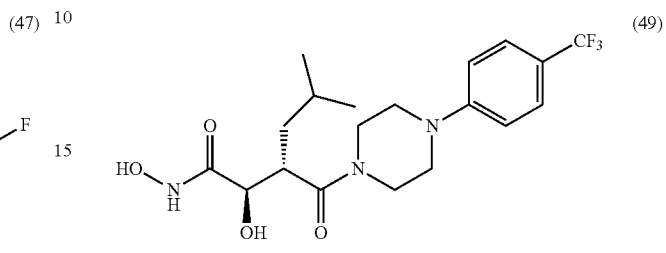

The title product was prepared following the procedure of Example 14 (step a and b) but starting from 1-(4-trifluoromethylphenyl)-piperazine (Chess). Purification by reverse-phase chromatography gave the title product as a white powder. M⁻(ESI): 416.3; M⁺(ESI): 418.3. HPLC (Condition A): Rt: 3.4 min (HPLC purity: 98.8%).

Example 50

(2R,3S)-3-{[4-(2-fluorophenyl)piperazin-1-yl]-carbonyl}-N,2-dihydroxy-5-methylhexanamide (50)

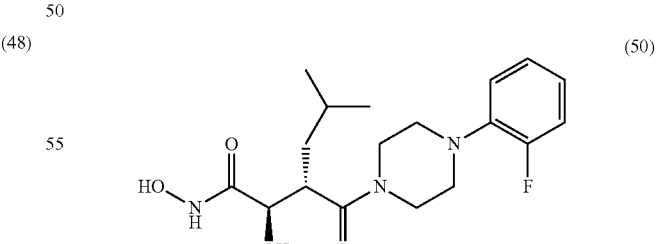

The title product was prepared following the procedure of Example 14 (step a and b) but starting from 1-(2-fluorophenyl)piperazine (Aldrich). Purification by reverse-phase chromatography gave the title product as a white powder. M⁻(ESI): 366.2; M⁺(ESI): 368.2. HPLC (Condition A): Rt: 2.7 min (HPLC purity: 99.7%).

Example 51

(2R,3S)-N,2-dihydroxy-5-methyl-3-[(4-pyrimidin-2-ylpiperazin-1-yl)carbonyl]hexanamide (51)

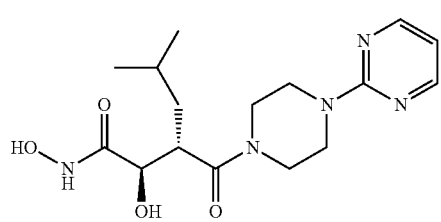

(51)

The title product was prepared following the procedure of Example 14 (step a and b) but starting from 1-(2-pyrimidyl)piperazine (Emkachem). Purification by reverse-phase chromatography gave the title product as a white powder. M⁻(ESI): 350.2; M⁺(ESI): 352.2. HPLC (Condition A): Rt: 1.4 min (HPLC purity: 100%).

Example 52

(2S,3S)-N,2-dihydroxy-5-methyl-3-({(2R)-2-methyl-4-[4-(trifluoromethoxy)phenyl]piperazin-1-yl}carbonyl)hexanamide (52)

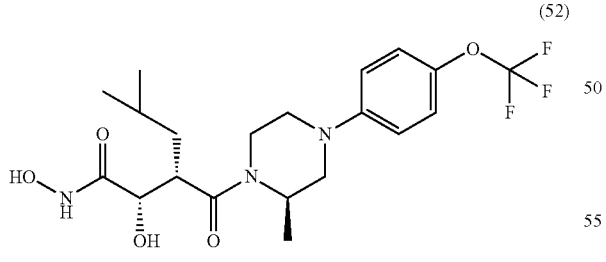

(52)

The title product was prepared following the procedure of Example 4 (step a and b) but starting from (3R)-3-methyl-1-(4-trifluoromethoxyphenyl)-piperazine. Purification by reverse-phase chromatography gave the title product as a white powder. M⁻(ESI): 446.2; M⁺(ESI): 448.3. HPLC (Condition A): Rt: 4.0 min (HPLC purity: 83%).

Example 53

(2S,3S)-3-{[(2R)-4-biphenyl-4-yl-2-methylpiperazin-1-yl]carbonyl}-N,2-dihydroxy-5-methylhexanamide (53)

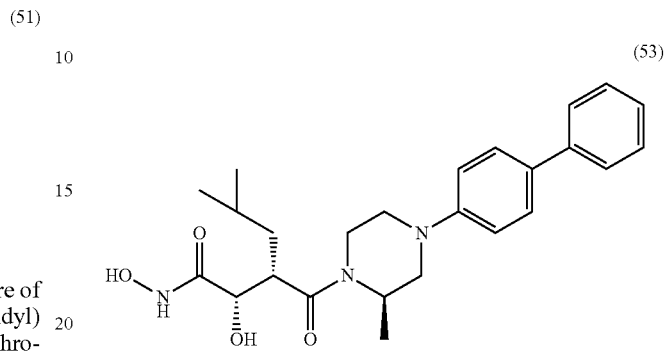

(53)

The title product was prepared following the procedure of Example 4 (step a and b) but starting from (3R)-1-biphenyl-4-yl-3-methyl-piperazine. Purification by reverse-phase chromatography gave the title product as a white powder. M⁻(ESI): 438.2; M⁺(ESI): 440.3. HPLC (Condition A): Rt: 3.7 min (HPLC purity: 100%).

Example 54

(2S,3S)-3-{[(2S)-4-(2-fluorophenyl)-2-methylpiperazin-1-yl]carbonyl}-N,2-dihydroxy-5-methylhexanamide (54)

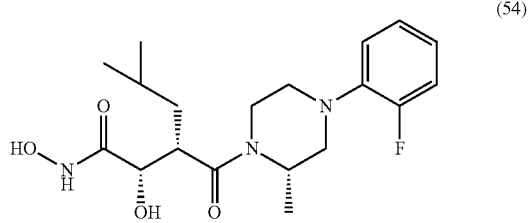

(54)

The title product was prepared following the procedure of Example 4 (step a and b) but starting from (3S)-1-(2-fluorophenyl-3-methylpiperazine (Intermediate 6). Purification by reverse-phase chromatography gave the title product as a white powder. M⁻(ESI): 380.2; M⁺(ESI): 382.1. HPLC (Condition A): Rt: 3.1 min (HPLC purity: 92.4%).

Example 55

(2S,3S)-3-{[(2R)-4-(3-chlorophenyl)-2-methylpiperazin-1-yl]carbonyl}-N,2-dihydroxy-5-methylhexanamide (55)

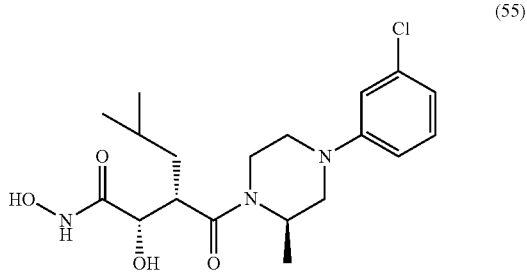
(55)

The title product was prepared following the procedure of Example 4 (step a and b) but starting from (3R)-1-(3-chlorophenyl)-3-methyl-piperazine. Purification by reverse-phase chromatography gave the title product as a white powder. M⁻(ESI): 396.2; M⁺(ESI): 398.1. HPLC (Condition A): Rt: 3.4 min (HPLC purity: 98.5%).

Example 56

(2R,3S)-N,2-dihydroxy-5-methyl-3-{[4-(5-phenyl-1,2,4-oxadiazol-3-yl)piperazin-1-yl]-carbonyl}hexanamide (56)

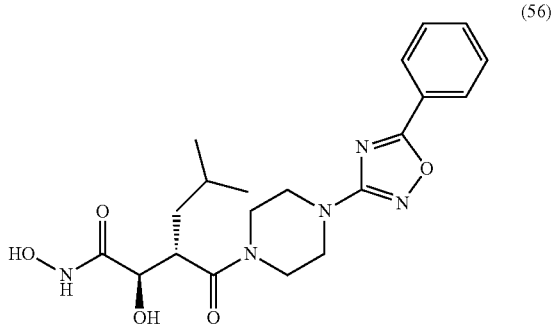
(56)

Step a) Formation of (5R)-2,2-dimethyl-5-((1S)-3-methyl-1-{[4-(5-phenyl-1,2,4-oxadiazol-3-yl)-1-piperazinyl]carbonyl}butyl)-1,3-dioxolan-4-one

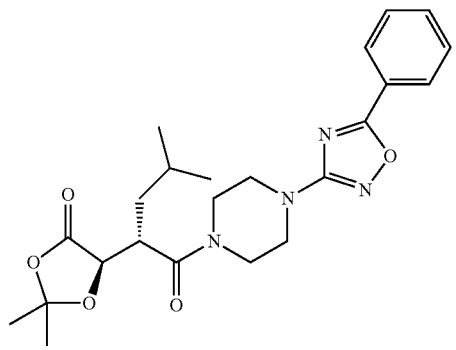

To a cold solution (−15° C.) of (2S)-2-[(4R)-2,2-dimethyl-5-oxo-1,3-dioxolan-4-yl]-4-methylpentanoic acid (150 mg, 0.65 mmol, prepared according to WO 94/02447 or similarly to Seebach et al., 1990, *Org. Syntheses, Coll. Vol. III*, p 153-159 but starting from diisopropyl (R)-(+)-malate) in anhydrous DCM (1.8 mL) were added DIEA (115 µL, 0.69 mmol), 1-hydroxy-7-azabenzotriazole (89 mg, 0.65 mmol, Fluka) and fluoro-N,N,N',N'-tetramethylformamidinium hexafluorophosphate (206 mg, 0.78 mmol, Aldrich). The reaction mixture was stirred at −15° C. for 15 min and at RT for 1 h, then cooled at 0° C. A solution of 1-(5-phenyl-[1,2,4]oxadiazol-3-yl)piperazine (230 mg, 0.78 mmol, Intermediate 11 parent form) and DIEA (115 µL, 0.69 mmol) in anhydrous DCM (1 mL) was added. The reaction mixture was stirred for 5 hours at RT and then poured on a silica column (wet with c-Hex/EtOAc 4:1). Purification was performed with a gradient cHex/EtOAc 4:1 to c-Hex/EtOAc 3:1 to give 120 mg (42%) of the title compound as a white powder. HPLC, Rt: 4.5 min (purity: 100%). LC/MS, M⁺(ESI): 443.3.

Step b) Formation of (2R,3S)-N,2-dihydroxy-5-methyl-3-{[4-(5-phenyl-1,2,4-oxadiazol-3-yl)piperazin-1-yl]carbonyl}hexanamide (58)

The title product was prepared following the procedure of Example 14 (step b) but starting from (5R)-2,2-dimethyl-54 (1S)-3-methyl-1-{[4-(5-phenyl-1,2,4-oxadiazol-3-yl)-1-piperazinyl]carbonyl}butyl)-1,3-dioxolan-4-one. Purification by reverse-phase chromatography gave the title product as a white powder. M⁻(ESI): 416.2; M⁺(ESI): 418.3. HPLC (Condition A): Rt: 3.1 min (HPLC purity: 99.3%).

Example 57

(2S,3S)-N,2-dihydroxy-5-methyl-3-{[(2R)-2-methyl-4-(5-phenylpyridin-2-yl)piperazin-1-yl]-carbonyl}hexanamide (57)

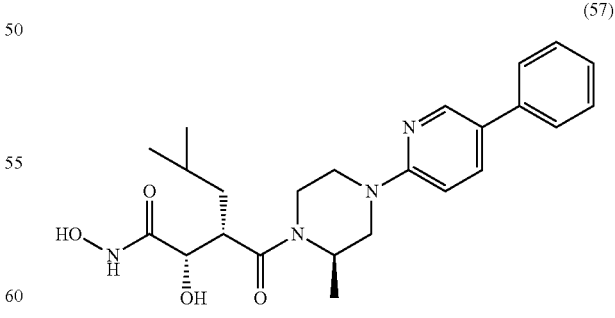
(57)

The title product was prepared following the procedure of Example 4 (step a and b) but starting from (3R)-3-methyl-1-(5-phenyl-pyridin-2-yl)-piperazine. Purification by reverse-phase chromatography gave the title product as a white powder. M⁻(ESI): 4393; M⁺(ESI): 441.4. HPLC (Condition A): Rt: 2.3 min (HPLC purity: 97.0%).

Example 58

3-[(4-biphenyl-4-ylpiperazin-1-yl)carbonyl]-3,4-dideoxy-1-(hydroxy amino)-5-O-(phenylmethyl)-L-threo-pentose (58)

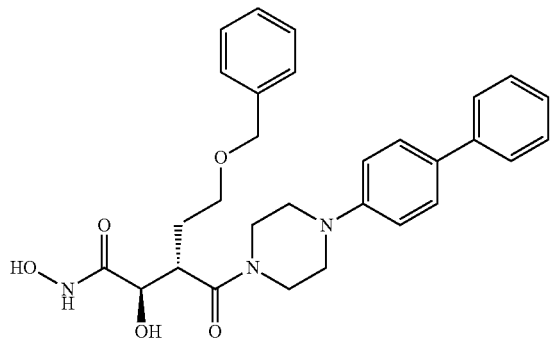

(58)

Step a) Formation of 3-[(4-biphenyl-4-ylpiperazin-1-yl)carbonyl]-3,4-dideoxy-1,2-O-(1-methylethylidene)-5-O-(phenylmethyl)-L-threo-pentonic acid

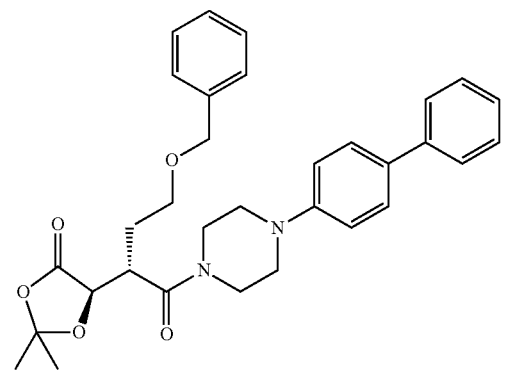

The title product was prepared following the procedure of Example 4 (step a) but starting from 5-O-benzyl-3-carboxy-3,4-dideoxy-1,2-O-(1-methylethylidene)-L-threo-pentonic acid (327 mg, 1.06 mmol, Intermediate 13). Purification by chromatography on silicagel EtOAc/c-hex (20/80) for 5 min up to 50/50 in 20 min gave a the title product as a colorless oil (300 mg, 54%). M⁺(ESI): 529.4. HPLC (Condition A): Rt: 4.9 min (HPLC purity: 90.7%).

Step b) Formation of 3-[(4-biphenyl-4-ylpiperazin-1-yl)carbonyl]-3,4-dideoxy-1-(hydroxyamino)-5-O-(phenylmethyl)-L-threo-pentose The title product was prepared following the procedure of Example 4 (step b) but starting from 3-[(4-biphenyl-4-ylpiperazin-1-yl)carbonyl]-3,4-dideoxy-1,2-O-(1-methylethylidene)-5-O-(phenylmethyl)-L-threo-pentonic acid (300 mg). Purification by reverse-phase chromatography gave the title product as a white powder (55 mg, 19%). M⁻(ESI): 502.1; M⁺(ESI): 504.2. HPLC (Condition A): Rt: 3.6 min (HPLC purity: 94.1%).

Example 59

(2R,3S)-3-({4-[5-(4-fluorophenyl)-1,3,4-oxadiazol-2-yl]piperidin-1-yl}carbonyl)-N,2-dihydroxy-5-methylhexanamide (59)

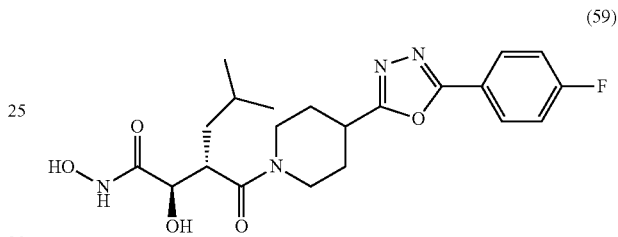

(59)

The title product was prepared following the procedure of Example 14 (step a and b) but starting from 4-[5-(4-fluorophenyl)-1,3,4-oxadiazol-2-yl]piperidine (Peakdale). Purification by reverse-phase chromatography gave the title product as a white powder. M⁻(ESI): 433.3; M⁺(ESI): 435.3. HPLC (Condition A): Rt: 2.7 min (HPLC purity: 97.8%).

Example 60

(2R,3S)-3-{[4-(4-fluorophenyl)-3,6-dihydropyridin-1(2H)-yl]-carbonyl}-N,2-dihydroxy-5-methylhexanamide (60)

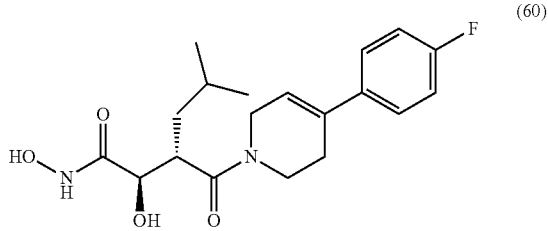

(60)

The title product was prepared following the procedure of Example 56 (step a and b) but starting from 4-(4-fluorophenyl)-1,2,3,6-tetrahydropyridine hydrochloride (Acros). Purification by reverse-phase chromatography gave the title product as a white powder. M⁻(ESI): 363.2; M⁺(ESI): 365.2. HPLC (Condition A): Rt: 3.2 min (HPLC purity: 99.4%).

Example 61

(2R,3S)-N,2-dihydroxy-5-methyl-3-[(4-phenyl-3,6-dihydropyridin-1(2H)-yl)carbonyl]hexanamide (61)

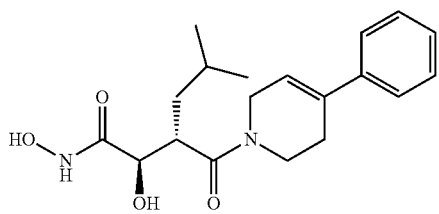

The title product was prepared following the procedure of Example 56 (step a and b) but starting from 4-phenyl-1,2,3,6-tetrahydropyridine hydrochloride (Acros). Purification by reverse-phase chromatography gave the title product as a white powder. M⁻(ESI): 345.2; M⁺(ESI): 347.2. HPLC (Condition A): Rt: 3.1 min (HPLC purity: 99.4%).

Example 62

(2R,3S)-N,2-dihydroxy-5-methyl-3-{[4-(5-pyridin-4-yl-1,2,4-oxadiazol-3-yl)piperazin-1-yl]-carbonyl}hexanamide (62)

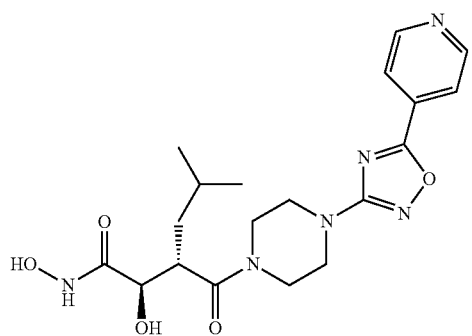

The title product was prepared following the procedure of Example 14 (step a and b) but starting from 1-(pyridin-4-yl-[1,2,4]oxadiazol-3-yl)-piperazine dihydrochloride (Intermediate 12). Purification by reverse-phase chromatography gave the title product as a white powder. M⁻(ESI): 417.2; M⁺(ESI): 419.2. HPLC (Condition A): Rt: 1.9 min (HPLC purity: 100%).

Example 63

(2R,3S)-3-{[4-(4-chlorophenyl)-3,6-dihydropyridin-1(2H)-yl]carbonyl}-N,2-dihydroxy-5-methylhexanamide (63)

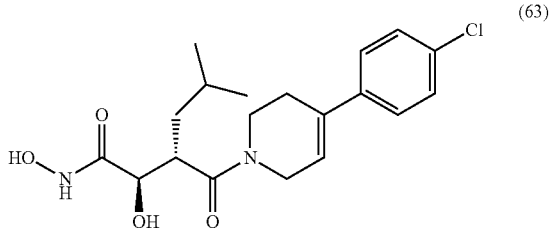

The title product was prepared following the procedure of Example 56 (step a and b) but starting from 4-(4-chlorophenyl)-1,2,3,6-tetrahydropyridine hydrochloride (Aldrich). Purification by reverse-phase chromatography gave the title product as a white powder. M⁻(ESI): 379.3; M⁺(ESI): 381.2. HPLC (Condition A): Rt: 3.4 min (HPLC purity: 99.2%).

Example 64

(2S,3R)-6-(4-ethoxyphenyl)-N,2-dihydroxy-3-({4-[2-(2-thienyl)ethyl]piperazin-1-yl}-carbonyl)hexanamide (64)

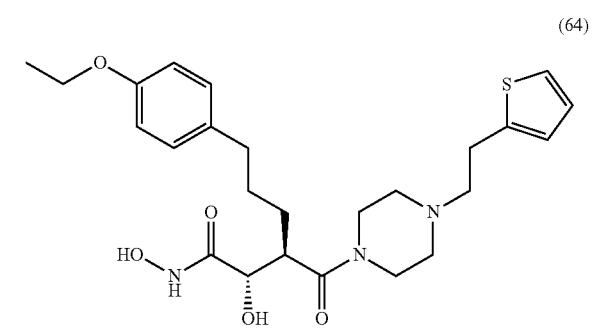

Step a) Formation of (5S)-5-[(1R)-4-(4-ethoxyphenyl)-1-({4-[2-(2-thienyl)ethyl]-1-piperazinyl}carbonyl)butyl]-2,2-dimethyl-1,3-dioxolan-4-one

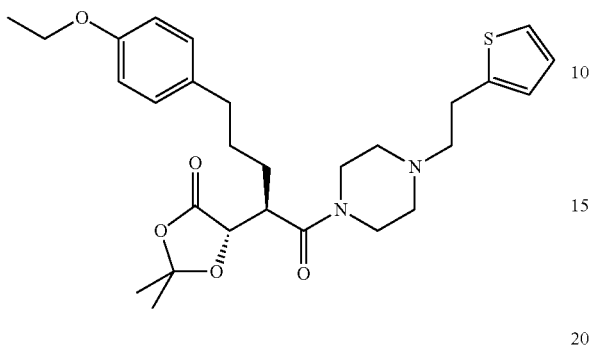

To a cold solution (0° C.) of (2R)-2-[(4S)-2,2-dimethyl-5-oxo-1,3-dioxolan-4-yl]-5-(4-ethoxyphenyl)pentanoic acid (150 mg, 0.45 mmol, intermediate 2) in anhydrous DCM (3 mL) were added DMA (80 μL, 0.47 mmol) and fluoro-N,N,N',N'-tetramethyl formamidinium hexafluorophosphate (130 mg, 0.49 mmol, Aldrich). The reaction mixture was stirred at 0° C. for 30 min. Then a solution of 1-(2-thienylethyl)-piperazine (96 mg, 0.49 mmol, Emkachem) and DIEA (80 μL, 0.47 mmol) in anhydrous DCM (1 mL) was added. The reaction mixture was stirred for 3 hours at RT and then poured on a silica column (30 g, wet with c-Hex/EtOAc 4:1). Purification was performed with a gradient cHex/EtOAc 4:1 to c-Hex/EtOAc 1:1 in 30 min to give 101 mg (44%) of the title compound as a colourless oil. M⁻(ESI): 513.2; M⁺(ESI): 515.4. HPLC, Rt: 3.4 min (purity: 97.9%).

Step b) Formation of (2S,3R)-6-(4-ethoxyphenyl)-N,2-dihydroxy-3-({4-[2-(2-thienyl)ethyl]piperazin-1-yl}carbonyl)hexanamide (66)

To a solution of (5S)-5-[(1R)-4-(4-ethoxyphenyl)-1-({4-[2-(2-thienyl)ethyl]-1-piperazinyl}carbonyl)butyl]-2,2-dimethyl-1,3-dioxolan-4-one (101 mg, 0.20 mmol) in iPrOH (3 mL) was added a 50% aqueous solution of hydroxylamine (60 μL) and the resulting mixture was stirred at RT for 1 hour. Then water (12 mL) was added and the resulting mixture was purified by reverse-phase chromatography (using a mixture of water and iPrOH with a ratio from 4:1 to 1:1 as eluent) to give 40 mg (42%) of the title compound as a white powder. M⁻(ESI): 488.4; M⁺(ESI): 490.4. HPLC, Rt: 2.5 min (purity: 97.0%).

Example 65

(2S,3R)-3-[(4-cyclohexylpiperazin-1-yl)carbonyl]-6-(4-ethoxyphenyl)-N,2-dihydroxyhexanamide (65)

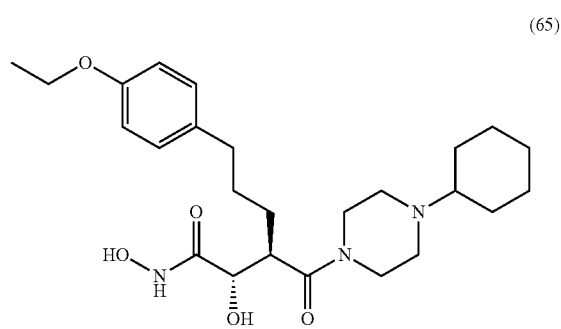

The title product was prepared following the procedure of Example 64 (step a and b) but starting from 1-cyclohexylpiperazine (Spectrum). Purification by reverse-phase chromatography gave the title product as a white powder. M⁻(ESI): 460.3; M⁺(ESI): 462.3. HPLC (Condition A): Rt: 2.3 min (HPLC purity: 100%).

Example 66

(2S,3R)-6(4-ethoxyphenyl)-N,2-dihydroxy-3-{[4-(2-hydroxyethyl)piperidin-1-yl]-carbonyl}hexanamide (66)

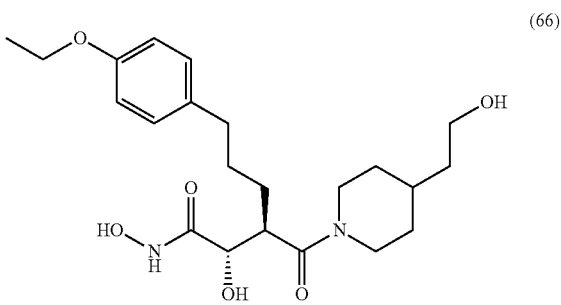

The title product was prepared following the procedure of Example 64 (step a and b) but starting from 4-piperidineethanol (Aldrich). Purification by reverse-phase chromatography gave the title product as a white powder. M⁻(ESI): 421.2; M⁺(ESI): 423.3. HPLC (Condition A): Rt: 2.5 min (HPLC purity: 78.8%).

Example 67

(2S,3R)-6(4-ethoxyphenyl)-3-{[4-(4-fluorophenyl)piperidin-1-yl]carbonyl}-N,2-dihydroxyhexanamide (67)

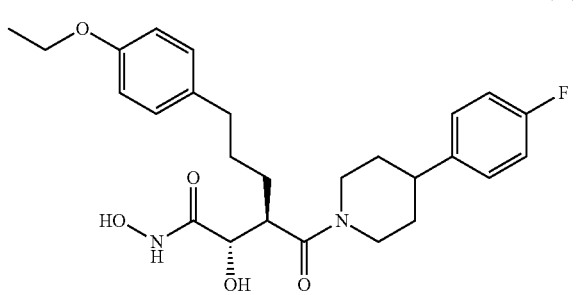

The title product was prepared following the procedure of Example 64 (step a and b) but starting from 4-(4-fluorophenyl)piperidine hydrochloride (Arch). Crystallization from the reaction mixture followed by filtration and washing with water gave the title product as a white powder. M⁻(ESI): 471.4; M⁺(ESI): 473.4. HPLC (Condition A): Rt: 3.7 min (HPLC purity: 99.7%).

Example 68

(2S,3R)—N,2-dihydroxy-6-(4-methoxyphenyl)-3-[(4-propylpiperidin-1-yl)carbonyl]hexanamide (68)

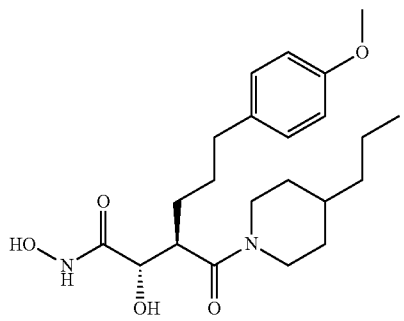

The title product was prepared following the procedure of Example 64 (step a and b) but starting from (2R)-2-[(4S)-2,2-dimethyl-5-oxo-1,3-dioxolan-4-yl]-5-(4-methoxyphenyl)pentanoic acid (prepared following the procedure of Intermediate 2 but using 4-bromoanisole in step b) and 4-propylpiperidine (Aldrich). Purification by reverse-phase chromatography gave the title product as a yellow powder. M⁻(ESI): 405.4; M⁺(ESI): 407.4. HPLC (Condition A): Rt: 3.6 min (HPLC purity: 94.9%).

Example 69

(2S,3S)-3-{[4-(2-fluorophenyl)piperazin-1-yl]carbonyl}-N,2-dihydroxy-5-methylhexanamide (69)

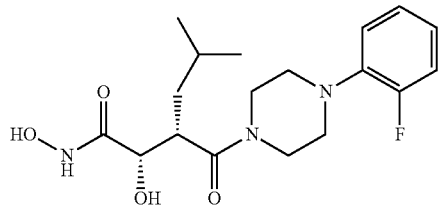

The title compound was prepared following the procedure of Example 4 (step a and b), but starting from 1-(2-fluorophenyl)piperazine. Purification by reverse-phase chromatography gave the title product as a light pink powder. M⁺(ESI): 366.2; M⁺(ESI): 368.4. HPLC (Condition A), Rt: 2.7 min (HPLC purity: 95.1%).

Example 70

(2R,3S)-N,2-dihydroxy-5-methyl-3-({4-[5-(2-thienyl)-1,2,4-oxadiazol-3-yl]piperazin-1-yl}-carbonyl)hexanamide (70)

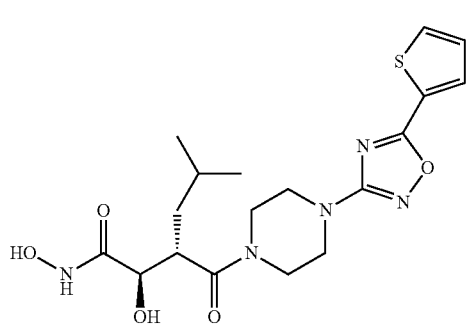

The title compound was prepared following the procedure of Example 4 (step a and b), but starting from 1-[5-(2-thienyl)-1,2,4-oxadiazol-3-yl]piperazine. The title compound was purified by crystallization in EtOAc/iPr₂O as an off white solid. M⁻(ESI): 422.4; M⁺(ESI): 424.4. HPLC (Condition A), Rt: 2.9 min (HPLC purity: 97.8%).

Example 71

(2R,3S)-3-{[(2R)-4-(5-chloropyridin-2-yl)-2-methylpiperazin-1-yl]carbonyl}-N,2-dihydroxy-5-methylhexanamide (71)

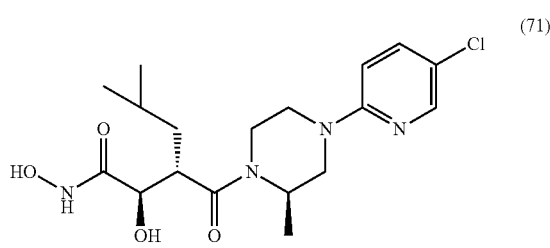

The title compound was prepared following the procedure of Example 4 (step a and b), but starting from (3R)-1-(5-chloropyridin-2-yl)-3-methylpiperazine hydrobromide and DIEA. Purification by reverse-phase chromatography gave the title product as a white solid. M⁻(ESI): 397.2; M⁺(ESI): 399.2. HPLC (Condition A), Rt: 1.9 min (HPLC purity: 99.8%).

Example 72

(2H,3S)-3-{[4(5-chloropyridin-2-yl)piperazin-1-yl]-carbonyl}-N,2-dihydroxy-5-methylhexanamide (72)

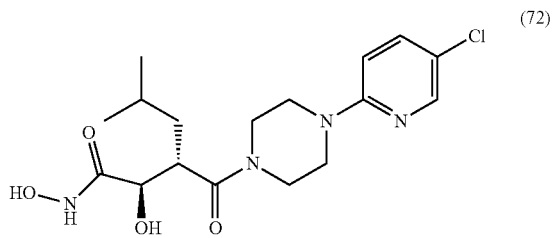

The title compound was prepared following the procedure of Example 14 (step a and b), but starting from 1-(5-chloropyridin-2-yl)piperazine. Purification by reverse-phase chromatography gave the title product as a white powder. M⁻(ESI): 383.2; M⁺(ESI): 385.2. HPLC (Condition A), Rt: 1.7 min (HPLC purity: 99.8%).

Example 73

(2R,3S)-3-{[4(5-bromopyridin-2-yl)piperazin-1-yl]carbonyl}-N,2-dihydroxy-5-methylhexanamide (73)

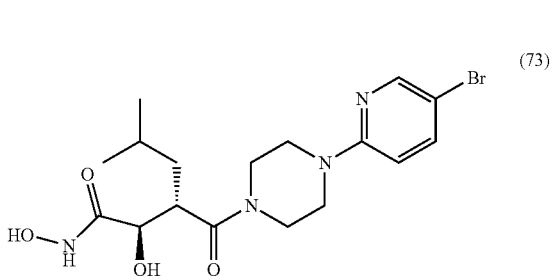

The title compound was prepared following the procedure of Example 14 (step a and b), but starting from 1-(5-bromopyridin-2-yl)piperazine. Purification by reverse-phase chromatography gave the title product as a white solid. M⁻(ESI): 427.0; M⁺(ESI): 429.2. HPLC (Condition A), Rt: 1.8 min (HPLC purity: 100%).

Example 74

(2S,3S)-3-{[(2R)-4-(4-chlorophenyl)-2-methylpiperazin-1-yl]carbonyl}-N,2-dihydroxy-5-methylhexanamide (74)

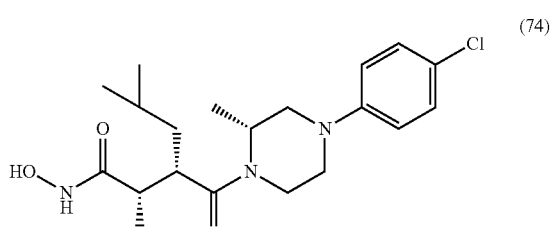

The title compound was prepared following the procedure of Example 4 (step a and b), but starting from (3R)-1-(4-chlorophenyl)-3-methylpiperazine. Purification by reverse-phase chromatography gave the title product as a white powder. M⁻(ESI): 396.2; M⁺(ESI): 398.2. HPLC (Condition A), Rt: 3.5 min (HPLC purity: 99.1%).

Example 75

(2S,3S)-N,2-dihydroxy-5-methyl-3-({(2R)-2-methyl-4-[5-(trifluoromethyl)pyridin-2-yl]piperazin-1-yl}carbonyl)hexanamide (75)

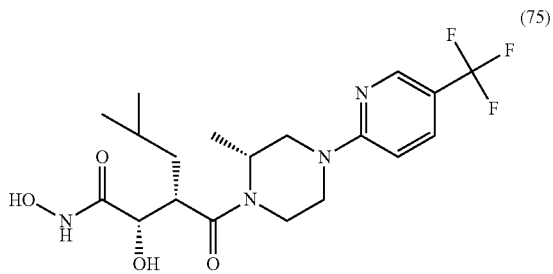

The title compound was prepared following the procedure of Example 4 (step a and b), but starting from (3R)-3-methyl-1-[5-(trifluoromethyl)pyridin-2-yl]piperazine. Purification by reverse-phase chromatography gave the title product as a white powder. M⁻(ESI): 431.3; M⁺(ESI): 433.3. HPLC (Condition A), Rt: 2.8 min (HPLC purity: 96.5%).

Example 76

(2R,3S)-3-benzyl-N,2-dihydroxy-4-oxo-4-{4-[4-(trifluoromethoxy)phenyl]piperazin-1-yl}butanamide (76)

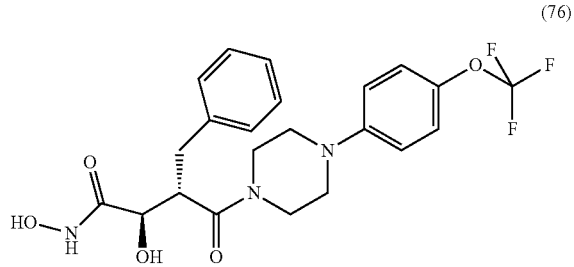

The title compound was prepared following the procedure of Example 4 (step a and b), but starting from 1-[4-(trifluoromethoxy)phenyl]piperazine. Purification by reverse-phase chromatography gave the title product as a white powder (yield 63%). M⁻(ESI): 466.0; M⁺(ESI): 467.9. HPLC (Condition A), Rt: 3.4 min (HPLC purity: 99.7%).

Example 77

(2S,3S)-3-benzyl-N,2-dihydroxy-4-{(2R)-2-methyl-4-[4-(trifluoro methoxy)phenyl]piperazin-1-yl}-4-oxobutanamide (77)

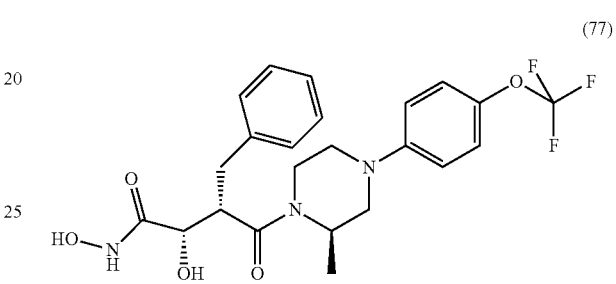

The title compound was prepared following the procedure of Example 4 (step a and b), but starting from (3R)-3-methyl-1-[4-(trifluoromethoxy)phenyl]piperazine dihydrochloride. Purification by reverse-phase chromatography gave the title product as a slightly pink solid (yield 27%). M⁻(ESI): 480.3; M⁺(ESI): 482.2. HPLC (Condition A), Rt: 3.8 min (HPLC purity: 100%).

Example 78

(2R,3S)-N,2-dihydroxy-3-methyl-4-oxo-4-{4-[4-(trifluoromethoxy)phenyl]piperazin-1-yl}butanamide (78)

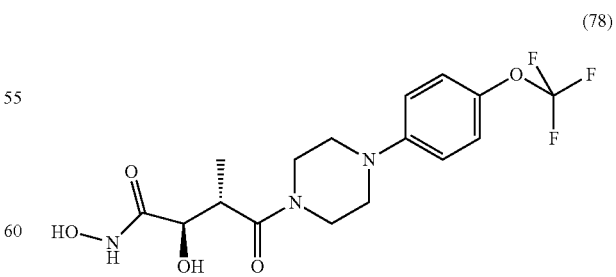

The title compound was prepared following the procedure of Example 4 (step a and b), but starting from 1-[4-(trifluoromethoxy)phenyl]piperazine. Purification by reverse-phase chromatography gave the title product as a white powder (yield 46%). M⁻(ESI): 375.2; M⁺(ESI): 377.4. HPLC (Condition A), Rt: 2.6 min (HPLC purity: 97.0%).

Example 79

(2S)-N,2-dihydroxy-3-methyl-4-{(2R)-2-methyl-4-[4-(trifluoromethoxy)phenyl]piperazin-1-yl}-4-oxobutanamide (79)

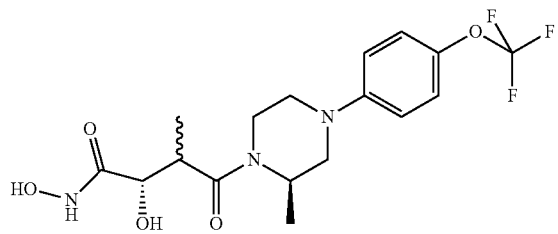

(79)

The title compound was prepared following the procedure of Example 4 (step a and b), but starting from (3R)-3-methyl-1-[4-(trifluoromethoxy)phenyl]piperazine. Purification by reverse-phase chromatography gave the title product (mixture of diastereoisomers) as a white powder (yield 74%). M⁻(ESI): 404.3; M⁺(ESI): 406.3. HPLC (Condition A), Rt: 3.0 min (HPLC purity: 99.6%).

Example 80

(2S,3S)-3-{[(2R)-4-(4'-fluorobiphenyl-4-yl)-2-methylpiperazin-1-yl]carbonyl}-N,2-dihydroxy-5-methylhexanamide (80)

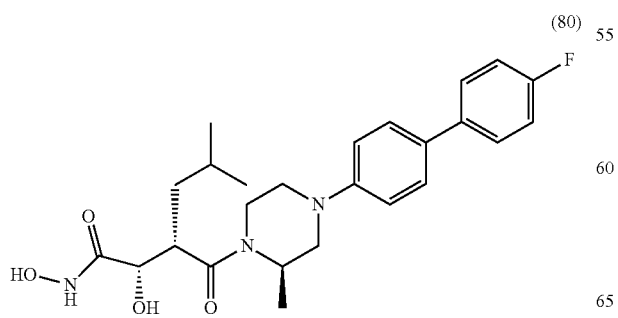

(80)

Step a) Formation of (5S)-5-((1S)-1-{[(2R)-4-(4'-fluorobiphenyl-4-yl)-2-methylpiperazin-1-yl]carbonyl}-3-methylbutyl)-2,2-dimethyl-1,3-dioxolan-4-one

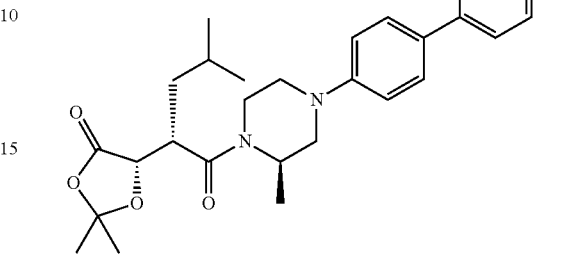

The title compound was prepared following the procedure of Example 4 (step a) but starting from (3R)-1-(4'-fluorobiphenyl-4-yl)-3-methylpiperazine. The crude product (mixture of 2 diastereoisomer) was purified by chromatography (SiO₂, 20/80 iPr₂O/c-hex) to give the title compound as a single diastereoisomer (21%). HPLC (Condition A), Rt: 5.2 min (HPLC purity: 100%). M⁺(ESI): 483.6.

Step b) Formation of (2S,3S)-3-{[(2R)-4-(4'-fluorobiphenyl-4-yl)-2-methylpiperazin-1-yl]carbonyl}-N,2-dihydroxy-5-methylhexanamide To a suspension of (5S)-5-((1S)-1-{[(2R)-4-(4'-fluorobiphenyl-4-yl)-2-methylpiperazin-1-yl]carbonyl}-3-methylbutyl)-2,2-dimethyl-1,3-dioxolan-4-one (230 mg, 0.48 mmol, 1.0 eq) in a mixture of iPrOH (4 mL) and THF (4 mL) was added a 50% aq. solution hydroxylamine (0.08 mL, 1.43 mmol, 3.0 eq). The reaction mixture was stirred at rt for 8 h. Evaporation of the solvent gave a white solid. This product was washed with iPr₂O (2×), filtered and dried under vacuum to give the title compound as a white powder (89%). M⁻(EST): 456.3; M⁺(ESI): 458.4. HPLC (Condition A), Rt: 3.9 min (HPLC purity: 97.5%).

Example 81

(2S,3S)-3-{[(2R)-4-(4-ethoxyphenyl)-2-methylpiperazin-1-yl]-carbonyl}-N,2-dihydroxy-5-methylhexanamide (81)

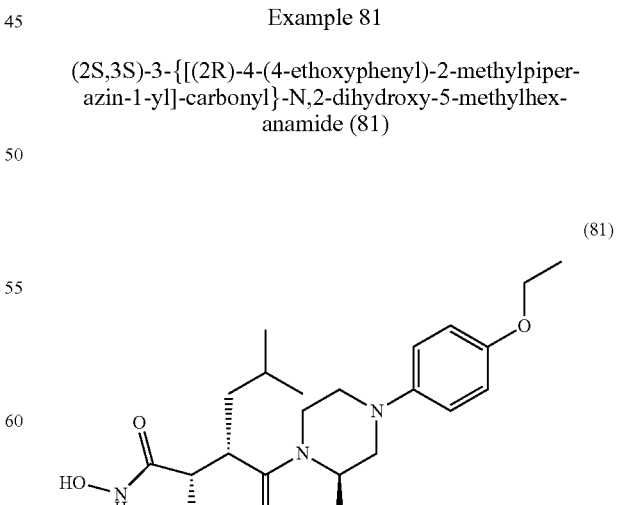

(81)

The title compound was prepared following the procedure of Example 80 (step a and b), but starting from (3R)-1-(4- ethoxyphenyl)-3-methylpiperazine. Purification by reverse-phase chromatography gave the title product as a white solid. M⁻(ESI): 406.4; M⁺(ESI): 408.4. HPLC (Condition A), Rt: 2.5 min (HPLC purity: 99.0%).

Example 82

(2S,3S)-3-{[(2R)-4-(3,4-dimethoxyphenyl)-2-methylpiperazin-1-yl]carbonyl}-N,2-dihydroxy-5-methylhexanamide (82)

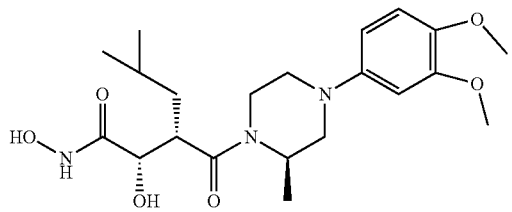

(82)

The title compound was prepared following the procedure of Example 80 (step a and b), but starting from (3R)-1-(3,4-dimethoxyphenyl)-3-methylpiperazine. Purification by reverse-phase chromatography gave the title product as a white solid. M⁻(ESI): 422.4; M⁺(ESI): 424.4. HPLC (Condition A), Rt: 2.1 min (HPLC purity: 100%).

Example 83

(2S,3S)-N,2-dihydroxy-5-methyl-3-({(2R)-2-methyl-4-[4-(methylsulfonyl)phenyl]piperazin-1-yl}-carbonyl)hexanamide (83)

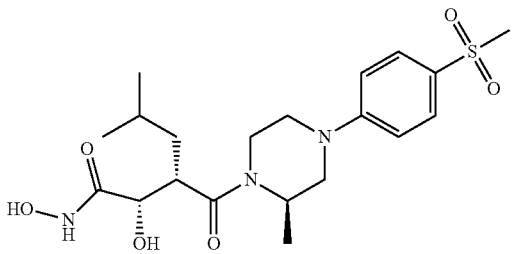

(83)

The title compound was prepared following the procedure of Example 80 (step a and b), but starting from (3R)-3-methyl-1-[4-(methylsulfonyl)phenyl]piperazine. Purification by reverse-phase chromatography gave the title product as a white solid. M⁻(ESI): 440.4; M⁺(ESI): 442.2. HPLC (Condition A), Rt: 2.4 min (HPLC purity: 99.5%).

Example 84

(2S,3S)-N,2-dihydroxy-3-{[(2R)-4-(6-methoxy-2-naphthyl)-2-methylpiperazin-1-yl]carbonyl}-5-methylhexanamide (84)

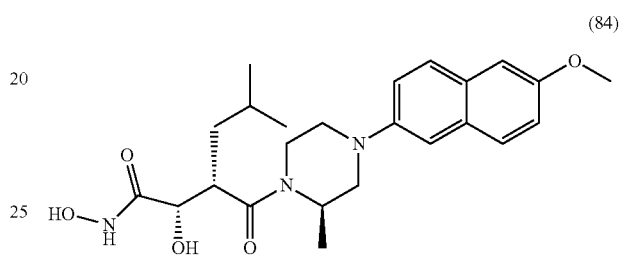

(84)

The title compound was prepared following the procedure of Example 80 (step a and b), but starting from (3R)-1-(6-methoxy-2-naphthyl)-3-methylpiperazine. Purification by reverse-phase chromatography gave the title product as a white powder. M⁻(ESI): 442.5; M⁺(ESI): 444.5. HPLC (Condition A), Rt: 3.3 min (HPLC purity: 98.3%).

Example 85

(2S,3S)-3-({(2R)-4-[4-(1-benzofuran-3-yl)phenyl]-2-methylpiperazin-1-yl}carbonyl)-N,2-dihydroxy-5-methylhexanamide (85)

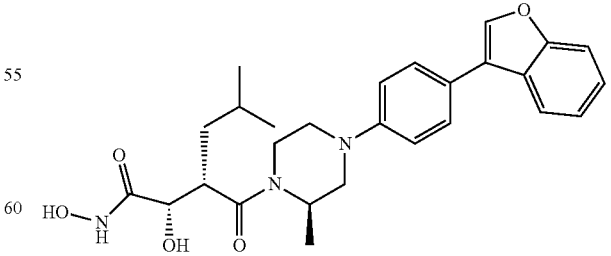

(85)

The title compound was prepared following the procedure of Example 80 (step a and b), but starting from (3R)-1-[4-(1-benzofuran-3-yl)phenyl]-3-methylpiperazine. Purification by reverse-phase chromatography gave the title product as a white powder. M⁻(ESI): 478.5; M⁺(ESI): 480.5. HPLC (Condition A), Rt: 4.1 min (HPLC purity: 98.8%).

Example 86

(2S,3S)-N,2-dihydroxy-5-methyl-3-{[(2R)-2-methyl-4-(4-propoxyphenyl)piperazin-1-yl]-carbonyl}hexanamide (86)

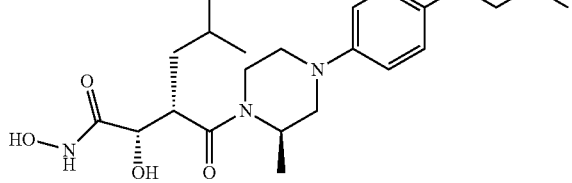

(86)

The title compound was prepared following the procedure of Example 80 (step a and b), but starting from (3R)-3-methyl-1-(4-propoxyphenyl)piperazine. Purification by reverse-phase chromatography gave the title product as a white powder. M⁻(ESI): 420.5; M⁺(ESI): 422.5. HPLC (Condition A), Rt: 2.8 min (HPLC purity: 98.1%).

Example 87

(2S,3S)-N,2-dihydroxy-5-methyl-3-({(2R)-2-methyl-4-[4-(trifluoromethyl)phenyl]piperazin-1-yl}carbonyl)hexanamide (87)

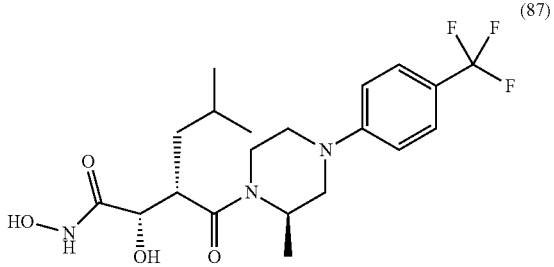

(87)

The title compound was prepared following the procedure of Example 80 (step a and b), but starting from (3R)-3-methyl-1-[4-(trifluoromethyl)phenyl]piperazine. Purification by reverse-phase chromatography gave the title product as a white powder. M⁻(ESI): 430.4; M⁺(ESI): 432.4. HPLC (Condition A), Rt: 3.7 min (HPLC purity: 99.3%).

Example 88

(2S,3S)-3-{[(2R)-4-(4-tert-butylphenyl)-2-methylpiperazin-1-yl]carbonyl}-N,2-dihydroxy-5-methylhexanamide (88)

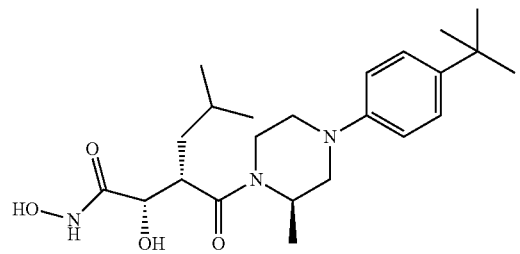

(88)

The title compound was prepared following the procedure of Example 4 (step a and b), but starting from (3R)-1-(4-tert-butylphenyl)-3-methylpiperazine. Purification by reverse-phase chromatography gave the title product as a white solid (yield 33%). M⁻(ESI): 418.4; M⁺(ESI): 420.5. HPLC (Condition A), Rt: 3.5 min (HPLC purity: 98.7%).

Example 89

(2S,3S)-3-{[(2R)-4-(5-fluoropyrimidin-2-yl)-2-methylpiperazin-1-yl]carbonyl}-N,2-dihydroxy-5-methylhexanamide (89)

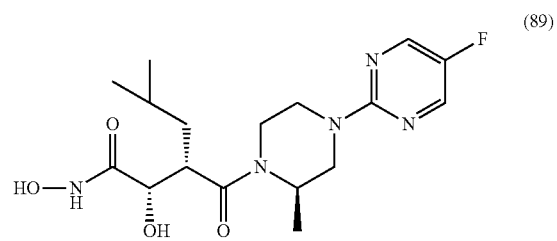

(89)

Step a) Formation of (5S)-5-((1S)-1-{[(2R)-4-(5-fluoropyrimidin-2-yl)-2-methylpiperazin-1-yl]carbonyl}-3-methylbutyl)-2,2-dimethyl-1,3-dioxolan-4-one The title compound was prepared following the procedure of Example 4 (step a), but starting from (2R)-2-[(4S)-2,2-dimethyl-5-oxo-1,3-dioxolan-4-yl]-4-methylpentanoic acid and 5-fluoro-2-[(3R)-3-methylpiperazin-1-yl]pyrimidine. The crude was purified by chromatography on silica using a gradient of EtOAc: cHex (0/10 to 4/6). The title compound was isolated as a yellow oil (413 mg, 75%). TLC (EtOAc: cHex 3:7) Rf=0.25; ¹H NMR (DMSO-d6) δ: 8.16 (s, 2H), 4.85-5.0 (m, 0.6H), 4.41-4.52 (m, 3.4H), 4.23 (m, 0.4H), 3.46-3.67 (m, 0.6H), 2.80-3.20 (m, 4H), 1.70-1.79 (m, 1H), 1.056 (m, 3H), 1.38 (s, 6H), 1.13-1.32 (m, 2H), 0.90 (m, 6H). HPLC (Condition A) Rt: 4.26 min (HPLC purity: 96.1%). LC/MS: M⁺(ESI): 409.6.

Step b) Formation of (2S,3S)-3-{[(2R)-4-(5-fluoro-pyrimidin-2-yl)-2-methylpiperazin-1-yl]carbonyl}-N,2-dihydroxy-5-methylhexanamide The title compound was prepared following the procedure of Example 4 (step b) but starting from 5-fluoro-2-[(3R)-3-methylpiperazin-1-yl]pyrimidine. Purification by reverse-phase chromatography gave the title product as a white powder. HPLC (Condition A) Rt: 2.7 min (HPLC purity: 100%). LC/MS: M⁺(ESI): 284.4.

Example 90

(2S,3S)-N,2-dihydroxy-5-methyl-3-{[(2R)-2-methyl-4-(4-propylphenyl)piperazin-1-yl]carbonyl}hexanamide (90)

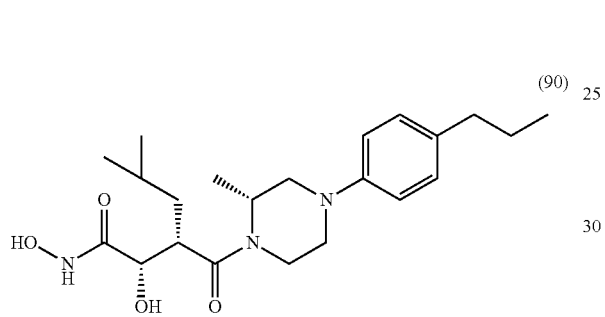

The title compound was prepared following the procedure of Example 4 (step a and b), but starting from (3R)-3-methyl-1-(4-propylphenyl)piperazine. Purification by reverse-phase chromatography gave the title product as a white solid. M⁻(ESI): 404.4; M⁺(ESI): 406.4. HPLC (Condition A), Rt: 3.2 min (HPLC purity: 90.8%).

Example 91

(2S,3S)-3-(cyclopentylmethyl)-N,2-dihydroxy-4-{(2R)-2-methyl-4-[4-(trifluoromethoxy)phenyl]piperazin-1-yl}-4-oxobutanamide (91)

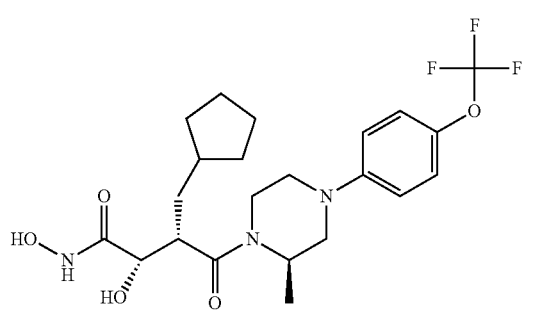

The title compound was prepared following the procedure of Example 80 (step a and b), but starting from (3R)-3-methyl-1-[4-(trifluoromethoxy)phenyl]piperazine. Purification by reverse-phase chromatography gave the title product as a white solid. M⁻(ESI): 472.4; M⁺(ESI): 474.5. HPLC (Condition A), Rt: 4.1 min (HPLC purity: 98.6%).

Example 92

(2S,3S)-3-{[(2R)-4-(2,3-dihydro-1-benzofuran-5-yl)-2-methylpiperazin-1-yl]carbonyl}-N,2-dihydroxy-5-methylhexanamide (92)

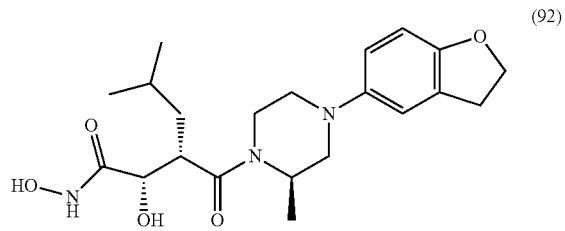

The title compound was prepared following the procedure of Example 80 (step a and b), but starting from (3R)-1-(2,3-dihydro-1-benzofuran-5-yl)-3-methylpiperazine. Purification by reverse-phase chromatography gave the title product as a white solid. M⁻(ESI): 404.4; M⁺(ESI): 406.5. HPLC (Condition A), Rt: 2.0 min (HPLC purity: 99.8%).

Example 93

(2S,3S)-3-{[(2R)-4-(1,3-benzodioxol-5-yl)-2-methylpiperazin-1-yl]carbonyl}-N,2-dihydroxy-5-methylhexanamide (93)

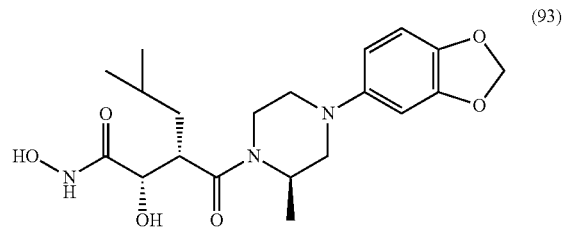

The title compound was prepared following the procedure of Example 80 (step a and b), but starting from (3R)-1-(1,3-benzodioxol-5-yl)-3-methylpiperazine. Purification by reverse-phase chromatography gave the title product as a

Example 94

(2S,3S)-N,2-dihydroxy-3-{[(2R)-4-(4-methoxyphenyl)-2-methylpiperazin-1-yl]-carbonyl}-5-methylhexanamide (94)

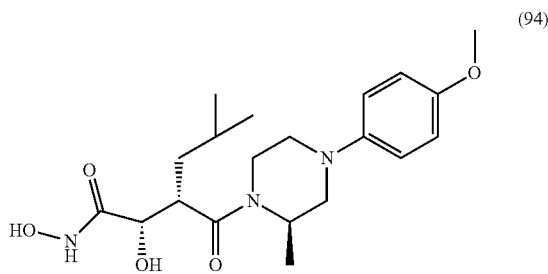

The title compound was prepared following the procedure of Example 80 (step a and b), but starting from (3R)-1-(4-methoxyphenyl)-3-methylpiperazine. Purification by reverse-phase chromatography gave the title product as a white solid. M⁻(ESI): 392.4; M⁺(ESI): 394.4. HPLC (Condition A), Rt: 2.1 min (HPLC purity: 100%).

Example 95

(2S,3S)-N,2-dihydroxy-5-methyl-3-[((2R)-2-methyl-4-{4-[(trifluoromethyl)sulfonyl]phenyl}piperazin-1-yl)carbonyl]hexanamide (95)

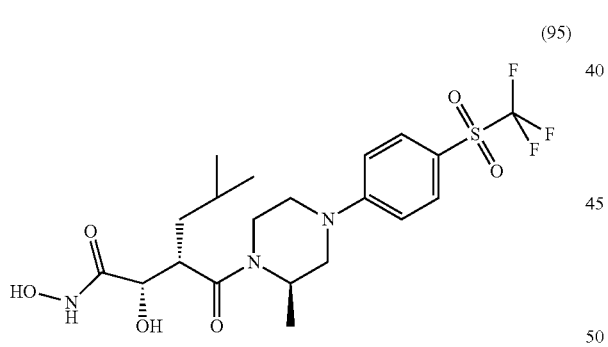

The title compound was prepared following the procedure of Example 80 (step a and b), but starting from (3R)-3-methyl-1-{4-[(trifluoromethyl)sulfonyl]phenyl}piperazine. Purification by reverse-phase chromatography gave the title product as a white solid. M⁻(ESI): 494.4; M⁺(ESI): 496.4. HPLC (Condition A), Rt: 3.6 min (HPLC purity: 98.2%).

The following examples 96-106 were prepared according to the method described in Example 4 starting respectively from:
(3R)-1-(4'-methoxybiphenyl-4-yl)-3-methylpiperazine, (3R)-1-(4-cyclohexylphenyl)-3-methylpiperazine, (3R)-1-(1-benzofuran-5-yl)-3-methylpiperazine, (3R)-1-(2,2-difluoro-1,3-benzodioxol-5-yl)-3-methylpiperazine, (3R)-1-(3-fluoro-4-methoxyphenyl)-3-methyl piperazine, (3R)-1-(3-fluoro-4-isopropoxyphenyl)-3-methylpiperazine, (3R)-1-[3-fluoro-4-(trifluoromethoxy)phenyl]-3-methylpiperazine, 3-[(3R)-3-methylpiperazin-1-yl]quinoline, (3R)-3-methyl-1-(4-methylphenyl)piperazine, (3R)-1-(3-methoxyphenyl)-3-methylpiperazine and (3R)-1-(5-chloro-2-thienyl)-3-methylpiperazine respectively.

Example 96

(2S,3S)-N,2-dihydroxy-3-{[(2R)-4-(4'-methoxybiphenyl-4-yl)-2-methylpiperazin-1-yl]carbonyl}-5-methylhexanamide (96)

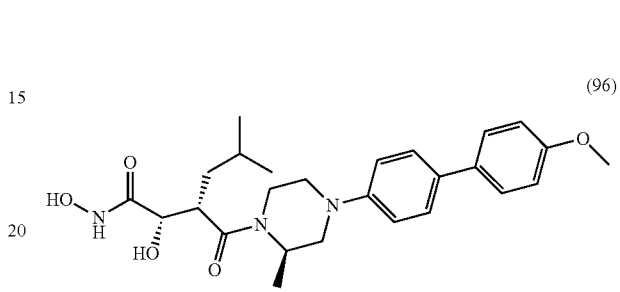

Example 97

2S,3S)-3-{[(2R)-4-(4-cyclohexylphenyl)-2-methylpiperazin-1-yl]-carbonyl}-N,2-dihydroxy-5-methylhexanamide (97)

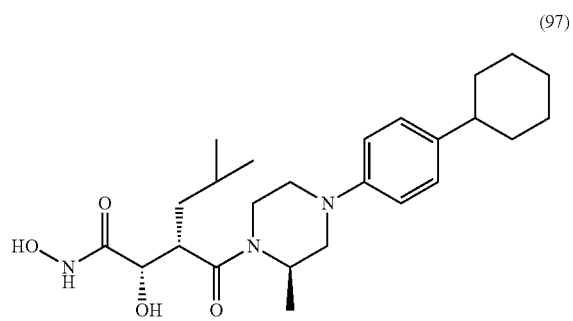

Example 98

(2S,3S)-3-{[(2R)-4-(1-benzofuran-5-yl)-2-methylpiperazin-1-yl]carbonyl}-N,2-dihydroxy-5-methylhexanamide (98)

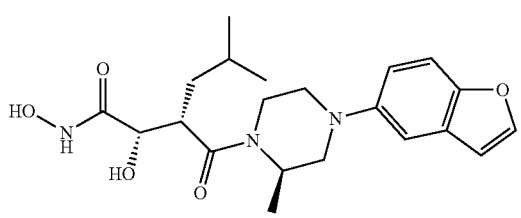

Example 99

(2S,3S)-3-{[(2R)-4-(2,2-difluoro-1,3-benzodioxol-5-yl)-2-methylpiperazin-1-yl]-carbonyl}-N,2-dihydroxy-5-methylhexanamide (99)

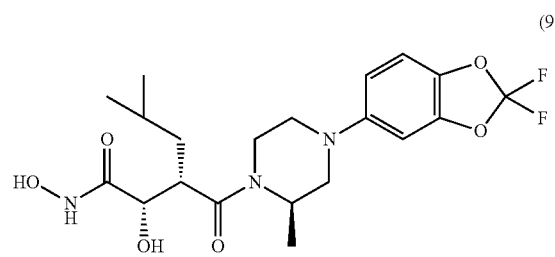

(99)

Example 100

(2S,3S)-3-{[(2R)-4-(3-fluoro-4-methoxyphenyl)-2-methylpiperazin-1-yl]carbonyl}-N,2-dihydroxy-5-methylhexanamide (100)

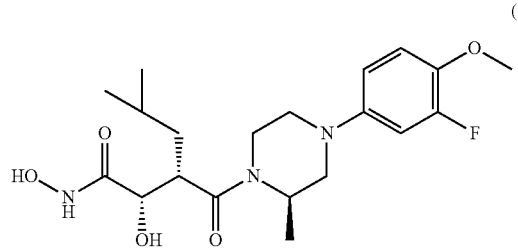

(100)

Example 101

(2S,3S)-3-{[(2R)-4-(3-fluoro-4-isopropoxyphenyl)-2-methylpiperazin-1-yl]carbonyl}-N,2-dihydroxy-5-methylhexanamide (101)

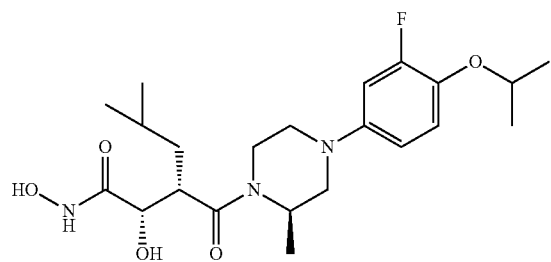

(101)

Example 102

(2S,3S)-3-({(2R)-4-[3-fluoro-4-(trifluoromethoxy)phenyl]-2-methylpiperazin-1-yl}carbonyl)-N,2-dihydroxy-5-methylhexanamide (102)

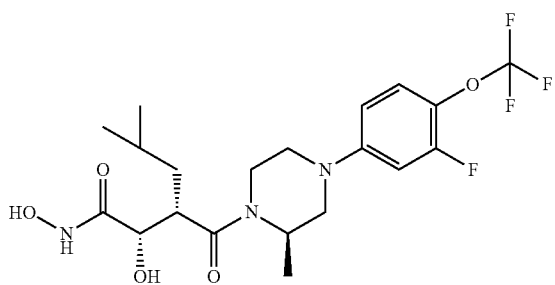

(102)

Example 103

(2S,3S)-N,2-dihydroxy-5-methyl-3-{[(2R)-2-methyl-4-Quinolin-3-yl piperazin-1-yl]carbonyl}hexanamide (103)

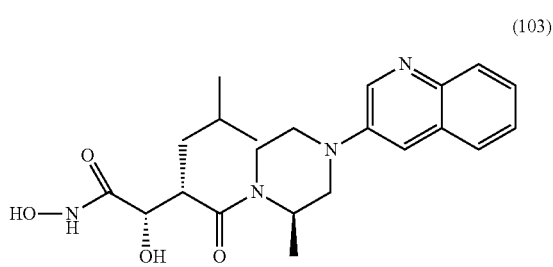

(103)

Example 104

(2S,3S)-N,2-dihydroxy-5-methyl-3-{[(2R)-2-methyl-4-(4-methyl phenyl)piperazin-1-yl]carbonyl}hexanamide (104)

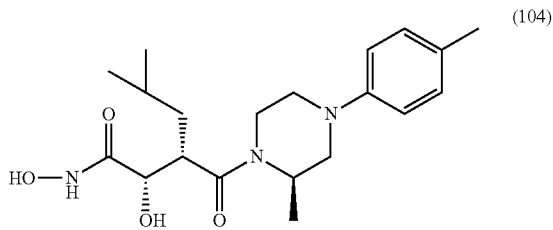

(104)

Example 105

(2S,3S)-3-{[(2R)-4-(5-chloro-2-thienyl)-2-methylpiperazin-1-yl]carbonyl}-N,2-dihydroxy-5-methylhexanamide (105

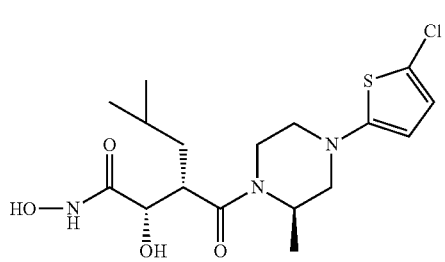

(105)

Example 106

(2S,3S)-N,2-dihydroxy-3-{[(2R)-4-(3-methoxyphenyl)-2-methylpiperazin-1-yl]carbonyl}-5-methylhexanamide (106)

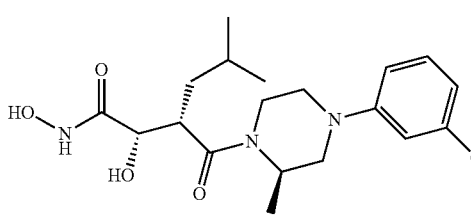

(106)

The following examples 107-114 can be prepared according to the method described in above Examples respectively from:
(3R)-1-(4'-bromobiphenyl-4-yl)-3-methylpiperazine, (3R)-3-methyl-1-[4-(2,2,2-trifluoro ethoxy)phenyl]piperazine, (3R)-1-(4-tert-butoxyphenyl)-3-methylpiperazine, (3R)-1-(4-iso propoxyphenyl)-3-methylpiperazine, 6-[(3R)-3-methylpiperazin-1-yl]quinoline, (3R)-1-[3,5-bis(trifluoromethyl)phenyl]-3-methylpiperazine, (3R)-3-methyl-1-[4-(1,3-oxazol-5-yl)phenyl]piperazine, and N,N-dimethyl-4-[(3R)-3-methylpiperazin-1-yl]aniline respectively.

Example 107

(2S,3S)-3-{[(2R)-4-(4'-bromobiphenyl-4-yl)-2-methylpiperazin-1-yl]carbonyl}-N,2-dihydroxy-5-methylhexanamide;

Example 108

(2S,3S)-N,2-dihydroxy-5-methyl-3-({(2R)-2-methyl-4-[4-(2,2,2-trifluoroethoxy)phenyl]piperazin-1-yl}carbonyl)hexanamide;

Example 109

(2S,3S)-3-{[(2R)-4-(4-tert-butoxyphenyl)-2-methylpiperazin-1-yl]carbonyl}-N,2-dihydroxy-5-methylhexanamide;

Example 110

(2S,3S)-N,2-dihydroxy-3-{[(2R)-4-(4-isopropoxyphenyl)-2-methylpiperazin-1-yl]carbonyl}-5-methylhexanamide;

Example 111

(2S,3S)-N,2-dihydroxy-5-methyl-3-{[(2R)-2-methyl-4-quinolin-6-yl piperazin-1-yl]carbonyl}hexanamide;

Example 112

(2S,3S)-3-({(2R)-4-[3,5-bis(trifluoromethyl)phenyl]-2-methylpiperazin-1-yl}carbonyl)-N,2-dihydroxy-5-methylhexanamide

Example 113

(2S,3S)-N,2-dihydroxy-5-methyl-3-({(2R)-2-methyl-4-[4-(1,3-oxazol-5-yl)phenyl]piperazin-1-yl}carbonyl)hexanamide;

Example 114

(2S,3S)-3-({(2R)-4-[4-dimethylamino)phenyl]-2-methylpiperazin-1-yl}carbonyl)-N,2-dihydroxy-5-methylhexanamide.

Biological Assays:
The compounds of the present invention may be subjected to the following assays:

Example 115

Enzyme Inhibition Assays

Compounds of the invention were tested to assess their activities as inhibitors of MMP-1, MMP-2, MMP-9, MMP-14 and MMP-12.

MMP-9 Assay Protocol

Compounds of the invention were tested for inhibitory activity against 92 kDa gelatinase (MMP-9) in an assay using a coumarin-labeled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (McaPLGLDpaAR) (Knight et al, *FEBS Lett.* 1992; 263-266).

Stock solutions were made up as follows: Assay Butter: 100 mM Tris-HCl pH 7.6 is containing 100 mM NaCl, 10 mM $CaCl_2$, and 0.05% Brij 35.

Substrate: 0.4 mM McaPLGLDpaAR (from Bachem) (0.437 mg/ml) stock solution in 100% DMSO (stored at −20° C.). Dilute to 8 μM in assay butter.

Enzyme: Recombinant human 92 kDa gelatinase (MMP-9; APMA (4-aminophenyl mercuric acetate)-activated if necessary) appropriately diluted in assay butter.

Test Compounds were prepared initially as 10 mM compound solution in 100% DMSO, diluted to 1 mM in 100% DMSO, then serially diluted 3-fold in 100% DMSO across columns 1-10 of a 96-well microtitre plate Assay concentration range, 100 μM (column 1) to 5.1 nM (column 10).

The assay was performed in a total volume of 100 μL per well in 96-well microfilm plates. Activated enzyme (20 μL) was added to the wells followed by 20 μL of assay butter. Appropriate concentrations of test compounds dissolved in 10 μL of DMSO were then added followed by 50 μL of McaPLGLDpaAR (8 μM, prepared by dilution of DMSO stock in assay butter). For each as say ten concentrations of test compound were examined in duplicate. Control wells lack either enzyme or test compound. The reactions were incubated at 37° C. for 2 hours. The fluorescence at 405 nm was measured immediately with an SLT Fluostar fluorometer (SL T Labinstruments GmbH, Grödig, Austria) using 320 nm excitation, without stopping the reaction.

The effect of the test compound was determined from the dose response curve generated by the 10 duplicate concentrations of inhibitor. The $IC_{50}$ (the concentration of compound required to give a 50% decrease in enzyme activity) was obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the $IC_{50}$; d=is the slope). The result was rounded to one significant figure.

MMP-12 Assay Protocol

Compounds of the invention were tested for inhibitory activity against metalloelastase (MMP-12) in an assay using a coumarin-labelled peptide substrate, (7-methoxycoumarin-4-yl)acetyl-Pro-Leu-Gly-Leu-(3-[2,4-dinitrophenyl]-L-2,3-diaminopropionyl)-Ala-Arg-NH2 (McaPLGLDpaAR) (Knight et al, 1992, above). The protocol for this assay was as described for the MMP-9 assay above.

MMP-1 Assay Protocol

Compounds of the invention were tested for inhibitory activity against collagenase (MMP-1) in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (Mca PLGLDpaAR) (Knight et al, 1992, above). The protocol for this assay was as described for the MMP-9 assay above.

MMP-14 Assay Protocol

Compounds of the invention were tested for inhibitory activity against MMP-14 in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (Mca PLGLD paAR) (Knight et al, 1992, above). The protocol for this assay was as described for the MMP-9 assay above.

MMP-2 Assay Protocol

Compounds of the invention were tested for inhibitory activity against gelatinase A (MMP-2) in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (Mca PLGLDpaAR) (Knight et al, 1992, above). The protocol for this assay was as described for the MMP-9 assay above.

The results are expressed in terms of $IC_{50}$ (the concentration of compound required to give a 50% decrease in enzyme activity) and are presented in Table 1 below for compounds of Formula (I) and in Table 2 below for compounds of Formula (VI).

TABLE 1

| | $IC_{50}$ on different MMPs: | | | |
|---|---|---|---|---|
| Example | MMP-1 $IC_{50}$ (nM) | MMP-2 $IC_{50}$ (nM) | MMP-9 $IC_{50}$ (nM) | MMP-12 $IC_{50}$ (nM) |
| Example 1 | 418 | 3 | 5 | 4 |
| Example 2 | 876 | 17 | 7 | 103 |
| Example 3 | >5000 | 42 | 285 | 31 |
| Example 4 | 301 | 4 | 12 | 17 |
| Example 6 | >5000 | 8 | 22 | 20 |
| Example 9 | >5000 | 136 | 233 | 33 |
| Example 14 | >5000 | 89 | 585 | 4 |

TABLE 1-continued

| | $IC_{50}$ on different MMPs: | | | |
|---|---|---|---|---|
| Example | MMP-1 $IC_{50}$ (nM) | MMP-2 $IC_{50}$ (nM) | MMP-9 $IC_{50}$ (nM) | MMP-12 $IC_{50}$ (nM) |
| Example 53 | >5000 | 7.5 | 7 | 5 |
| Example 56 | >5000 | 4.8 | 41 | 6 |
| Example 58 | >5000 | 38 | 194 | 7 |
| Example 61 | >5000 | 8 | 48 | 2 |
| Example 91 | 1150 | 3 | 49 | <1 |

TABLE 2

| | $IC_{50}$ on different MMPs: | | | |
|---|---|---|---|---|
| Example | MMP-1 $IC_{50}$ (nM) | MMP-2 $IC_{50}$ (nM) | MMP-9 $IC_{50}$ (nM) | MMP-12 $IC_{50}$ (nM) |
| Example 20 | >5000 | 82 | 37 | 29 |
| Example 37 | >5000 | 47 | 45 | 17 |
| Example 37 | >5000 | 65 | 52 | 23 |
| Example 46 | >5000 | 179 | 133 | 34 |

Example 116

IL-2-Induced Peritoneal Recruitment of Lymphocytes

Administration of IL-2 intraperitoneally causes migration of lymphocytes into the intraperitoneal cavity. This is a model for the cellular migration that occurs during inflammation.

Protocol

C3H/HEN mice (Elevage Janvier, France) were intraperitoneally injected with IL-2 (Serono Pharmaceutical Research Institute, 20 µg/kg, in saline).

Compounds of the invention were suspended in 0.5% carboxymethylcellulose (CMC)/0.25% tween-20 and were administered by s.c. or p.o. route (10 ml/kg) 15 min prior to administration of IL-2.

Twenty-four hours after administration of IL-2, peritoneal white blood cells were collected by 3 successive lavages of the peritoneal cavity with 5 ml phosphate buffered saline (PBS)-1 mM EDTA (+4° C.). The suspension was centrifuged (1700 g×10 min at +4° C.). The resulting pellet was suspended in 1 ml PBS-1 mM EDTA.

Lymphocytes were identified and counted using a Beckman/Coulter counter.

Experimental Design

The animals were divided into 6 groups (6 mice each group):

Group 1: (baseline) received 0.5% CMC/0.25% tween-20 (vehicle of compound of the invention) and saline (vehicle of IL-2);

Group 2: (control IL-2) received 0.5% CMC/0.25% tween-20 and injection of IL-2;

Group 3: Experimental group (Compound of the invention Dose 1) received a compound of the invention and injection of IL-2;

Group 4: Experimental group (Compound of the invention Dose 2) received a compound of the invention and injection of IL-2;

Group 5: Experimental group (Compound of the invention Dose 3) received a compound of the invention and injection of IL-2;

Group 6: Reference group received reference compound dexamethasone and injection of IL-2.

Calculation

Inhibition of lymphocyte recruitment was calculated as follows:

$$\% \text{ inhibition} = \frac{1(LyX - Ly1)}{(Ly2 - Ly1)} \times 100\%$$

Where Ly 1=Number of lymphocytes in group 1 (E3/µl), Ly 2=Number of lymphocytes in group 2 (E3/µl), Ly X=Number of lymphocytes in group X (3-5) (E3/µl).

The results for compounds according to Formula (I) are presented in Table 3 and for compounds according to Formula (VI) in Table 4 below.

TABLE 3

Percentage of inhibition of IL-2-induced peritoneal recruitment of lymphocytes by compounds of the invention:

| Example | Dose (mg/kg) | Route | % inhibition |
|---|---|---|---|
| Example 4 | 1 | po | 39 |
| Example 6 | 1 | po | 46 |
| Example 6 | 3 | po | 65 |
| Example 7 | 1 | po | 46 |
| Example 53 | 1 | po | 61 |
| Example 61 | 1 | po | 67 |

TABLE 4

Percentage of inhibition of IL-2-induced peritoneal recruitment of lymphocytes by compounds of the invention:

| Example | Dose (mg/kg) | Route | % inhibition |
|---|---|---|---|
| Example 20 | 1 | po | 38 |
| Example 37 | 1 | po | 42 |
| Example 47 | 1 | po | 41 |

Example 117

$CCl_4$-Induced Liver Fibrosis Model

Carbon tetrachloride ($CCl_4$) induces liver fibrosis when administered intraperitoneally (Bulbena O, Culat J, Bravo M L., *Inflammation* 1997 October; 21(5):475-88). Compounds of the invention can be evaluated for their ability to prevent the $CCl_4$-induced formation of fibrotic tissue.

Animals

Male Sprague-Dawley rats, 7 weeks old, weight approx. 300 g from Charles River/Iffa-Crédo, St-Germain/l'Arbresle, France.

Rats are acclimatised for 5 days before commencing experiments, in air-conditioned rooms, 2 animals per cage, Temperature: 22° C.±2, Relative humidity: 55%±10 Light: 12 hour cycle (7 a.m.-7 p.m.), Cage: Makrolon® cage 42.5× 26.6×15 on each fitted with a stainless steel cover-feed rack.

The study involves the following groups of 8 animals each, as indicated below.

Group 1:"Sham" animals receive $CCl_4$ vehicle (i.p.) and once daily, the vehicle of test substance (s.c.)

Group 2: Positive control group receives $CCl_4$ (i.p.), and once daily, the vehicle of the test substance (s.c.)

Group 3:Experimental group receives $CCl_4$ (i.p.), and once daily, 2 mg/kg s.c. of compound according to the invention.

Group 4: Experimental group receives $CCl_4$ (i.p.), and once daily, 10 mg/kg s.c. of the compound according to the invention.

Group 5: Experimental group receives $CCl_4$ (i.p.) and once daily, 20 mg/kg s.c. of the compound according to the invention.

Rats were labeled on their tails. The labels are checked and renewed, if necessary, after every $CCl_4$ injection.

Procedure $CCl_4$ (Prolabo) in olive oil is administered every 3 days for three weeks by intra-peritoneal injection (0.25 ml $CCl_4$/kg body weight, diluted in oil 1:1 vol:vol for a total volume of 0.5 ml/kg). Animals are weighed daily. If body weight decreased by more than 10% of the initial weight, the animal is excluded from the study.

Vehicles and compound are used as follows:
$CCL_4$ was administered in olive oil (Prolabo) at a 1:1 dilution;
The compound of the invention is suspended in 0.25% Tween-80 and 0.25% carboxymethylcellulose in sterile 0.9% NaCl. The solution is kept at 4° C. throughout the experiment and used each day to prepare the suspensions.

The compound of the invention is administered daily by subcutaneous (s.c.) injection at a volume of administration of 5 ml/kg. Groups 1 and 2 are dosed s.c. with 5 ml/kg of vehicle. Freshly prepared solutions are used on each day of the experiment. Administrations are carried out each day at the same time.

The treatment of groups of this study is started for each animal at the time of the first $CCl_4$ administration and is continued for 21 consecutive days. The last administration of test substances or vehicle is done 1 day before the sacrifice of the animals.

Results

Death are reported, date and supposed cause are reported.

Serum Enzyme Levels

Animals are killed 21 days following the first $CCl_4$ administration by isofurane inhalation. Blood is withdrawn individually at the time of sacrifice, i.e. one day after the last administration of test substance or vehicle. Blood is centrifuged at 4° C. Plasma is carefully collected and aliquoted in 3 fractions. Plasma aspartate amino transferase (ASAT) and alanine amino transferase (ALAT) levels are measured in order to assess liver necrosis. Increased ASAT and ALAT levels in serum are associated with liver impairment. Average ASAT and ALAT levels for control animals and those treated with the compound of the invention at three different dosages are reported.

Histological Evaluation of Liver Fibrosis

Liver fibrosis is evaluated by measuring the area of fibrosis in the liver using microchotomy. Results are reported as percentage area that is fibrotic.

The liver is removed, the three lobes are dissected and samples are removed and either fixed in 10% formaldehyde or frozen at −80° C.

Liver sections are embedded in paraffin blocks. Sectioning and staining with Sirius red are performed. Quantification of the fibrosis in liver is carried out on a minimum of 3 sections taken from different locations in the liver. The quantitative analysis is performed using an image analyser (Imstar) and the software Morphostar.

Average area percentages of fibrosis in the livers of animals in the different groups are calculated.

Example 118

Chronic Obstructive Pulmonary Disease (COPD) Model

Compounds of the invention can be evaluated for their ability to prevent cigarette smoke-induced COPD.

Female AJ mice (Harlan, 17-25 g) are exposed daily to cigarette smoke (CS) for 11 consecutive days in groups of 5, in individual clear chambers. Animals are weighed prior to treatment, on day 6 of exposure and on day 12. The CS was generated using 1R1 cigarettes purchased from the Institute of Tobacco Research, University of Kentucky, USA and is allowed to enter the chambers at a flow rate of 100 ml/min.

In order to minimise any potential problems caused by repeated exposure to a high level of daily CS, the exposure of the mice to TS is increased gradually over the time to a maximum of 6 cigarettes from day 5 to day 11 (approximately 48 min exposure).

A sham group of mice is also exposed to air on a daily basis for equivalent lengths of time as controls (no CS exposure).
Treatment Compounds of the invention are prepared in 0.5% carboxymethylcellulose Na salt (CMC, Sigma reference C-4888) as vehicle.

Animals are orally dosed twice daily by gavage in a dose volume of 5 ml/kg, 1 h prior to air or CS exposure and 6 h after the cessation of the exposure.

Sham animals (n=10) received vehicle and are exposed to air for up to a maximum of 50 minutes per day. The control group (n=10) received vehicle and is exposed to CS (up to a maximum of 6 cigarettes per day). Additional groups are exposed to CS (from up to a maximum of 6 cigarettes per day) and treated with one of the test compounds or the reference compound.
Bronchoalveolar Lavage and Cytospin Analysis Twenty-four hours after the last CS exposure, bronchoalveolar lavage is performed as follows:

The trachea is dissected under deep anesthesia (sodium pentobarbitone) and cannulated using a Portex nylon intravenous cannula shortened to approximately 8 mm. Phosphate buffered saline (PBS, Gibco) containing 10 units/ml heparin (0.4 ml) is gently instilled and withdrawn 3 times. The lavage fluid is placed in an Eppendorf tube and kept on ice prior to subsequent determinations. Then, lavage fluid is separated from cells by centrifugation.

The supernatant is removed and frozen for subsequent analysis. The cell pellet is resuspended in PBS and total cell numbers are calculated by counting a stained aliquot (Turks stain) under a microscope using a haemocytometer.

Differential cell count is then performed as follows: The residual cell pellet is diluted to approximately 105 cells per ml. A volume of 500 µl is placed in the funnel of a cytospin slide and is centrifuged for 8 min at 800 rpm. The slide is air-dried and stained using 'Kwik-Diff' solutions (Shandon) following purchaser instructions. Slides are dried and coverslipped and differential cell count is done using light microscopy. Up to 400 cells are counted for each slide. Cells were differentiated using standard morphometric techniques.
Statistical Analysis The mean+/−S.D. is calculated for each experimental group.

Results are analyzed using a one-way analysis of variance (ANOVA), followed by a Bonferroni correction for multiple comparisons. Statistical significance is considered with $p<0.05$.

Example 119

Experimental Allergic Encephalomyelitis (EAE) Model

Compounds according to the invention can be evaluated for their activity in a model for multiple sclerosis in mice.

Animals

C57BL/6NCrlBR female mice are used. Mice are kept in wire cages (cm 32×14×13 h) with stainless steel feeders and fed on a standard diet (4RF21, Charles River, Italy) and water ad libitum. From day 7, wet pellets are also placed every day on the bottom of the cage. Plastic bottles are used in addition to the automatic water system.
Experimental Procedure Mice are immunized (day=0) by injecting s.c. in the left flank 0.2 ml of an emulsion composed of 200 µg $MOG_{35-55}$ peptide (Neosystem, Strasbourg, France) in Complete Freund's Adjuvant (CFA, Difco, Detroit, U.S.A.) containing 0.5 mg of *Mycobacterium tuberculosis*. Immediately after, they receive an i.p. injection of 500 ng pertussis toxin (List Biological Lab., Campbell, Calif., U.S.A.) dissolved in 400 µL of buffer (0.5 M NaCl, 0.017% Triton X-100, 0.015 M Tris, pH=7.5). On day 2, the animals are given a second injection of 500 ng pertussis toxin.

On day 7, the mice receive a second dose of 200 µg of $MOG_{35-55}$ peptide in CFA injected s.c. in the right flank. Starting approximately from day 8-10, this procedure results in a progressing paralysis, arising from the tail and ascending up to the forelimbs.

Animals are individually weighed and are examined for the presence of paralysis that is scored according to the following score-system (1):
0=no signs of disease
0.5=partial tail paralysis
1=tail paralysis
1.5=tail paralysis+partial unilateral hindlimb paralysis
2=tail paralysis+bilateral hindlimb weakness or partial paralysis
2.5=tail paralysis+partial hindlimb paralysis (lowered pelvi)
3=tail paralysis+complete hindlimb paralysis
3.5=tail paralysis+hindlimb paralysis+incontinence
4=tail paralysis+hindlimb paralysis+weakness or partial paralysis of forelimbs
5=moribund or dead Mortality and clinical signs are monitored daily in each group of treatment, by a technician who is unaware of treatments.

Daily treatment with compounds, their vehicle or with a reference compound starts on day 7 and continued for 15 or 21 consecutive days in all groups.
Histopathological Examination At the end of the treatment period, each animal is anesthetised with sodium pentobarbital and is transcardially perfused-fixed with 4% paraformaldehyde via the left ventricle. Fixed spinal cords are then carefully dissected out.

Spinal cord slices are embedded in paraffin blocks. Sectioning and staining with hematoxylin and eosin and CD45 staining for inflammation, and with Kluver-PAS (Luxol fast blue plus Periodic Acid Schiff staining) and Bielchowski's staining for the detection of demyelination and axonal loss, are performed.

In the spinal cord, the total area of all slices is measured for each animal as points of intersection of a 10×10 grid at a magnification of 0.4×0.4 mm per grid. The perivascular inflammatory infiltrates are counted in each slice in order to obtain a total value for each animal and evaluated as number of infiltrates per $mm^2$. Demyelination and axonal loss areas are measured for each animal as points of intersection of 10×10 grid at a magnification of 0.1×0.1 mm per grid and are expressed as a percentage of total demyelination area over the total area of the slices.

Data Evaluation and Statistical Analysis

The results of clinical and histopathological observations are expressed as the mean (±SEM) scores in each treatment group. Values obtained in the test drug-treated groups are compared with that of the positive control group. Significance of differences among groups relating to clinical score are analysed by one-way ANOVA, followed in case of significance ($p<0.05$) by Fisher test.

Differences among groups for the presence of perivascular inflammatory infiltrates and the extent of demyelination and axonal loss in the spinal cord as well as body weight data are analysed by one-way ANOVA, followed in case of significance ($p<0.05$) by Fisher test.

Example 120

Preparation of a Pharmaceutical Formulation

The following formulation examples illustrate representative pharmaceutical compositions according to the present invention being not restricted thereto.
Formulation 1—Tablets
A compound of the invention is admixed as a dry powder with a dry gelatin binder in an approximate 1:2 weight ration. A minor amount of magnesium stearate is added as a lubricant. The mixture is formed into 240-270 mg tablets (80-90 mg) of active N-hydroxyamide derivative per tablet) in a tablet press.
Formulation 2—Capsules
A compound of the invention is admixed as a dry powder with a starch diluent in an approximate 1:1 weight ratio. The mixture is filled into 250 mg capsules (125 mg of active N-hydroxyamide derivative per capsule).
Formulation 3—Liquid
A compound of the invention (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.
Formulation 4—Tablets
A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active N-hydroxyamide derivative) in a tablet press.
Formulation 5—Injection
A compound of the invention is dissolved in a buffered sterile saline injectable aqueous medium to a concentration of approximately 5 mg/ml.

The invention claimed is:
1. A N-hydroxyamide according to Formula (I),

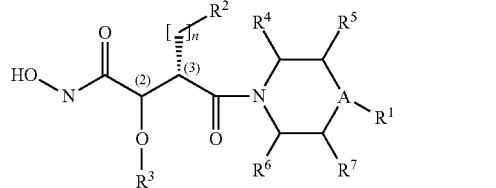

wherein:
A is —C(B)—;
B is B forms a bond with either $R^5$ or $R^7$;
$R^1$ is selected from $C_1$-$C_6$ alkyl, $C_3$-$C_8$-cycloalkyl, aryl, pyridinyl, pyrazinyl, thiadiazolyl, pyrimidinyl, oxadiazolyl, quinolinyl, thienyl, benzofuranyl, amino and alkoxy;
$R^2$ is selected from H, $C_1$-$C_6$ alkyl, $C_2$-$C_6$ alkenyl, $C_2$-$C_6$ alkynyl, $C_3$-$C_8$-cycloalkyl, and aryl;
$R^3$ is selected from H, $C_1$-$C_6$ alkyl, $C_2$-$C_6$ alkenyl and $C_2$-$C_6$ alkynyl;
$R^4$, $R^5$, $R^6$ and $R^7$ are independently selected from H, $C_1$-$C_6$ alkyl, $C_2$-$C_6$ alkenyl, $C_2$-$C_6$ alkynyl; or $R^4$ and $R^7$ form together a —$CH_2$— linkage;
n is an integer selected from 1, 2, 3, 4, 5 and 6;
wherein $R^1$-$R^7$ may be substituted by from 1 to 5 substituents selected from the group consisting of $C_1$-$C_6$-alkyl, amino, halogen, carboxy, trihalomethyl, cyano, hydroxy, mercapto, and nitro;
Carbons (2) and (3) are two chiral centers, wherein chiral center (2) has a configuration selected from "S" and "R" and wherein chiral center (3) has a "S" configuration as well as pharmaceutically acceptable salts thereof.
2. A N-hydroxyamide according to claim 1, wherein $R^1$ is selected from aryl, pyridinyl, pyrazinyl, thiadiazolyl, pyrimidinyl, oxadiazolyl, quinolinyl, thienyl, and benzofuranyl.
3. A N-hydroxyamide according to claim 1 wherein $R^2$ is selected from H, $C_1$-$C_6$ alkyl, $C_2$-$C_6$ alkenyl and $C_2$-$C_6$ alkynyl.
4. A N-hydroxyamide according to claim 1 wherein $R^2$ is aryl.
5. A N-hydroxyamide according to claim 1 wherein $R^2$ is selected from optionally substituted $C_3$-$C_8$-cycloalkyl.
6. A N-hydroxyamide according to claim 1 wherein $R^3$ is H.
7. A N-hydroxyamide according to claim 1 wherein $R^4$, $R^5$ and $R^7$ are H.
8. A N-hydroxyamide according to claim 1 wherein $R^6$ is selected from H and $C_1$-$C_6$ alkyl.
9. A N-hydroxyamide according to claim 1 wherein $R^5$ and $R^6$ are H and $R^4$ and $R^7$ can form together a —$CH_2$— linkage.
10. A N-hydroxyamide according to claim 1 wherein the configuration of the chiral carbons is (2S), (3S).
11. A N-hydroxyamide according to claim 1 wherein the configuration of the chiral carbons is (2R), (3S).
12. A N-hydroxyamide according to claim 1 having a Formula (Ib):

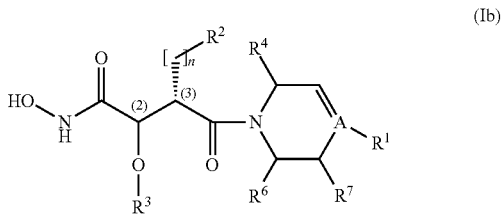

wherein A is a carbon atom;
$R^1$ is selected from H, $C_1$-$C_6$ alkyl, $C_3$-$C_8$-cycloalkyl, pyridinyl, pyrazinyl, thiadiazolyl, pyrimidinyl, oxadiazolyl, quinolinyl, thienyl, benzofuranyl, amino and alkoxy;
$R^2$ is selected from H, $C_1$-$C_6$ alkyl, $C_2$-$C_6$ alkenyl, $C_2$-$C_6$ alkynyl, $C_3$-$C_8$-cycloalkyl, and aryl;

$R^3$ is selected from H, $C_1$-$C_6$ alkyl, $C_2$-$C_6$ alkenyl and $C_2$-$C_6$ alkynyl;

$R^4$, $R^6$ and $R^7$ are independently selected from H, $C_1$-$C_6$ alkyl, $C_2$-$C_6$ alkenyl, $C_2$-$C_6$ alkynyl; or $R^4$ and $R^7$ form together a —$CH_2$— linkage;

n is an integer selected from 1, 2, 3, 4, 5 and 6;

Carbons (2) and (3) are two chiral centers, wherein chiral center (2) has a configuration selected from "S" and "R" and wherein chiral center (3) has a "S" configuration as well as pharmaceutically acceptable salts thereof.

13. A N-hydroxyamide according to claim 12 wherein $R^1$ is selected from aryl and $R^3$, $R^4$, $R^5$, $R^6$ and $R^7$ are H.

14. A pharmaceutical composition comprising at least one N-hydroxyamide according to claim 1 and a pharmaceutically acceptable carrier, diluent or excipient thereof.

15. A process for the preparation of a N-hydroxyamide according to claim 1, comprising reacting a compound of Formula (IV) with $H_2N$—O—$R^8$:

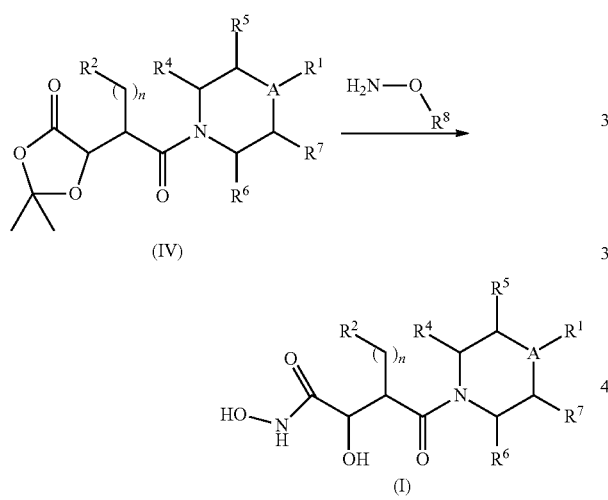

(IV)

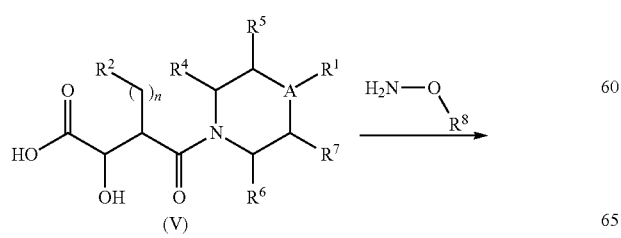

(I)

wherein A, $R^1$, $R^2$, $R^4$, $R^5$, $R^6$, $R^7$ and n are as defined in claim 1 and $R^8$ is selected from H and a protective group selected from t-butyl, benzyl, trialkylsilyl, tetrahydropyranyl.

16. A process for the preparation of a N-hydroxyamide according to claim 1, comprising reacting a compound of Formula (V) with $H_2N$—O—$R^8$:

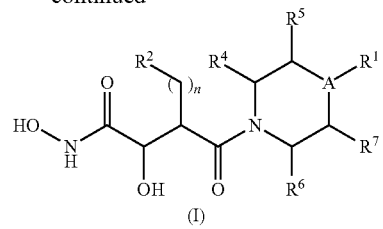

(V)

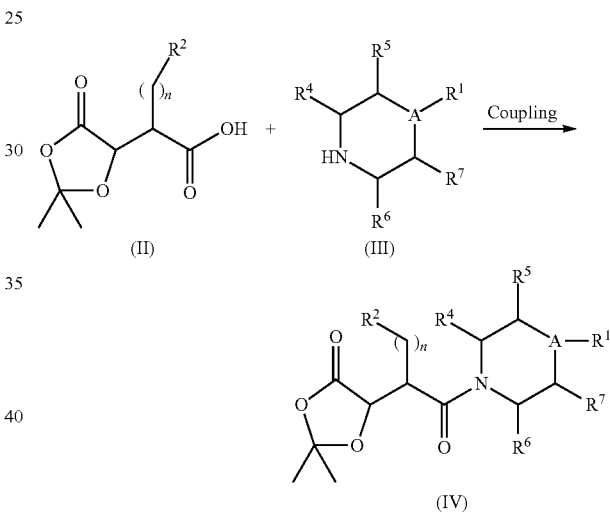

(I)

wherein A, $R^1$, $R^2$, $R^4$, $R^5$, $R^6$, $R^7$ and n are as defined in claim 1 and $R^8$ is selected from H and a protective group.

17. A process according to claim 15, further comprising removing the protecting group of $R^8$ when $R^8$ is a protective group.

18. A process for the preparation of a N-hydroxyamide according to claim 15, further comprising reacting a compound of Formula (II) with an amine of Formula (III) to form the intermediate of Formula (IV), optionally in presence of a coupling agent selected from DIC, EDC, TBTU, DCC, HATU, PyBOP®, Isobutyl chloroformate and 1-methyl-2-chloropyridinium iodide (II)     (III)

(IV)

wherein A, $R^1$, $R^2$, $R^4$, $R^5$, $R^6$, $R^7$ and n are as defined in claim 15; G is a group selected from OH and Cl.

19. A compound according to Formula (IV):

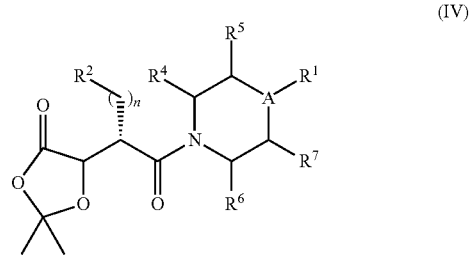

(IV)

wherein A is —C(B)—;
B forms a bond with either $R^5$ or $R^7$;
$R^1$ is selected from $C_1$-$C_6$ alkyl, $C_3$-$C_8$-cycloalkyl, aryl, pyridinyl, pyrazinyl, thiadiazolyl, pyrimidinyl, oxadiazolyl, quinolinyl, thienyl, benzofuranyl, amino and alkoxy;

$R^2$ is selected from H, $C_1$-$C_6$ alkyl, $C_2$-$C_6$ alkenyl, $C_2$-$C_6$ alkynyl, $C_3$-$C_8$-cycloalkyl, and aryl;

$R^4$, $R^5$, $R^6$ and $R^7$ are independently selected from H, $C_1$-$C_6$ alkyl, $C_2$-$C_6$ alkenyl, $C_2$-$C_6$ alkynyl; or $R^4$ and $R^7$ form together a —$CH_2$— linkage;

n is an integer selected from 1, 2, 3, 4, 5 and 6;

wherein $R^2$, $R^4$, $R^5$, $R^6$ and $R^7$ may be substituted by from 1 to 5 substituents selected from the group consisting of $C_1$-$C_6$-alkyl, amino, halogen, carboxy, trihalomethyl, cyano, hydroxy, mercapto, and nitro.

20. A compound according to Formula (V):

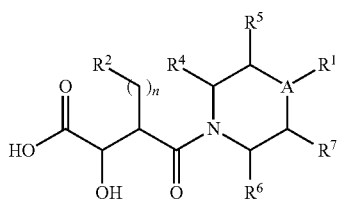

(V)

wherein

A is —C(B)—;

B forms a bond with either $R^5$ or $R^7$;

$R^1$ is selected from $C_1$-$C_6$ alkyl, $C_3$-$C_8$-cycloalkyl, aryl, pyridinyl, pyrazinyl, thiadiazolyl, pyrimidinyl, oxadiazolyl, quinolinyl, thienyl, benzofuranyl, amino and alkoxy;

$R^2$ is selected from H, $C_1$-$C_6$ alkyl, $C_2$-$C_6$ alkenyl, $C_2$-$C_6$ alkynyl, $C_3$-$C_8$-cycloalkyl, and aryl;

$R^4$, $R^5$, $R^6$ and $R^7$ are independently selected from H, $C_1$-$C_6$ alkyl, $C_2$-$C_6$ alkenyl, $C_2$-$C_6$ alkynyl; or $R^4$ and $R^7$ form together a —$CH_2$— linkage;

n is an integer selected from 1, 2, 3, 4, 5 and 6;

wherein $R^2$, $R^4$, $R^5$, $R^6$ and $R^7$ may be substituted by from 1 to 5 substituents selected from the group consisting of $C_1$-$C_6$-alkyl, amino, halogen, carboxy, trihalomethyl, cyano, hydroxy, mercapto, and nitro.

* * * * *